United States Patent
Gomis et al.

(10) Patent No.: US 11,041,213 B2
(45) Date of Patent: *Jun. 22, 2021

(54) METHOD FOR THE DIAGNOSIS, PROGNOSIS AND TREATMENT OF PROSTATE CANCER METASTASIS

(71) Applicant: INBIOMOTION S.L., Barcelona (ES)

(72) Inventors: Roger Gomis, Barcelona (ES); Joël Jean-Mairet, Barcelona (ES)

(73) Assignee: INBIOMOTION S.L., Barcelona (ES)

( * ) Notice: Subject to any disclaimer, the term of this patent is extended or adjusted under 35 U.S.C. 154(b) by 166 days.

This patent is subject to a terminal disclaimer.

(21) Appl. No.: 16/142,168

(22) Filed: Sep. 26, 2018

(65) Prior Publication Data

US 2019/0256922 A1   Aug. 22, 2019

Related U.S. Application Data

(63) Continuation of application No. 15/183,419, filed on Jun. 15, 2016, now Pat. No. 10,119,171, which is a continuation-in-part of application No. 14/435,128, filed as application No. PCT/IB2013/002866 on Oct. 9, 2013, now Pat. No. 10,114,022.

(60) Provisional application No. 61/713,318, filed on Oct. 12, 2012.

(51) Int. Cl.
*C07K 16/32* (2006.01)
*C12Q 1/6886* (2018.01)
*G01N 33/574* (2006.01)

(52) U.S. Cl.
CPC ............ *C12Q 1/6886* (2013.01); *C07K 16/32* (2013.01); *G01N 33/57434* (2013.01); *C07K 2317/565* (2013.01); *C12Q 2600/106* (2013.01); *C12Q 2600/112* (2013.01); *C12Q 2600/118* (2013.01); *C12Q 2600/158* (2013.01); *G01N 2333/4703* (2013.01); *G01N 2800/52* (2013.01)

(58) Field of Classification Search
CPC .................................................. C12Q 1/6886
USPC ........................................................ 435/7.1
See application file for complete search history.

(56) References Cited

U.S. PATENT DOCUMENTS

| | | | |
|---|---|---|---|
| 5,093,246 A | 3/1992 | Cech et al. | |
| 6,274,338 B1 | 8/2001 | Glimcher et al. | |
| 6,355,623 B2 | 3/2002 | Seidman et al. | |
| 6,740,522 B2 | 5/2004 | Anderson et al. | |
| 7,097,834 B1 | 8/2006 | Boyle | |
| 7,364,736 B2 | 4/2008 | Boyle et al. | |
| 7,411,050 B2 | 8/2008 | Anderson | |
| 9,702,878 B2 | 7/2017 | Gomis et al. | |
| 10,006,091 B2 | 6/2018 | Gomis et al. | |
| 10,047,398 B2 | 8/2018 | Gomis et al. | |
| 10,114,022 B2 | 10/2018 | Gomis et al. | |
| 10,119,171 B2 | 11/2018 | Gomis et al. | |
| 10,793,642 B2 | 10/2020 | Gomis et al. | |
| 10,866,241 B2 | 12/2020 | Gomis et al. | |
| 2009/0029378 A1 | 1/2009 | Connelly et al. | |
| 2009/0048117 A1 | 2/2009 | Glimcher et al. | |
| 2009/0220955 A1 | 9/2009 | Verrant | |
| 2010/0215743 A1 | 8/2010 | Leonard | |
| 2014/0057796 A1 | 2/2014 | Gomis et al. | |
| 2014/0105918 A1 | 4/2014 | Gomis et al. | |
| 2014/0162887 A1 | 6/2014 | Martin et al. | |
| 2014/0314792 A1 | 10/2014 | Gomis et al. | |
| 2015/0152506 A1 | 6/2015 | Gomis et al. | |
| 2015/0293100 A1 | 10/2015 | Gomis et al. | |
| 2015/0362495 A1 | 12/2015 | Gomis et al. | |
| 2016/0032399 A1 | 2/2016 | Gomis et al. | |
| 2016/0032400 A1 | 2/2016 | Gomis et al. | |
| 2016/0040247 A1 | 2/2016 | Gomis et al. | |
| 2017/0002357 A1 | 1/2017 | Gomis et al. | |
| 2017/0101683 A1 | 4/2017 | Gomis et al. | |
| 2017/0121777 A1 | 5/2017 | Gomis et al. | |
| 2017/0369589 A1 | 12/2017 | Gomis et al. | |
| 2017/0370935 A1 | 12/2017 | Gomis et al. | |
| 2019/0119757 A1 | 4/2019 | Gomis et al. | |
| 2019/0169693 A1 | 6/2019 | Gomis et al. | |
| 2019/0242898 A1 | 8/2019 | Gomis et al. | |
| 2019/0256922 A1 | 8/2019 | Gomis et al. | |
| 2019/0269707 A1 | 9/2019 | Gregory et al. | |

(Continued)

FOREIGN PATENT DOCUMENTS

| | | |
|---|---|---|
| CA | 2813674 A1 | 4/2012 |
| EP | 1256344 B1 | 12/2006 |
| EP | 1767541 A1 | 3/2007 |

(Continued)

OTHER PUBLICATIONS

Hering et al (Int Brz J Urol, 2003, 29(3): 228-233).*

(Continued)

*Primary Examiner* — Sean E Aeder

(74) *Attorney, Agent, or Firm* — Sterne, Kessler, Goldstein & Fox P.L.L.C.

(57) ABSTRACT

The present invention relates to a method for the diagnosis or the prognosis of metastasis, relapse or recurrence in prostate cancer which comprises determining if the c-MAF gene is amplified in a primary tumor sample. Likewise, the invention also relates to a method for the diagnosis or the prognosis of metastasis, relapse or recurrence in prostate cancer, as well as to a method for determining the tendency to develop bone metastasis with respect to metastasis in other organs, which comprise determining the c-MAF expression level. Finally, the invention relates to the use of a c-MAF inhibitor as therapeutic target for treating the prostate cancer.

11 Claims, 1 Drawing Sheet

Specification includes a Sequence Listing.

(56) References Cited

U.S. PATENT DOCUMENTS

2019/0309299 A1 10/2019 Gomis et al.

FOREIGN PATENT DOCUMENTS

| | | |
|---|---|---|
| EP | 2012128 A1 | 1/2009 |
| EP | 2626431 A2 | 8/2013 |
| ES | 2379918 A1 | 5/2012 |
| JP | 2006176542 A | 7/2006 |
| JP | 2007145715 A | 6/2007 |
| JP | 2007524671 A | 8/2007 |
| JP | 2012518686 A | 8/2012 |
| JP | 2016105731 A | 6/2016 |
| WO | WO-0055126 A2 | 9/2000 |
| WO | WO-0149288 A1 | 7/2001 |
| WO | WO-03020278 A1 | 3/2003 |
| WO | WO-03020721 A1 | 3/2003 |
| WO | WO-03059249 A2 | 7/2003 |
| WO | WO-2004000843 A1 | 12/2003 |
| WO | WO-2004014888 A1 | 2/2004 |
| WO | WO-2005026322 A2 | 3/2005 |
| WO | WO-2005046731 A1 | 5/2005 |
| WO | WO-2005063252 A1 | 7/2005 |
| WO | WO-2005070447 A2 | 8/2005 |
| WO | WO-2008098351 A1 | 8/2008 |
| WO | WO-2008104543 A2 | 9/2008 |
| WO | WO-2008142164 A2 | 11/2008 |
| WO | WO-2009049410 A1 | 4/2009 |
| WO | WO-2009146546 A1 | 12/2009 |
| WO | WO-2010099255 A1 | 9/2010 |
| WO | WO-2012045905 A2 | 4/2012 |
| WO | WO-2012115885 A1 | 8/2012 |
| WO | WO-2013153458 A2 | 10/2013 |
| WO | WO-2013182912 A2 | 12/2013 |
| WO | WO-2014057357 A2 | 4/2014 |
| WO | WO-2014140896 A2 | 9/2014 |
| WO | WO-2014140933 A2 | 9/2014 |
| WO | WO-2014184679 A2 | 11/2014 |
| WO | WO-2015052583 A2 | 4/2015 |
| WO | WO-2016092524 A1 | 6/2016 |
| WO | WO-2017203468 A1 | 11/2017 |
| WO | WO-2019102380 A1 | 5/2019 |

OTHER PUBLICATIONS

Abbott Molecular, "Vysis LSI IGH/MAF Dual Color Dual Fusion Probe," accessed at http://abbottmolecular.com/us/products/analyte-specific-reagent/fish/vysis-lsi-igh-maf-dual-color-dual-fusion-probe.html, accessed on Oct. 16, 2014, 2 pages.

Ablynx, "Annual Report 2010," ablynx.com, accessed at http://www.ablynx.com/uploads/pub/756d8eb9-e07c-4791-beaf-201caaa0d756-annual-report-2010.pdf, accessed on Nov. 4, 2015, 84 pages.

Abnova, "MAF FISH Probe," accessed at http://abnova.com/products/products_detail.asp?Catalog_id=FA0375, accessed on Oct. 16, 2014, 2 pages.

Afinitor.com, "AFINITOR (everolimus) Tablets," accessed at http://afinitor.com/sega-tuberous-sclerosis/patient/sega-information.jsp, accessed on Oct. 16, 2014, 5 pages.

Agilent Technologies, "Probes for Chromosome 16," accessed at http://genomics.agilent.com/productSearch.jsp?chr=16&start=79483700&end=79754340&_requestid=78075, accessed on Oct. 16, 2014, 3 pages.

Andrews, N.C., et al., "The Ubiquitous Subunit of Erythroid Transcription Factor NF-E2 is a Small Basic-leucine Zipper Protein Related to the v-maf Oncogene," Proceedings of the National Academy of Sciences of USA 90(24):11488-11492, National Academy of Sciences, United States (1993).

ARUP Laboratories, "Multiple Myeloma (MM) by FISH: Detection of Prognostically Significant Genomic Aberrations in Multiple Myeloma (MM) by Fluorescence in situ Hybridization (FISH)," accessed at http://aruplab.com, accessed on Oct. 16, 2014, 2 pages.

Baker, S.G., "The Central Role of Receiver Operating Characteristic (ROC) Curves in Evaluating Tests for the Early Detection of Cancer," Journal of the National Cancer Institute 95(7):511-515, Oxford University Press, England (2003).

Bogado, C.E., et al., "Denosumab: An Update," Drugs of Today 47(8):605-613, Prous Science, United States (2011).

Casset, F., et al., "A Peptide Mimetic of an Anti-CD4 Monoclonal Antibody by Rational Design," Biochemical and Biophysical Research Communications 307(1):198-205, Academic Press, United States (Jul. 2003).

CGI Italia, "IGH/MAF Two Color, Two Fusion Translocation Probe," accessed at http://cancergeneticsitalia.com/dna-fish-probe/ighmaf/, accessed on Oct. 16, 2014, 1 page.

Chen, L., et al., "Molecular Cytogenetic Aberrations in Patients with Multiple Myeloma Studied by Interphase Fluorescence in situ Hybridization," Experimental Oncology 29(2):116-120, Morion, Ukraine (2007).

Chen, Y., et al., "Selection and Analysis of an Optimized Anti-VEGF Antibody: Crystal Structure of an Affinity-matured Fab in Complex with Antigen," Journal of Molecular Biology 293(4):865-881, Academic Press, England (Nov. 1999).

Cher, M.L., et al., "Mapping of Regions of Physical Deletion on Chromosome 16q in Prostate Cancer Cells by Fluorescence in situ Hybridization (Fish)," the Journal of Urology 153(1):249-254, Elsevier, United States (1995).

Choi, M., et al., "Genetic Diagnosis by Whole Exome Capture and Massively Parallel DNA Sequencing," Proceedings of the National Academy of Sciences of USA 106(45):19096-19101, National Academy of Sciences, United States (2009).

Creative Bioarray, "Products," accessed at http://creative-bioarray.com/Products.htm, accessed on Oct. 16, 2014, 2 pages.

Cytocell, "Oncology and Constitutional FISH Probe Catalogue 2012/2013," accessed at http://zentech.be/uploads/docs/products_info/prenatalogy/cytocell%202012-2013%20catalogue%5B3%5D.pdf, accessed on Oct. 16, 2014, 134 pages.

Dako, "SureFISH Probes," accessed at http://dako.com/us/ar42/psg42806000/baseproducts_surefish.htm?setCountry=true&purl=ar42/psg42806000/baseproducts_surefish.htm?undefined&submit=Accept%20country, accessed on Oct. 16, 2014, 2 pages.

Dannhardt, G. And Kiefer, W., "Cyclooxygenase Inhibitors—Current Status and Future Prospects," European Journal of Medicinal Chemistry 36(2):109-126,Editions Scientifiques et Medicales Elsevier SAS, France (2001).

Demarest, J.F., et al., "Update on Aplaviroc: An HIV Entry Inhibitor Targeting CCR5," Retrovirology 2(Suppl 1):S13, BioMed Central, England (2005).

Denham, J.W., "An important piece of the localized prostate cancer puzzle?," Nature Reviews Clinical Oncology 8(10):573-574, Macmillan Publishers Limited, England (Oct. 2011).

Dhesy-Thind, S., et al., "Use of Adjuvant Bisphosphonates and Other Bone-Modifying Agents in Breast Cancer: A Cancer Care Ontario and American Society of Clinical Oncology Clinical Practice Guideline," J Clin Oncol 35, American Society of Clinical Oncology, United States, 22 pages (published online before print Mar. 6, 2017).

Ettenberg, S.A., et al., "BHQ880, A Novel Anti-DKK1 Neutralizing Antibody, Inhibits Tumor-Induced Osteolytic Bone Disease," Proceedings of the American Association for Cancer Resaerch 49:947, Abstract 3987, American Association for Cancer Research, United States (2008).

ExPASy Database, ENZYME entry EC 1.14.99.1, accessed on Oct. 16, 2014, accessed at http://enzyme.expasy.org/EC/1.14.99.1. ,1 page.

ExPASy Database, ENZYME entry EC 2.7.10.2, accessed on Oct. 16, 2014, accessed at http://enzyme.expasy.org/EC/2.7.10.2. 1 page.

ExPASy Database, ENZYME entry EC 2.7.11.1, accessed on Oct. 16, 2014, accessed at http://enzyme.expasy.org/EC/2.7.11.1. 1 page.

Eychene, A., et al., "A New MAFia in Cancer," Nature Reviews Cancer 8(9):683-693, Nature Publishing Group, England (2008).

Fili, S., et al., "Therapeutic Implications of Osteoprotegerin," Cancer Cell International 9:26:1-8, BioMed Central Ltd., England (2009).

(56) References Cited

OTHER PUBLICATIONS

Final Rejection dated May 9, 2017, in U.S. Appl. No. 14/435,128, Gomis, R., et al., § 371(c) Date: Apr. 10, 2015, 13 pages.
Fujiwara, K.T., et al., "Two New Members of the maf Oncogene Family, mafK and mafF, Encode Nuclear b-Zip Proteins Lacking Putative Trans-Activator Domain," Oncogene 8(9):2371-2380, Nature Publishing Group, England (1993).
GenBank Database, NCBI Reference Sequence NG_016440.1, accessed on Oct. 16, 2014, accessed at http://www.ncbi.nlm.nih.gov/protein/NG_016440.1., 2 pages.
GenBank Database, NCBI Reference Sequence NM_001031804.2, accessed on Oct. 16, 2014, accessed at http://www.ncbi.nlm.nih.gov/protein/NM_001031804.2. 2 pages.
GenBank Database, NCBI Reference Sequence NM_005360.4, accessed on Oct. 16, 2014, accessed at http://www.ncbi.nlm.nih.gov/protein/NM_005360.4 2 pages.
GenBank Database, NCBI Reference Sequence NP_001026974.1, accessed on Oct. 16, 2014, accessed at http://www.ncbi.nlm.nih.gov/protein/ NP_001026974.1. 2 pages.
GenBank Database, NCBI Reference Sequence NP_005351.2, accessed on Oct. 16, 2014, accessed at http://www.ncbi.nlm.nih.gov/protein/NP_005351.2. 2 pages.
GenBank Database, NCBI Reference Sequence NT_010498.15, accessed on Oct. 16, 2014, accessed at http://www.ncbi.nlm.nih.gov/nuccore/ NT_010498.15. 2 pages.
GenBank Database, NCBI Reference Sequence NT_010542.15, accessed on Oct. 16, 2014, accessed at http://www.ncbi.nlm.nih.gov/nuccore/ NT_010542.15. 2 pages.
Gene Annot Search, accessed at http://genecards.weizmann.ac.il/geneannot/GAsearch.pl?array=HG-U95&keyword type=genesymbol&keyword=maf%OD%0A&target=integrated&submit=Submit+Query, Maf, 2016, accessed Jan. 28, 2016, 2 pages.
GeneAnnot (http://genecards.weizmann.acil/cgi-bin/geneannott/GA_search.pl?array=HG-U95&keyword_type=gene_symbol&keyword=maf%0D%0A&target=integrated&.submit=Submit+Query, Maf, 2016). 2 pages.
Gentleman, R.C., et al., "Bioconductor: Open Software Development for Computational Biology and Bioinformatics," Genome Biology 5(10):R80, 16 pages, BioMed Central Ltd, England (2004).
Genycell Biotech, "FISH Mieloma Multiple," accessed at http://google.com/url?sa=t&rct=j&q=&esrc=s&source=web&cd=1&ved=CCQQFjAA&url=http%3A%2F%2Fwww.genycell.es%2Fimages%2Fproductos%2Fbrochures%2Flphmie6_86.ppt&ei=MhFYUOi3GKWH0QGlt4DoDw&usg=AFQjCNEqQMbT8vQGjJbi9riEf31VgoFTFQ&sig2=V5IS8juEMVHBI8Mv2Xx_Ww, accessed on Oct. 16, 2014, 1 page.
Glas, A.S., et al., "The diagnostic odds ratio: a single indicator of test performance," Journal of Clinical Epidemiology 56(11):1129-1135, Elsevier Inc., England (2003).
Hanbali, A., et al., "The Evolution of Prognostic Factors in Multiple Myeloma," in: Advances in Hematology 2017: Article ID 4812637, Retrieved from the Internet( URL: https://doi.org/10.1155/2017/4812637), 11 pages, Hindawi Publishing Corporation, United States (2017).
Hu, G., et al., "MTDH Activation by 8q22 Genomic Gain Promotes Chemoresistance and Metastasis of Poor-Prognosis Breast Cancer," Cancer Cell 15(1):9-20, Cell Press, United States (2009).
Hurt, E.M., et al., "Overexpression of c-maf is a Frequent Oncogenic Event in Multiple Myeloma that Promotes Proliferation and Pathological Interactions with Bone Marrow Stroma," Cancer Cell 5(2):191-199, Cell Press, United States (2004).
Igarashi, K., et al., "Activity and Expression of Murine Small Maf Family Protein MafK," The Journal of Biological Chemistry 270(13):7615-7624, The American Society for Biochemistry and Molecular Biology, Inc., United States (1995).
International Preliminary Report on Patentability for International Application No. PCT/IB2013/002866, European Patent Office, Rijswijk, Netherlands, dated Jan. 19, 2015, 27 pages.

International Search Report for International Application No. PCT/IB2013/002866, European Patent Office, Rijswijk, Netherlands, dated Apr. 1, 2014,6 pages.
Kataoka, K., et al., "Small Maf Proteins Heterodimerize with Fos and May Act as Competitive Repressors of the NF-E2 Transcription Factor," Molecular and Cellular Biology 15(4):2180-2190, American Society for Microbiology, United States (1995).
Kataoka, K., et al., "Transactivation Activity of Maf Nuclear Oncoprotein is Modulated by Jun, Fos and Small Maf Proteins," Oncogene 12:53-62, Stockton Press, England (1996).
Kaykas, A. and Moon, R.T., "A plasmid-based system for expressing small interfering RNA libraries in mammalian cells," BMC Cell Biology 5:1-11, BioMed Central Ltd., England (2004).
Kohler, G. and Milstein, C., "Continuous Cultures of Fused Cells Secreting Antibody of Predefined Specificity," Nature 256(5517):495-497, Macmillan Journals Ltd., England (Aug. 1975).
Kuritzkes, D.R., "HIV-1 Entry Inhibitors: An Overview," Current Opinion in HIV and AIDS 4(2):82-87, Lippincott Williams & Wilkins, United States (2009).
Lee, N.S., et al., "Expression of small interfering RNAs targeted against HIV-1 rev transcripts in human cells," Nature Biotechnology 20(5):500-505, Nature American Publishing, United States (2002).
Leica Biosystems, "KreatechTMFISH Probes," accessed at http://leicabiosystems.com/ihc-ish/kreatech-fish-probes/, accessed on Oct. 16, 2014, 2 pages.
Li, C., et al., "Distinct Deleted Regions on Chromosome Segment 16q23-24 Associated with Metastases in Prostate Cancer," Genes, Chromosomes and Cancer 24(3):175-182, Wiley-Liss, United States (1999).
Li, C., et al., "Gene Expression Biomarkers to Predict Overall Survival of Prostate Cancer Patients," Journal of Clinical Oncology 30(15):Abstract 4561, 2012 ASCO Annual Meeting Abstracts, American Society of Clinical Oncology, United States, 1 page (Jun. 2012).
Maccallum, R.M., et al., "Antibody-antigen Interactions: Contact Analysis and Binding Site Topography," Journal of Molecular Biology 262(5):732-745, Academic Press, England (Oct. 1996).
MetaSystems, "24XCyte," accessed at http://metasystems-international.com/index.php?option=com_joodb&view=article&joobase=5*id=12%3Ad-5029-100-og&Itemid=272, accessed on Oct. 16, 2014, 2 pages.
Miller, R.E., et al., "RANK Ligand Inhibition Plus Docetaxel Improves Survival and Reduces Tumor Burden in a Murine Model of Prostate Cancer Bone Metastasis," Molecular Cancer Therapeutics 7(7): 2160-2169, American Association for Cancer Research, United States (Jul. 2008).
National Cancer Institute, "Cabozantinib Shrinks Tumors and Bone Metastases in Prostate and Other Cancers," cancer.gov, accessed at https://wayback.archive-it.org/org-317/20110630103152/http://www.cancer.gov/ncicancerbulletin/053111/page3, accessed on Oct. 27, 2015, NCI Cancer Bulletin 8(11):1-4 (May 2011).
Ng, P.C. and Kirkness, E.F., "Whole Genome Sequencing," Methods in Molecular Biology 628:215-226, Springer Science+Business Media, LLC, Netherlands (2010).
Nguyen, D.X. and Massague, J., "Genetic Determinants of Cancer Metastasis," Nature Reviews Genetics 8(5):341-352, Nature Publishing Group, England (May 2007).
Nguyen, D.X., et al., "Metastasis: From Dissemination to Organ-Specific Colonization," Nature Reviews Cancer 9(4):274-284, Macmillan Publishers Limited, England (Apr. 2009).
Non-Final Rejection dated Nov. 21, 2017, in U.S. Appl. No. 14/435,128, Gomis, R., et al., § 371(c) Date: Apr. 10, 2015, 7 pages.
Non-Final Rejection dated Oct. 27, 2016, in U.S. Appl. No. 14/435,128, Gomis, R., et al., § 371(c) Date: Apr. 10, 2015, 15 pages.
Novartis Oncology, "About ZOMETA® (zoledronic acid) 4 mg/5mL Injection," accessed at http://us.zometa.com/index.jsp?usertrack.filter_aplied=true&NovaId=29353769344676336333, accessed on Oct. 16, 2014, 2 pages.
Office Action, Final Rejection, dated Mar. 12, 2018, in U.S. Appl. No. 15/183,419, Gomis R., et al., filed Jun. 15, 2016, 14 pages.

(56) References Cited

OTHER PUBLICATIONS

Morgan, T.M., et al., "Targeted Therapy for Advanced Prostate Cancer: Inhibition of the PI3K/AKT/mTOR Pathway," Current Cancer Drug Targets 9(2):237-249, Bentham Science Publishers, Netherlands (Mar. 2009).

Office Action dated Jul. 7, 2017, in U.S. Appl. No. 15/183,419, Gomis, R., et al., filed Jun. 15, 2016, 18 pages.

Khan, M.A., et al., "Bisphosphonates in Metastatic Prostate Cancer," Reviews in Urology 5(3):204-206, RIU Publishers, United States (2003).

Olmo, J.M.C., et al., "Efectividad y tolerabilidad del acid° zoledrOnico en el tratamiento del cancer de prostate metastásico," Actas Urologicas Espanolas 32(5):492-501, Asociación Española de Urología, Spain (2008).

Pageau, S.C., "Denosumab," Monoclonal Antibodies 1(3):210-215, Landes Bioscience, United States (2009).

Paik, S., et al., "A Multigene Assay to Predict Recurrence of Tamoxifen-Treated, Node-Negative Breast Cancer," The New England Journal of Medicine 351(27):2817-2826, Massachusetts Medical Society, United States (2004).

Papachristou, D.J., et al., "Bone Metastases: Molecular Mechanisms and Novel Therapeutic Interventions," Medicinal Research Reviews 32(3):611-636, Wiley Periodicals, Inc., United States (2012) (Published online 2010).

Polascik, T.J., "Bisphosphonates in Oncology: Evidence for the Prevention of Skeletal Events in Patients with Bone Metastases," Drug Design, Development and Therapy 3:27-40, Dove Medical Press Ltd., New Zealand (2009).

Pollack, J.R., et al., "Microarray Analysis Reveals a Major Direct Role of Dna Copy Number Alteration in the Transcriptional Program of Human Breast Tumors," Proceedings of the National Academy of Sciences of USA 99(20):12963-12968, National Academy of Sciences, United States (2002).

Ponten, F., et al., "A Global View of Protein Expression in Human Cells, Tissues, and Organs," Molecular Systems Biology 5:337, pp. 1-9, supplemental, Wiley Blackwell, England (2009).

Porter, A.T., and Mcewan, A.J., "Strontium-89 as an Adjuvant to External Beam Radiation Improves Pain Relief and Delays Disease Progression in Advanced Prostate Cancer: Results of a Randomized Controlled Trial," Seminars in Oncology 20(3 Suppl 2):38-43, W.B. Saunders, United States (1993).

Rotstein, D.M., et al., "Spiropiperidine CCR5 Antagonists," Bioorganic and Medicinal Chemistry Letters 19(18):5401-5406, Elsevier Ltd., England (2009).

Rudikoff, S., et al., "Single Amino Acid Substitution Altering Antigen-binding Specificity," Proceedings of the National Academy of Sciences of the United States of America 79(6):1979-1983, National Academy of Sciences, Washington (Mar. 1982).

Saylor, P.J., et al., "Emerging Therapies to Prevent Skeletal Morbidity in Men with Prostate Cancer," Journal of Clinical Oncology 29(27): 3705-3714, American Society of Clinical Oncology, United States (Sep. 2011).

Sen, B. and Johnson, F.M., "Regulation of SRC Family Kinases in Human Cancers," Journal of Signal Transduction 2011(865819):1-14, Hindawi Publishing Corporation, United States (Apr. 2011).

Sharad, S., et al., "Prostate Cancer Gene Expression Signature of Patients with High Body Mass Index," Prostate Cancer and Prostatic Diseases 14(1):22-29, Macmillan Publishers Limited, England (Mar. 2011).

Stanbrough, M., et al., "Increased Expression of Genes Converting Adrenal Androgens to Testosterone in Androgen-independent Prostate Cancer," Cancer Research 66(5):2815-2825, American Association for Cancer Research, United States (2006).

Sturge, J., et al., "Bone Metastasis in Prostate Cancer: Emerging Therapeutic Strategies," Nature Reviews Clinical Oncology 8(6):357-369, Macmillan Publishers Ltd., England (Jun. 2011).

Swennenhuis, J.F., et al., "Construction of Repeat-Free Fluorescence in situ Hybridization Probes," Nucleic Acids Research 40(3):e20:1-8, Oxford University Press, England (Feb. 2012).

The Human Protein Atlas, "Expression of MAF in prostate cancer—The Human Protein Atlas," www.proteinatlas.org, accessed at http://www.proteinatlas.org/ENSG00000178573-MAF/cancer/tissue/prostate+cancer, accessed on Jan. 12, 2016, 4 pages (pp. A through D).

Tran, N., et al., "Expressing functional siRNAs in mammalian cells using convergent transcription," BMC Biotechnology 3:21:1-9, BioMed Central Ltd., England (2003).

Vajdos, F.F., et al., "Comprehensive Functional Maps of the Antigen-binding Site of an Anti-Erbb2 Antibody Obtained with Shotgun Scanning Mutagenesis," Journal of Molecular Biology 320(2):415-428, Academic Press, England (Jul. 2002).

Velasco-Velazquez, M., et al., "CCR5 Antagonist Blocks Metastasis of Basal Breast Cancer Cells," Cancer Research 72(15):3839-3850, American Association for Cancer Research, United States (Aug. 2012).

Wagner, R.W., "Gene inhibition using antisense oligodeoxynucleotides," Nature 372(6504):333-335, Nature Publishing Group, England (1994).

Wang, J., et al., "Stable and controllable RNA interference: Investigating the physiological function of glutathionylated actin," Proceedings of the National Academy of Sciences of USA 100(9):5103-5106, National Academy of Sciences, United States (2003).

Watson, J.E., et al., "Integration of High-resolution Array Comparative Genomic Hybridization Analysis of Chromosome16q with Expression Array Data Refines Common Regions of Loss at 16q23-qter and Identifies Underlying Candidate Tumor Suppressor Genes in Prostate Cancer," Oncogene 23(19):3487-3494, Nature Publishing Group, England (Apr. 2004).

Welsh, J.B., et al., "Analysis of Gene Expression Identifies Candidate Markers and Pharmacological Targets in Prostate Cancer," Cancer Research 61(16):5974-5978, American Association for Cancer Research, United States (2001).

Yap, T.A., et al., "The Changing Therapeutic Landscape of Castration-resistant Prostate Cancer," Nature Reviews Clinical Oncology 8(10):597-610, Macmillan Publishers Limited, England (Aug. 2011).

Zaug, A.J., et al., "A Labile Phosphodiester Bond at the Ligation Junction in a Circular Intervening Sequence RNA," Science 224(4649):574-578, American Association for the Advancement of Science, United States (1984).

Zeiss, "FISH Probes: XL Haematology," accessed at https://microshop.zeiss.com/?440675675dedc6&1=en&p=uk&f=r&i=5000&o=&h=25&n=1&sd=000000-528-231-uk, accessed on Oct. 16, 2014, 3 pages.

Zheng, L., et al., "An approach to genomewide screens of expressed small interfering RNAs in mammalian cells," Proceedings of the National Academy of Sciences of USA 101(1):135-140, National Academy of Sciences, United States (2004).

Zhou, H., et al., "Updates of mTOR Inhibitors," Anticancer Agents in Medicinal Chemistry 10(7):571-581, Bentham Science Publishers, Netherlands (2010).

Co-pending Application, U.S. Appl. No. 15/944,499, Inventors Gomis, R., et al., filed Apr. 3, 2018 (Not Published).

Co-pending Application, U.S. Appl. No. 15/944,510, Inventors Gomis, R., et al., filed Apr. 3, 2018 (Not Published).

Co-pending Application, U.S. Appl. No. 15/955,790, Inventors Gomis, R., et al., filed Apr. 18, 2018 (Not Published).

Co-pending Application, U.S. Appl. No. 16/134,449, Inventors Gomis, R., et al., filed Sep. 18, 2018 (Not Published).

Co-pending Application, U.S. Appl. No. 16/028,530, inventor Gomis, et al., filed Jul. 6, 2018 (Not Published).

Co-pending Application, U.S. Appl. No. 16/303,945, inventor Gomis, et al., filed Nov. 21, 2018 (Not Published).

Armstrong, A.J., et al., "Biomarkers in the Management and Treatment of Men With Metastatic Castration-resistant Prostate Cancer," European Urology 61(3):549-559, Elsevier Science, Switzerland (Mar. 2012).

Gherardi, E., et al., "Targeting MET in Cancer: Rationale and Progress," Nature Reviews Cancer 12(2):89-103, Nature Publishing Group, England (Feb. 2012).

Co-pending Application, U.S. Appl. No. 16/766,043, inventors Gregory, W.M., et al., § 371 (c) Date: May 21, 2020 (Not Yet Published).

(56) References Cited

OTHER PUBLICATIONS

Co-pending Application, U.S. Appl. No. 17/108,390, inventors Gomis, R., et al., filed Dec. 1, 2020 (Not Yet Published).

* cited by examiner

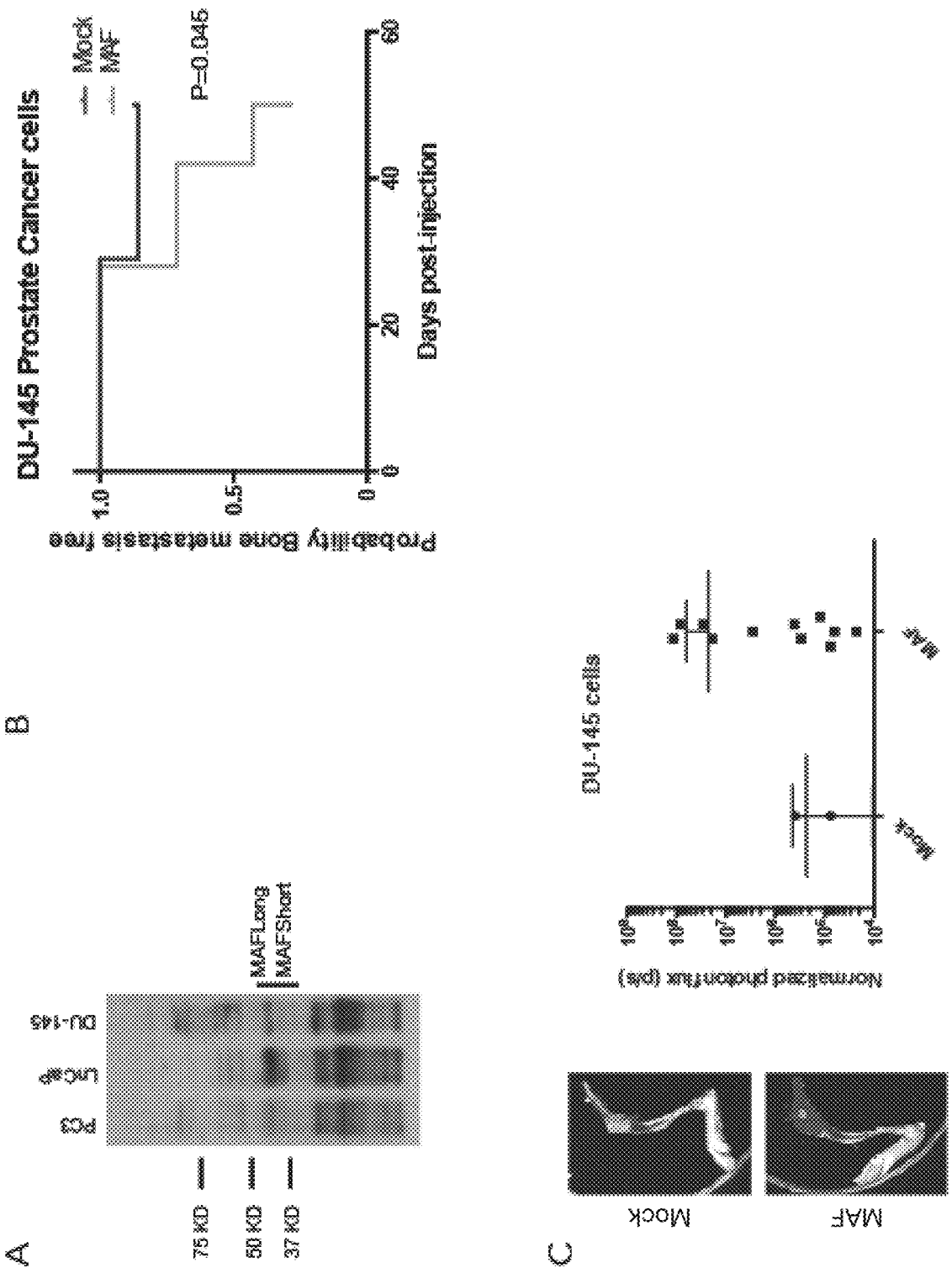

SEQUENCE LISTING

<160> NUMBER OF SEQ ID NOS: 24

<210> SEQ ID NO 1
<211> LENGTH: 6878
<212> TYPE: DNA
<213> ORGANISM: Homo sapiens

<400> SEQUENCE: 1

```
agaggcttta aaatctttt  tcatcttcta gctgtagctc gggctgcttg tcggcttggc      60
ctcccctcc  cccctttgct ctctgcctcg tctttcccca ggacttcgct attttgcttt     120
tttaaaaaaa ggcaagaaag aactaaactc cccctccct  ctcctccagt cgggctgcac     180
ctctgccttg cactttgcac agaggtagag agcgcgcgag ggagagagag gaaagaaaaa     240
aaataataaa gagagccaag cagaagagga ggcgagaagc atgaagtgtt aactcccccg     300
tgccaaggcc cgcgccgccc ggacagacgc ccgccgcgcc tccagccccg agcggacgcc     360
gcgcgcgccc tgcctgcagc ccgggccggc gaggcgagcc cttccttatg caaagcgcgc     420
agcggagcgg cgagcggggg acgccgcgca ccgggccggg ctcctccagc ttcgccgccg     480
cagccaccac cgccgccacc gcagctcgcg gaggatcttc ccgagcctga agccgccggc     540
tcggcgcgca aggaggcgag cgagcaagga ggggccgggg cgagcgaggg agcacattgg     600
cgtgagcagg ggggagggag ggcgggcgcg gggggcgcgg gcagggcggg ggggtgtgtg     660
tgtgagcgcg ctcggaggtt tcgggccagc caccgccgcg caagctagaa gcgcccagc     720
ccggcaagct ggctcacccg ctggccaccc agcacagccc gctggcccct ctcctgcagc     780
ccatctggcg gagcggcggc ggcggcggcg gcggcggcag gagaatggca tcagaactgg     840
caatgagcaa ctccgacctg cccaccagtc ccctggccat ggaatatgtt aatgacttcg     900
atctgatgaa gtttgaagtg aaaaaggaac cggtggagac cgaccgcatc atcagccagt     960
gcggccgtct catcgccggg ggctcgctgt cctccacccc catgagcacg ccgtgcagct    1020
cggtgccccc ttcccccagc ttctcggcgc ccagcccggg ctcgggcagc gagcagaagg    1080
cgcacctgga agactactac tggatgaccg gctaccgca  gcagctgaac cccgaggcgc    1140
tgggcttcag ccccgaggac gcggtcgagg cgctcatcag caacagccac cagctccagg    1200
gcggcttcga tggctacgcg cgcggggcgc agcagctggc cgcggcggcc ggggccggtg    1260
ccggcgcctc cttgggcggc agcggcgagg agatgggccc cgccgccgcc gtggtgtccg    1320
ccgtgatcgc cgcggccgcc gcgcagagcg gcgcgggccc gcactaccac caccaccacc    1380
accacgccgc cggccaccac caccacccga cggccggcgc gcccggcgcc gcgggcagcg    1440
cggccgcctc ggccggtggc gctggggcg  cgggcggcgg tggcccggcc agcgctgggg    1500
gcggcggcgg cggcggcggc ggcggaggcg gcgggggcgc ggcgggggcg ggggcgccc     1560
tgcacccgca ccacgccgcc ggcggcctgc acttcgacga ccgcttctcc gacgagcagc    1620
tggtgaccat gtctgtgcgc gagctgaacc ggcagctgcg cggggtcagc aaggaggagg    1680
tgatccggct gaagcagaag aggcggaccc tgaaaaaccg cggctatgcc cagtcctgcc    1740
gcttcaagag ggtgcagcag agacacgtcc tggagtcgga gaagaaccag ctgctgcagc    1800
```

```
aagtcgacca cctcaagcag gagatctcca ggctggtgcg cgagagggac gcgtacaagg    1860
agaaatacga gaagttggtg agcagcggct tccgagaaaa cggctcgagc agcgacaacc    1920
cgtcctctcc cgagtttttc atgtgagtct gacacgcgat tccagctagc caccctgata    1980
agtgctccgc gggggtccgg ctcggtgtg ggcttgctag ttctagagcc atgctcgcca     2040
ccacctcacc accccacco ccaccgagtt tggcccccett ggcccctac acacacacaa    2100 acccgcacgc acacaccaca cacacacaca cacacacaca cacacccac accctgctcg   2160 agtttgtggt ggtggtggct gttttaaact ggggagggaa tgggtgtctg gctcatggat   2220
tgccaatctg aaattctcca taacttgcta gcttgttttt tttttttttt tacaccccccc 2280 cgccccaccc ccggacttgc acaatgttca atgatctcag cagagttctt catgtgaaac  2340
gttgatcacc tttgaagcct gcatcattca catattttt cttcttcttc cccttcagtt   2400
catgaactgg tgttcatttt ctgtgtgtgt gtgtgtttta ttttgtttgg atttttttt   2460 ttaattttac ttttagagct tgctgtgttg cccaccttt ttccaacctc caccctcact   2520
ccttctcaac ccatctcttc cgagatgaaa gaaaaaaaaa agcaaagttt ttttttcttc  2580
tcctgagttc ttcatgtgag attgagcttg caaaggaaaa aaaatgtga aatgttatag   2640 acttgcagcg tgccgagttc catcgggttt ttttttagc attgttatgc taaaatagag   2700
aaaaaaatcc tcatgaacct tccacaatca agcctgcatc aaccttctgg gtgtgacttg  2760
tgagttttgg ccttgtgatg ccaaatctga gagtttagtc tgccattaaa aaaactcatt  2820
ctcatctcat gcattattat gcttgctact ttgtcttagc aacaatgaac tataactgtt  2880
tcaaagactt tatggaaaag agacattata ttaataaaaa aaaaaagcct gcatgctgga  2940
catgtatggt ataattattt tttcctttt ttttccttt ggcttggaaa tggacgttcg   3000
aagacttata gcatggcatt catacttttg tttattgcc tcatgactt tttgagttta    3060 gaacaaaaca gtgcaaccgt agagccttct tcccatgaaa ttttgcatct gctccaaaac  3120
tgctttgagt tactcagaac ttcaacctcc caatgcactg aaggcattcc ttgtcaaaga  3180
taccagaatg ggttacacat ttaacctggc aaacattgaa gaactcttaa tgttttcttt  3240
ttaataagaa tgacgcccca ctttggggac taaaattgtg ctattgccga gaagcagtct  3300
aaaatttatt ttttaaaaag agaaactgcc ccattatttt tggtttgttt tattttatt   3360 ttatattttt tggcttttgg tcattgtcaa atgtggaatg ctctgggttt ctagtatata  3420
atttaattct agttttata atctgttagc ccagttaaaa tgtatgctac agataaagga  3480
atgttataga taaatttgaa agagttaggt ctgtttagct gtagattttt taaacgattg  3540
atgcactaaa ttgtttacta ttgtgatgtt aaggggggta gagtttgcaa ggggactgtt  3600 taaaaaagt agcttataca gcatgtgctt gcaacttaaa tataagttgg gtatgtgtag  3660
tctttgctat accactgact gtattgaaaa ccaaagtatt aagagggga acgcccctgt   3720 ttatatctgt aggggtattt tacattcaaa aatgtatgtt ttttttcctt ttcaaaatta  3780
aagtatttgg gactgaattg cactaagata taacctgcaa gcatataata caaaaaaaaa  3840
ttgcaaaact gtttagaacg ctaataaaat ttatgcagtt ataaaatgg cattactgca   3900 cagtttaag atgatgcaga tttttttaca gttgtattgt ggtgcagaac tggatttct    3960 gtaacttaaa aaaaaatcca cagttttaaa ggcaataatc agtaaatgtt attttcaggg  4020
actgacatcc tgtctttaaa aagaaatgaa aagtaaatct taccacaata aatataaaaa  4080
aatcttgtca gttactttc ttttacatat ttgctgtgc aaaattgttt tatatcttga    4140
gttactaact aaccacgcgt gttgttccta tgtgcttttc tttcatttc aattctggtt   4200
```

| | |
|---|---|
| atatcaagaa aagaataatc tacaataata aacggcattt ttttttgatt ctgtactcag | 4260 |
| tttcttagtg tacagtttaa ctgggcccaa caacctcgtt aaaagtgtaa aatgcatcct | 4320 |
| tttctccagt ggaaggattc ctggaggaat agggagacag taattcaggg tgaaattata | 4380 |
| ggctgttttt tgaagtgagg aggctggccc catatactga ttagcaatat ttaatataga | 4440 |
| tgtaaattat gacctcattt ttttctcccc aaagttttca gttttcaaat gagttgagcc | 4500 |
| ataattgccc ttggtaggaa aaacaaaaca aaacagtgga actaggcttc ctgagcatgg | 4560 |
| ccctacactt ctgatcagga gcaaagccat ccatagacag aggagccgga caaatatggc | 4620 |
| gcatcagagg tggcttgcgc acatatgcat tgaacggtaa agagaaacag cgcttgcctt | 4680 |
| ttcactaaag ttgactattt ttccttcttc tcttacacac cgagattttc ttgttagcaa | 4740 |
| ggcctgacaa gatttaacat aaacatgaca aatcatagtt gtttgttttg ttttgctttt | 4800 |
| ctctttaaca ctgaagatca tttgtcttaa ataggaaaaa gaaaatccac tccttacttc | 4860 |
| catatttcca agtacatatc tggtttaaac tatgttatca aatcatattt caccgtgaat | 4920 |
| attcagtgga gaacttctct acctggatga gctagtaatg atttcagatc atgctatccc | 4980 |
| cagaaataaa agcaaaaaat aatacctgtg tggaatatag gctgtgcttt gatttactgg | 5040 |
| tatttacccc aaaataggct gtgtatgggg gctgacttaa agatcccttg gaaagactca | 5100 |
| aaactacctt cactagtagg actcctaagc gctgacctat ttttaaatga cacaaattca | 5160 |
| tgaaactaat gttacaaatt catgcagttt gcactcttag tcatcttccc ctagcacacc | 5220 |
| aatagaatgt tagacaaagc cagcactgtt ttgaaaatac agccaaacac gatgactttt | 5280 |
| gttttgtttt ctgccgttct taaaagaaaa aaagataata ttgcaactct gactgaaaga | 5340 |
| cttattttta agaaaacagg ttgtgtttgg tgctgctaag ttctggccag tttatcatct | 5400 |
| ggccttcctg cctatttttt acaaaacacg aagacagtgt gtaacctcga cattttgacc | 5460 |
| ttcctttatg tgctagttta gacaggctcc tgaatccaca cttaattttg cttaacaaaa | 5520 |
| gtcttaatag taaacctccc ctcatgagct tgaagtcaag tgttcttgac ttcagatatt | 5580 |
| tctttccttt tttttttttt ttcctcatca caactaagag atacacaaac tctgaagaag | 5640 |
| cagaaatgga gagaatgctt ttaacaaaaa agcatctgat gaaagatttt aggcaaacat | 5700 |
| tctcaaaata agagtgatat tctggatgta gttattgcag ttatctcatg acaaatgagg | 5760 |
| cctggattgg aaggaaaata tagttgtgta gaattaagca ttttgatagg aatctacaag | 5820 |
| gtagttgaat ataataagca ggtttgggcc cccaaacttt agaaaatcaa atgcaaaggt | 5880 |
| gctggcaaaa atgaggtttg agtggctggc tgtaagagaa ggttaactcc tagtaaaagg | 5940 |
| cattttaga aataacaatt actgaaaact ttgaagtata gtgggagtag caaacaaata | 6000 |
| catgtttttt ttttcttaca aagaactcct aaatcctgag taagtgccat tcattacaat | 6060 |
| aagtctctaa atttaaaaaa aaaaaaatca tatgaggaaa tctagctttc ccctttacgc | 6120 |
| tgcgtttgat ctttgtctaa atagtgttaa aattcctttc attccaatta cagaactgag | 6180 |
| cccactcgca agttggagcc atcagtggga tacgccacat tttggaagcc ccagcatcgt | 6240 |
| gtacttacca gtgtgttcac aaaatgaaat ttgtgtgaga gctgtacatt aaaaaaaatc | 6300 |
| atcattatta ttattatttg cagtcatgga gaaccaccta cccctgactt ctgtttagtc | 6360 |
| tccttttaa ataaaaatta ctgtgttaga gaagaaggct attaaatgta gtagttaact | 6420 |
| atgcctcttg tctgggggtt tcatagagac cggtaggaaa gcgcactcct gcttttcgat | 6480 |
| ttatggtgtg tgcaagtaaa caggtgcatt gctttcaacc tgccatacta gttttaaaaa | 6540 |

| | |
|---|---|
| ttcactgaaa ttacaaagat acatatatat gcatatatat aatggaaagt ttcccggaat | 6600 |
| gcaacaatta gcatttttaaa atcatatata ggcatgcaca ttctaaatag tacttttttca | 6660 |
| tgcttcattg tttctctggc agataatttt actaagaaga aaaatagata ttcgactccc | 6720 |
| cttccctaaa caaatccacg ggcagaggct ccagcgagc cgagccccct ggttttctcg | 6780 |
| taggccctag acggtgttgc atttatcagt gatgtcaaac gtgctcattt gtcagacata | 6840 |
| gctgtaaatg aaaacaatgt gtggcaaaat acaaagtt | 6878 |

<210> SEQ ID NO 2
<211> LENGTH: 2656
<212> TYPE: DNA
<213> ORGANISM: Homo sapiens

<400> SEQUENCE: 2

| | |
|---|---|
| gaggctttaa aatcttttttt catcttctag ctgtagctcg ggctgcttgt cggcttggcc | 60 |
| tcccctccc cccttttgctc tctgcctcgt cttcccccag gacttcgcta ttttgctttt | 120 |
| ttaaaaaaag gcaagaaaga actaaactcc cccctccctc tcctccagtc gggctgcacc | 180 |
| tctgccttgc actttgcaca gaggtagaga gcgcgcgagg gagagagagg aaagaaaaaa | 240 |
| aataataaag agagccaagc agaagaggag gcgagaagca tgaagtgtta actcccccgt | 300 |
| gccaaggccc gcgccgcccg gacagacgcc cgccgcgcct ccagccccga gcggacgccg | 360 |
| cgcgcgccct gcctgcagcc cgggccggcg aggcgagccc ttccttatgc aaagcgcgca | 420 |
| gcggagcggc gagcggggga cgccgcgcac cgggccgggc tcctccagct tcgccgccgc | 480 |
| agccaccacc gccgccaccg cagctcgcgg aggatcttcc cgagcctgaa gccgccggct | 540 |
| cggcgcgcaa ggaggcgagc gagcaaggag gggccggggc gagcgaggga gcacattggc | 600 |
| gtgagcaggg gggagggagg gcgggcgcgg ggggcgcggg cagggcgggg gggtgtgtgt | 660 |
| gtgagcgcgc tcggaggttt cgggccagcc accgccgcgc aagctagaag cgccccagcc | 720 |
| cggcaagctg gctcacccgc tggccaccca gcacagcccg ctggcccctc tcctgcagcc | 780 |
| catctggcgg agcggcggcg gcggcggcgg cggcggcagg agaatggcat cagaactggc | 840 |
| aatgagcaac tccgacctgc ccaccagtcc cctggccatg gaatatgtta atgacttcga | 900 |
| tctgatgaag tttgaagtga aaaaggaacc ggtggagacc gaccgcatca tcagccagtg | 960 |
| cggccgtctc atcgcggggg gctcgctgtc ctccaccccc atgagcacgc cgtgcagctc | 1020 |
| ggtgccccct tcccccagct tctcggcgcc cagcccgggc tcgggcagcg agcagaaggc | 1080 |
| gcacctggaa gactactact ggatgaccgg ctaccccgcag cagctgaacc ccgaggcgct | 1140 |
| gggcttcagc cccgaggacg cggtcgaggc gctcatcagc aacagccacc agctccaggg | 1200 |
| cggcttcgat ggctacgcgc gcggggcgca gcagctggcc gcggcggccg gggccggtgc | 1260 |
| cggcgcctcc ttgggcggca gcggcgagga gatgggcccc gccgccgccg tggtgtccgc | 1320 |
| cgtgatcgcc gcggccgccg cgcagagcgg cgcgggcccg cactaccacc accaccacca | 1380 |
| ccacgccgcc ggccaccacc accacccgac ggccggcgcg cccggcgccg cgggcagcgc | 1440 |
| ggccgcctcg gccggtggcg ctggggggcg gggcggcggt ggcccggcca gcgctggggg | 1500 |
| cggcggcggc ggcggcggcg gcgaggcgg cggggggcgcg gcggggggcgg ggggcgccct | 1560 |
| gcacccgcac cacgccgccg gcggcctgca cttcgacgac cgcttctccg acgagcagct | 1620 |
| ggtgaccatg tctgtgcgcg agctgaaccg gcagctgcgc ggggtcagca aggaggaggt | 1680 |
| gatccggctc aagcagaaga ggcggaccct gaaaaaccgc ggctatgccc agtcctgccg | 1740 |
| cttcaagagg gtgcagcaga gacacgtcct ggagtcggag aagaaccagc tgctgcagca | 1800 |

-continued

```
agtcgaccac ctcaagcagg agatctccag gctggtgcgc gagagggacg cgtacaagga    1860
gaaatacgag aagttggtga gcagcggctt ccgagaaaac ggctcgagca gcgacaaccc    1920
gtcctctccc gagttttcca taactgagcc cactcgcaag ttggagccat cagtgggata    1980
cgccacattt tggaagcccc agcatcgtgt acttaccagt gtgttcacaa aatgaaattt    2040
gtgtgagagc tgtacattaa aaaaaatcat cattattatt attatttgca gtcatggaga    2100
accacctacc cctgacttct gtttagtctc cttttttaaat aaaaattact gtgttagaga    2160
agaaggctat taaatgtagt agttaactat gcctcttgtc tgggggtttc atagagaccg    2220
gtaggaaagc gcactcctgc ttttcgattt atggtgtgtg caagtaaaca ggtgcattgc    2280
tttcaacctg ccatactagt tttaaaaatt cactgaaatt acaagatac atatatatgc    2340
atatatataa tggaaagttt cccggaatgc aacaattagc attttaaaat catatatagg    2400
catgcacatt ctaaatagta cttttttcatg cttcattgtt tctctggcag ataattttac    2460
taagaagaaa aatagatatt cgactcccct tccctaaaca aatccacggg cagaggctcc    2520
agcggagccg agcccctggg ttttctcgta ggccctagac ggtgttgcat ttatcagtga    2580
tgtcaaacgt gctcatttgt cagacatagc tgtaaatgaa acaatgtgt ggcaaaatac    2640
aaagttaaaa aaaaaa                                                    2656
```

<210> SEQ ID NO 3
<211> LENGTH: 6887
<212> TYPE: DNA
<213> ORGANISM: Homo sapiens

<400> SEQUENCE: 3

```
gaggctttaa aatcttttttt catcttctag ctgtagctcg ggctgcttgt cggcttggcc      60
tccccctccc cccctttgctc tctgcctcgt cttttccccag gacttcgcta ttttgctttt     120
ttaaaaaaag gcaagaaaga actaaactcc ccctccctc tcctccagtc gggctgcacc       180
tctgccttgc actttgcaca gaggtagaga gcgcgcgagg gagagagagg aaagaaaaaa     240
aataataaag agagccaagc agaagaggag gcgagaagca tgaagtgtta actccccgt       300
gccaaggccc gcgccgcccg gacagacgcc cgccgcgcct ccagccccga gcggacgccg     360
cgcgcgccct gcctgcagcc cgggccggcg aggcgagccc ttccttatgc aaagcgcgca     420
gcggagcggc gagcggggga cgccgcgcac cgggccgggc cctccagct tcgccgccgc      480
agccaccacc gccgccaccg cagctcgcgg aggatcttcc cgagcctgaa gccgccggct     540
cggcgcgcaa ggaggcgagc gagcaaggag gggccggggc gagcgaggga gcacattggc     600
gtgagcaggg gggagggagg gcgggcgcgg ggggcgcggg cagggcgggg gggtgtgtgt    660
gtgagcgcgc tcgaggttt cgggccagcc accgccgcgc aagctagaag cgccccagcc     720
cggcaagctg gctcacccgc tggccaccca gcacagcccg ctggcccctc tcctgcagcc     780
catctggcgg agcggcggcg gcggcggcgg cggcggcagg agaatggcat cagaactggc     840
aatgagcaac tccgacctgc ccaccagtcc cctggccatg gaatatgtta atgacttcga     900
tctgatgaag tttgaagtga aaaggaacc ggtggagacc gaccgcatca tcagccagtg     960
cggccgtctc atcgccgggg gctcgctgtc ctccacccc atgagcacgc cgtgcagctc    1020
ggtgcccccct tccccagct tctcggcgcc cagcccggc tcgggcagcg agcagaaggc    1080
gcacctggaa gactactact ggatgaccgg ctacccgcag cagctgaacc ccgaggcgct    1140
gggcttcagc cccgaggacg cggtcgaggc gctcatcagc aacagccacc agctccaggg    1200
```

```
cggcttcgat ggctacgcgc gcggggcgca gcagctggcc gcggcggccg gggccggtgc    1260
cggcgcctcc ttgggcggca gcggcgagga gatgggcccc gccgccgccg tggtgtccgc    1320
cgtgatcgcc gcggccgccg cgcagagcgg cgcgggcccg cactaccacc accaccacca    1380
ccacgccgcc ggccaccacc acccccgac ggccggcgcg cccggcgccg cgggcagcgc    1440
ggccgcctcg gccggtggcg ctggggcgc gggcggcggt ggcccggcca gcgctggggg    1500
cggcggcggc ggcggcggcg gcggaggcgg cgggggcgcg gcggggcgg ggggcgccct    1560 gcacccgcac cacgccgccg gcggcctgca cttcgacgac cgcttctccg acgagcagct    1620
ggtgaccatg tctgtgcgcg agctgaaccg gcagctgcgc ggggtcagca aggaggaggt    1680
gatccggctg aagcagaaga ggcggaccct gaaaaaccgc ggctatgccc agtcctgccg    1740
cttcaagagg gtgcagcaga gacacgtcct ggagtcggag aagaaccagc tgctgcagca    1800
agtcgaccac ctcaagcagg agatctccag gctggtgcgc gagagggacg cgtacaagga    1860
gaaatacgag aagttggtga gcagcggctt ccgagaaaac ggctcgagca gcgacaaccc    1920
gtcctctccc gagttttca tgtgagtctg acacgcgatt ccagctagcc accctgataa    1980
gtgctccgcg ggggtccggc tcgggtgtgg gcttgctagt tctagagcca tgctcgccac    2040
cacctcacca ccccaccccc caccgagttt ggccccttg gccccctaca cacacacaaa    2100
cccgcacgca cacaccacac acacacacac acacacacac acaccccaca ccctgctcga    2160
gtttgtggtg gtggtggctg ttttaaactg gggagggaat gggtgtctgg ctcatggatt    2220
gccaatctga aattctccat aacttgctag cttgttttt tttttttttt acacccccc    2280 gccccacccc cggacttgca caatgttcaa tgatctcagc agagttcttc atgtgaaacg    2340
ttgatcacct ttgaagcctg catcattcac atatttttc ttcttcttcc ccttcagttc    2400
atgaactggt gttcatttc tgtgtgtgtg tgtgttttat tttgtttgga tttttttttt    2460
taattttact tttagagctt gctgtgttgc ccaccttttt tccaacctcc accctcactc    2520
cttctcaacc catctcttcc gagatgaaag aaaaaaaaaa gcaaagtttt tttttcttct    2580
cctgagttct tcatgtgaga ttgagcttgc aaaggaaaaa aaaatgtgaa atgttataga    2640
cttgcagcgt gccgagttcc atcgggtttt tttttagca ttgttatgct aaaatagaga    2700
aaaaaatcct catgaacctt ccacaatcaa gcctgcatca accttctggg tgtgacttgt    2760
gagttttggc cttgtgatgc caaatctgag agtttagtct gccattaaaa aaactcattc    2820
tcatctcatg cattattatg cttgctactt tgtcttagca acaatgaact ataactgttt    2880
caaagacttt atgaaaaaga gacattatat taataaaaaa aaaaagcctg catgctggac    2940
atgtatggta taattatttt ttcctttttt tttcctttg gcttggaaat ggacgttcga    3000
agacttatag catggcattc atactttgt tttattgcct catgactttt ttgagtttag    3060
aacaaaacag tgcaaccgta gagccttctt cccatgaaat tttgcatctg ctccaaaact    3120
gctttgagtt actcagaact tcaacctccc aatgcactga aggcattcct tgtcaaagat    3180
accagaatgg gttacacatt taacctggca aacattgaag aactcttaat gttttctttt    3240
taataagaat gacgccccac tttggggact aaaattgtgc tattgccgag aagcagtcta    3300
aaatttattt tttaaaaga gaaactgccc cattattttt ggtttgtttt attttttatt    3360 tatattttt ggcttttggt cattgtcaaa tgtggaatgc tctgggtttc tagtatataa    3420
tttaattcta gtttttataa tctgttagcc cagttaaaat gtatgctaca gataaaggaa    3480
tgttatagat aaatttgaaa gagttaggtc tgtttagctg tagattttt aaacgattga    3540 tgcactaaat tgtttactat tgtgatgtta aggggggtag agtttgcaag gggactgttt    3600
```

```
aaaaaaagta gcttatacag catgtgcttg caacttaaat ataagttggg tatgtgtagt    3660
ctttgctata ccactgactg tattgaaaac caaagtatta agaggggaaa cgcccctgtt    3720
tatatctgta ggggtatttt acattcaaaa atgtatgttt ttttttcttt tcaaaattaa    3780
agtatttggg actgaattgc actaagatat aacctgcaag catataatac aaaaaaaaat    3840
tgcaaaactg tttagaacgc taataaaatt tatgcagtta taaaaatggc attactgcac    3900
agttttaaga tgatgcagat ttttttacag ttgtattgtg gtgcagaact ggattttctg    3960
taacttaaaa aaaatccac  agttttaaag gcaataatca gtaaatgtta ttttcaggga    4020
ctgacatcct gtctttaaaa agaaatgaaa agtaaatctt accacaataa atataaaaaa    4080
atcttgtcag ttacttttct tttacatatt ttgctgtgca aaattgtttt atatcttgag    4140
ttactaacta accacgcgtg ttgttcctat gtgcttttct ttcattttca attctggtta    4200
tatcaagaaa agaataatct acaataataa acggcatttt ttttttgattc tgtactcagt    4260 ttcttagtgt acagtttaac tgggcccaac aacctcgtta aaagtgtaaa atgcatcctt    4320
ttctccagtg gaaggattcc tggaggaata gggagacagt aattcagggt gaaattatag    4380
gctgtttttt gaagtgagga ggctggcccc atatactgat tagcaatatt taatatagat    4440
gtaaattatg acctcatttt tttctcccca aagttttcag ttttcaaatg agttgagcca    4500
taattgccct tggtaggaaa acaaaacaa  aacagtggaa ctaggcttcc tgagcatggc    4560
cctacacttc tgatcaggag caaagccatc catagacaga ggagccggac aaatatggcg    4620
catcagaggg ggcttgcgca catatgcatt gaacggtaaa gagaaacagc gcttgccttt    4680
tcactaaagt tgactatttt tccttcttct cttacacacc gagattttct tgttagcaag    4740
gcctgacaag atttaacata aacatgacaa atcatagttg tttgttttgt tttgctttc    4800 tctttaacac tgaagatcat ttgtcttaaa taggaaaaag aaaatccact ccttacttcc    4860
atatttccaa gtacatatct ggtttaaact atgttatcaa atcatatttc accgtgaata    4920
ttcagtggag aacttctcta cctggatgag ctagtaatga tttcagatca tgctatcccc    4980
agaaataaaa gcaaaaaata atacctgtgt ggaatatagg ctgtgctttg atttactggt    5040 attttaccccca aaataggctg tgtatggggg ctgacttaaa gatcccttgg aaagactcaa    5100
aactaccttc actagtagga ctcctaagcg ctgacctatt tttaaatgac acaaattcat    5160
gaaactaatg ttacaaattc atgcagtttg cactcttagt catcttcccc tagcacacca    5220
atagaatgtt agacaaagcc agcactgttt tgaaaataca gccaaacacg atgacttttg    5280
ttttgttttc tgccgttctt aaaagaaaaa agatatatat tgcaactctg actgaaagac    5340
ttatttttaa gaaaacaggt tgtgtttggt gctgctaagt tctggccagt ttatcatctg    5400
gccttcctgc ctattttta  caaaacacga agacagtgtg taacctcgac attttgacct    5460
tcctttatgt gctagtttag acaggctcct gaatccacac ttaattttgc ttaacaaaag    5520
tcttaatagt aaacctcccc tcatgagctt gaagtcaagt gttcttgact tcagatattt    5580
cttttccttt tttttttttt tcctcatcac aactaagaga tacacaaact ctgaagaagc    5640
agaaatggag agaatgcttt taacaaaaaa gcatctgatg aaagattta  ggcaaacatt    5700 ctcaaaataa gagtgatatt ctggatgtag ttattgcagt tatctcatga caatgaggc    5760 ctggattgga aggaaaatat agttgtgtag aattaagcat tttgatagga atctacaagg    5820
tagttgaata taataagcag gtttgggccc ccaaactta  gaaaatcaaa tgcaaggtg   5880 ctggcaaaaa tgaggtttga gtggctggct gtaagagaag gttaactcct agtaaaaggc    5940
```

-continued

| | | | | | |
|---|---|---|---|---|---|
| atttttagaa | ataacaatta | ctgaaaactt | tgaagtatag | tgggagtagc | aaacaaatac | 6000 |
| atgttttttt | tttcttacaa | agaactccta | atcctgagt | aagtgccatt | cattacaata | 6060 |
| agtctctaaa | tttaaaaaaa | aaaaaatcat | atgaggaaat | ctagctttcc | cctttacgct | 6120 |
| gcgtttgatc | tttgtctaaa | tagtgttaaa | attcctttca | ttccaattac | agaactgagc | 6180 |
| ccactcgcaa | gttggagcca | tcagtgggat | acgccacatt | ttggaagccc | cagcatcgtg | 6240 |
| tacttaccag | tgtgttcaca | aaatgaaatt | tgtgtgagag | ctgtacatta | aaaaaaatca | 6300 |
| tcattattat | tattatttgc | agtcatggag | aaccacctac | ccctgacttc | tgtttagtct | 6360 |
| ccttttttaaa | taaaaattac | tgtgttagag | aagaaggcta | ttaaatgtag | tagttaacta | 6420 |
| tgcctcttgt | ctgggggttt | catagagacc | ggtaggaaag | cgcactcctg | cttttcgatt | 6480 |
| tatggtgtgt | gcaagtaaac | aggtgcattg | ctttcaacct | gccatactag | ttttaaaaat | 6540 |
| tcactgaaat | tacaaagata | catatatatg | catatatata | atggaaagtt | tcccggaatg | 6600 |
| caacaattag | cattttaaaa | tcatatatag | gcatgcacat | tctaaatagt | acttttttcat | 6660 |
| gcttcattgt | ttctctggca | gataatttta | ctaagaagaa | aaatagatat | tcgactcccc | 6720 |
| ttccctaaac | aaatccacgg | gcagaggctc | cagcggagcc | gagcccctg | gttttctcgt | 6780 |
| aggccctaga | cggtgttgca | tttatcagtg | atgtcaaacg | tgctcatttg | tcagacatag | 6840 |
| ctgtaaatga | aacaatgtg | tggcaaaata | caagttaaaa | aaaaaaa | | 6887 |

<210> SEQ ID NO 4
<211> LENGTH: 400
<212> TYPE: PRT
<213> ORGANISM: Homo sapiens

<400> SEQUENCE: 4

Met Ala Ser Glu Leu Ala Met Ser Asn Ser Asp Leu Pro Thr Ser Pro
1               5                   10                  15

Leu Ala Met Glu Tyr Val Asn Asp Phe Asp Leu Met Lys Phe Glu Val
                20                  25                  30

Lys Lys Glu Pro Val Glu Thr Asp Arg Ile Ile Ser Gln Cys Gly Arg
            35                  40                  45

Leu Ile Ala Gly Gly Ser Leu Ser Ser Thr Pro Met Ser Thr Pro Cys
        50                  55                  60

Ser Ser Val Pro Pro Ser Pro Ser Phe Ser Ala Pro Ser Pro Gly Ser
65                  70                  75                  80

Gly Ser Glu Gln Lys Ala His Leu Glu Asp Tyr Tyr Trp Met Thr Gly
                85                  90                  95

Tyr Pro Gln Gln Leu Asn Pro Glu Ala Leu Gly Phe Ser Pro Glu Asp
                100                 105                 110

Ala Val Glu Ala Leu Ile Ser Asn Ser His Gln Leu Gln Gly Gly Phe
            115                 120                 125

Asp Gly Tyr Ala Arg Gly Ala Gln Gln Leu Ala Ala Ala Gly Ala
        130                 135                 140

Gly Ala Gly Ala Ser Leu Gly Gly Ser Gly Glu Glu Met Gly Pro Ala
145                 150                 155                 160

Ala Ala Val Val Ser Ala Val Ile Ala Ala Ala Ala Gln Ser Gly
                165                 170                 175

Ala Gly Pro His Tyr His His His His His Ala Ala Gly His His
            180                 185                 190

His His Pro Thr Ala Gly Ala Pro Gly Ala Ala Gly Ser Ala Ala Ala
        195                 200                 205

Ser Ala Gly Gly Ala Gly Gly Ala Gly Gly Gly Pro Ala Ser Ala
    210                 215                 220

Gly Gly Gly Gly Gly Gly Gly Gly Gly Gly Gly Gly Gly Ala Ala
225                 230                 235                 240

Gly Ala Gly Gly Ala Leu His Pro His His Ala Ala Gly Gly Leu His
                245                 250                 255

Phe Asp Asp Arg Phe Ser Asp Glu Gln Leu Val Thr Met Ser Val Arg
                260                 265                 270

Glu Leu Asn Arg Gln Leu Arg Gly Val Ser Lys Glu Val Ile Arg
                275                 280                 285

Leu Lys Gln Lys Arg Arg Thr Leu Lys Asn Arg Gly Tyr Ala Gln Ser
    290                 295                 300

Cys Arg Phe Lys Arg Val Gln Gln Arg His Val Leu Glu Ser Glu Lys
305                 310                 315                 320

Asn Gln Leu Leu Gln Gln Val Asp His Leu Lys Gln Glu Ile Ser Arg
                325                 330                 335

Leu Val Arg Glu Arg Asp Ala Tyr Lys Glu Lys Tyr Glu Lys Leu Val
                340                 345                 350

Ser Ser Gly Phe Arg Glu Asn Gly Ser Ser Ser Asp Asn Pro Ser Ser
                355                 360                 365

Pro Glu Phe Phe Ile Thr Glu Pro Thr Arg Lys Leu Glu Pro Ser Val
    370                 375                 380

Gly Tyr Ala Thr Phe Trp Lys Pro Gln His Arg Val Leu Thr Ser Val
385                 390                 395                 400

<210> SEQ ID NO 5
<211> LENGTH: 373
<212> TYPE: PRT
<213> ORGANISM: Homo sapiens

<400> SEQUENCE: 5

Met Ala Ser Glu Leu Ala Met Ser Asn Ser Asp Leu Pro Thr Ser Pro
1               5                   10                  15

Leu Ala Met Glu Tyr Val Asn Asp Phe Asp Leu Met Lys Phe Glu Val
                20                  25                  30

Lys Lys Glu Pro Val Glu Thr Asp Arg Ile Ile Ser Gln Cys Gly Arg
                35                  40                  45

Leu Ile Ala Gly Gly Ser Leu Ser Ser Thr Pro Met Ser Thr Pro Cys
    50                  55                  60

Ser Ser Val Pro Pro Ser Pro Ser Phe Ser Ala Pro Ser Pro Gly Ser
65                  70                  75                  80

Gly Ser Glu Gln Lys Ala His Leu Glu Asp Tyr Tyr Trp Met Thr Gly
                85                  90                  95

Tyr Pro Gln Gln Leu Asn Pro Glu Ala Leu Gly Phe Ser Pro Glu Asp
                100                 105                 110

Ala Val Glu Ala Leu Ile Ser Asn Ser His Gln Leu Gln Gly Gly Phe
                115                 120                 125

Asp Gly Tyr Ala Arg Gly Ala Gln Gln Leu Ala Ala Ala Gly Ala
    130                 135                 140

Gly Ala Gly Ala Ser Leu Gly Gly Ser Gly Glu Glu Met Gly Pro Ala
145                 150                 155                 160

Ala Ala Val Val Ser Ala Val Ile Ala Ala Ala Ala Gln Ser Gly
                165                 170                 175

Ala Gly Pro His Tyr His His His His His Ala Ala Gly His His
                180                 185                 190

```
His His Pro Thr Ala Gly Ala Pro Gly Ala Gly Ser Ala Ala Ala
        195                 200                 205

Ser Ala Gly Gly Ala Gly Gly Ala Gly Gly Gly Pro Ala Ser Ala
    210                 215                 220

Gly Gly Gly Gly Gly Gly Gly Gly Gly Gly Gly Gly Gly Ala Ala
225                 230                 235                 240

Gly Ala Gly Gly Ala Leu His Pro His His Ala Ala Gly Gly Leu His
                245                 250                 255

Phe Asp Asp Arg Phe Ser Asp Glu Gln Leu Val Thr Met Ser Val Arg
            260                 265                 270

Glu Leu Asn Arg Gln Leu Arg Gly Val Ser Lys Glu Glu Val Ile Arg
        275                 280                 285

Leu Lys Gln Lys Arg Arg Thr Leu Lys Asn Arg Gly Tyr Ala Gln Ser
    290                 295                 300

Cys Arg Phe Lys Arg Val Gln Gln Arg His Val Leu Glu Ser Glu Lys
305                 310                 315                 320

Asn Gln Leu Leu Gln Gln Val Asp His Leu Lys Gln Glu Ile Ser Arg
                325                 330                 335

Leu Val Arg Glu Arg Asp Ala Tyr Lys Glu Lys Tyr Glu Lys Leu Val
            340                 345                 350

Ser Ser Gly Phe Arg Glu Asn Gly Ser Ser Ser Asp Asn Pro Ser Ser
        355                 360                 365

Pro Glu Phe Phe Met
    370
```

```
<210> SEQ ID NO 6
<211> LENGTH: 19
<212> TYPE: RNA
<213> ORGANISM: Artificial Sequence
<220> FEATURE:
<223> OTHER INFORMATION: c-MAF specific siRNA

<400> SEQUENCE: 6
acggcucgag cagcgacaa                                                  19

<210> SEQ ID NO 7
<211> LENGTH: 19
<212> TYPE: RNA
<213> ORGANISM: Artificial Sequence
<220> FEATURE:
<223> OTHER INFORMATION: c-MAF specific siRNA

<400> SEQUENCE: 7
cuuaccagug uguucacaa                                                  19

<210> SEQ ID NO 8
<211> LENGTH: 20
<212> TYPE: RNA
<213> ORGANISM: Artificial Sequence
<220> FEATURE:
<223> OTHER INFORMATION: c-MAF specific siRNA

<400> SEQUENCE: 8
uggaagacua cuacuggaug                                                 20

<210> SEQ ID NO 9
<211> LENGTH: 20
<212> TYPE: RNA
<213> ORGANISM: Artificial Sequence
<220> FEATURE:
```

<223> OTHER INFORMATION: c-MAF specific siRNA

<400> SEQUENCE: 9
auuugcaguc auggagaacc                                               20

<210> SEQ ID NO 10
<211> LENGTH: 20
<212> TYPE: RNA
<213> ORGANISM: Artificial Sequence
<220> FEATURE:
<223> OTHER INFORMATION: c-MAF specific siRNA

<400> SEQUENCE: 10
caaggagaaa uacgagaagu                                               20

<210> SEQ ID NO 11
<211> LENGTH: 20
<212> TYPE: RNA
<213> ORGANISM: Artificial Sequence
<220> FEATURE:
<223> OTHER INFORMATION: c-MAF specific siRNA

<400> SEQUENCE: 11
acaaggagaa auacgagaag                                               20

<210> SEQ ID NO 12
<211> LENGTH: 20
<212> TYPE: RNA
<213> ORGANISM: Artificial Sequence
<220> FEATURE:
<223> OTHER INFORMATION: c-MAF specific siRNA

<400> SEQUENCE: 12
accuggaaga cuacuacugg                                               20

<210> SEQ ID NO 13
<211> LENGTH: 13878
<212> TYPE: DNA
<213> ORGANISM: Homo sapiens

<400> SEQUENCE: 13
aactatatat taaacacctc cggtctgaga ggccgtgttg ggtgtctttg tcaggtgaag      60
aaagagaaga aggctggtac accttcccag gaattctcac tgaagaaaac atctggattt     120
tttacatctc ttgtgcaaaa caaacaaaga tttcattaag tgatgtatat tgttttccaa     180
ggaagaaacc tgcagagaca aaaacaaata agcaaataat tgaaacaaaa atatgataaa     240
cccccaaatt cttccagtgc taatttactt gttatcatgg ttctctacaa aggcagagat     300
cactaattac aggttttttcc agaattcaca tttcacgtca agatcatcca atccaaacag    360
tgtacggaaa gcctagggcc ttcttcactt tgcccccctac cccaccctac acacacgccc    420
ccatctaaat gataccctgt gaaagaaacc tacacatctc atttgtctat attttgcttc    480
ctccctcgcc tcccggtaac caaatgtgag ttgttctcta actgcactgg agaatcagaa     540
tttattgtac atatgtttgt gttccactta ataaaaaaac ctatatttta agataaactt     600
tgttagtaat tcatgaggta agtgactatt tatgctaatc aggcagaaat atattctcaa     660
gcataatgca ttacataaat ttgaatgtaa aatgttcaat tatgaagtaa atacaggtaa     720
tgcaaataat aaaattacctc taataaaaat tataaaagat gtgccttgaa agagagagcg     780
gctttaactt acaactgtga attgcttaaa gagaaaagaa ttaataaatg ctgaattact     840
ctgatgatta tttagcacat aattcaccta ttcataacga ctcctagtaa tcagactgtt     900

```
gtttcacatc ctccaacatg aggcaagact gtttcctcag caattttgcc cttatcagat      960
tatctcgtct gattctatta attttcttcc atgaatctgc taacagtgat ttgtgattta     1020
cttaccctgc taactgaaga ctgttaaaag gatttatcta acactggacc taagaacagt     1080
gtacgcctta tcgttcagtt actctgaaga actctttctc aaatcaattt agttggtttc     1140
atagtgaaat ttagtggaca ctggttagtt ctgccccata aaatcagccc ctaaacaaag     1200
agtccagaca ccatacctga tgcatcccat tctattcaga ttatggatgt ctgattccaa     1260
catgatatat ttgagttgct ataactcaca atcggggaaa atatattcct ttaagctttt     1320
aatctttgta atttggacat gaacaggggt tttgttttc attttgcat gaagtcatta     1380 tgtatgtact gacgtgaaac tataattgtg tttctgatgt tactgtgtca caatattcta     1440
tgcgatgtaa cccatgtcct cctcccctc acaaatctcc tataaatatt cattgctttc     1500
aaaaacttta atactactgg tccgaattgg tcaataatga caaatgcatg gtttctaaat     1560
tactgtatat tgttctacag agattactag agtatatata gcaaggggat gttaagcagt     1620
aagaaaacac agttcacatt gtatttggat tagattggct tggatagaag tgaaacaaac     1680
aatgttagca agaagtcta aagacatgtg gcccactgta attgtacaga atcaaaaacc     1740
tgaatagtac tcattaaaat gagagagctc aattgttata aaagaaatgc tgctaacaga     1800
gaactgtaaa tgtttagaca ccctgtgaa tcactaaata ataatgtaaa aaggataaaa     1860
atgagaatta agttataagc ctgagagcat tactgctaca catctaaaaa aataattctg     1920
atcctctctt ttttttttcc aagagaaaat gggcgactat aaaagacctt gcaataagag     1980
aaataaaaat accatgtctt cacagcagtg tacataaata aaccataaaa atgtgcagat     2040
aataatatat ttagctgccc aaacatgggc atttaatttc tagaaatgat atataacaat     2100
gtaacaatta gatactcagc catgaatgtg tatggcacag tcttcatcat tagcaaactt     2160
tgtgtataaa atattattta ttatttatta taatactgct ttcagaggca atgatcatac     2220
cttacagctt ttaacacaaa tatgatgcaa aaggattaaa agtatatcat aaacaaacaa     2280
taaattcttt ctaaatacac ttaaattcat attttacatg aaaaatataa acttcctaca     2340
tttgtgacta ctgacttta aaaagaccta gaaaactatt gttacgggca atgttaaatg     2400
acataatgct tatgtaatgg aaagtgtgga ttttcctcta aataaactat aatcccttaa     2460
cttcattact agggaaaata ttgttaaaga gaaggaaagc aagggaattc tgctaggttg     2520
cataaatatt gacataatct tcactctttc ttccccaaac tggtaataga catagtttat     2580
tccacccaac aaaatgctct tataagacca aaactaccct tattaacaac ttctctgcag     2640
tcacgatgaa aagaaacact acttgtctga aaaataccga cagcgctgcc cttttcagat     2700
tagggtgtgc ctacgaatct tttgggaagt cttccattaa ggattcctgg gtttgctgaa     2760
actgaagtct actaggatca gagaaattaa cacaggtcta atatggtgca aggaacgagt     2820
gagagacacc tgaggttata aatagcaaag catgctgcgg ggtggggaag accattctga     2880
agtgcaatgt tcaagacgct ggcttaatat atgactaagt gtcagaagtc aggttttctg     2940
agaattactt tccagataaa caactttata gcactgcact taatcttact tactagagac     3000
atctcattta tcactgaatt acaagtaact ttaatcctat tgatattgcc ataaagcccg     3060
ttgaaaatcc atcctggcac ttttaagggg tttggggccc tgttacatgg ggatcctctt     3120 gcaaggtct cagccagaaa ttacaccccg agggtgtctg tatcccctgg cctcttttgtc    3180 aacaatcaag gagaagagga ggggcaaaaa tgatctctgc atctgccagc actttcttcg     3240
```

```
gcccctttcc tatagggtcg ggttctccca cttcagtcaa actaactttg tgtgtctctt    3300
tcctcctccc acactgggta accagctgct tttcacttca tcgacaaaac tggacacgga    3360
tcaatttcaa ctgacctttg ccgaaaggtg gcgctgttga ggtaaaaacc aactcgctcc    3420
aacaatagtt tccactcttc gatccttttg caggcttttc agaattttt ttttttttta    3480 atgcaccctc ctagcgtctc cccttctca taaagtaaaa taaatacgat taaaaacacc    3540
aaatgcattt cattaattga aggaatcaac agtcccaact tctaagcaga cgggctggtc    3600
ttccaaaggc tgggtcggtt tcaggagctt tctctccaaa taaatctctg cttcttcgac    3660
ttgcctatcg cttaaaatc ttagaaacag agttagttgt tggtttcctt cttttttctt    3720 tttcttttt atttcttttt tgcataaact tttagagaat caatctagaa atttgaacta    3780
cttattagca tttgcaactg ggggtggggg gagcagcctc ccccacccca cccccactc    3840 tgcgtttccg gactagttcc agaaaccgcg gtttaaaatt taacccttcg agggtagctg    3900
gtgagggctg gggtattgtt tttccccctt gctccctgcc acgatcaagt ccgaaataat    3960
taaaggaaac gtaaagtgc aaaggcgcg cctgaccctg ataaacagag gtcagatttc    4020
gtaaggggac gggtgagtgt gagtgtgtgt gtgtttgtgt gtgtgtgtgt aagagagaga    4080
gagagcgagc gcgcaatatg agtctcaaag gccaaactcc ggccagtcag gagccggaag    4140
gctgagcccg gctgacctga cttgagcttt ccccggagtt atctcgcata ggcgctcgct    4200
ctgtccaagg gcacgcgacg ccagcgggca gccggtctcc gtgaagaatg gcctctaaac    4260 aacttattt acctcgttgt aaagagaggg ataaaatggg ctttccctct ccacggatgc    4320
ccagccttct gggcaggcgc atggccgggc ggcgcccagc ccgcagcccc gatccggaca    4380
ccccactgca tccctccctt cccggtccct tccccgcacg ggcgcccgag agacggacaa    4440
agagttgggg ccaagtttga gcgccgggca cggccaggct cagggaagga aggtccccgg    4500
cagacacctg ggtaccagag ttggtgcgag gaggaaaagc tgggaggcga attcacaatc    4560 ctggggtgg agggcaggca ggggagggga atcaggccaa tcccagccga gtgagccccc    4620
agcgagctgg ggctccggat gggaggcctg tctcgcgctc caaagaaaag caaaccgccc    4680
tcccaggtcc gcccggattg ccgaagcccc tctggaaaaa ctccttcccc tcttacacca    4740
aactttgcgc cgggcctcgt tccctcccgg gtaggcagcg gcgcaggaag ggttaagcca    4800
gcccgtccca gctgacagtc agctgattgg gccctgattg acagtccga aaagtttcct    4860 tgtttctata ctattatgct aatcgcggcc gctctcgccg cctcccattg gcccggagtg    4920
ccagtcaatt tctcatttgg acctgacgtc acgagtgcta taaaactcag caattgcttt    4980
aaactcttct tgctggatca gaggctttaa aatcttttt catcttctag ctgtagctcg    5040
ggctgcttgt cggcttggcc tcccctccc ccctttgctc tctgcctcgt ctttccccag    5100
gacttcgcta ttttgctttt ttaaaaaaag gcaagaaaga actaaactcc cccctccctc    5160
tcctccagtc gggctgcacc tctgccttgc actttgcaca gaggtagaga gcgcgcgagg    5220
gagagagagg aaagaaaaaa aataataaag agagccaagc agaagaggag gcgagaagca    5280
tgaagtgtta actccccgt gccaaggccc gcgccgcccg gacagacgcc cgccgcgcct    5340
ccagccccga gcgacgccg cgcgcgccct gcctgcagcc cgggccggcg aggcgagccc    5400
ttccttatgc aaagcgcgca gcggagcggc gagcggggga cgccgcgcac cgggccgggc    5460
tcctccagct tcgccgccgc agccaccacc gccgccaccg cagctcgcgg aggatcttcc    5520
cgagcctgaa gccgccggct cggcgcgcaa ggaggcgagc gagcaaggag gggccggggc    5580
gagcgaggga gcacattggc gtgagcaggg gggagggagg gcgggcgcgg ggggcgcggg    5640
```

```
cagggcgggg gggtgtgtgt gtgagcgcgc tcggaggttt cgggccagcc accgccgcgc    5700
aagctagaag cgccccagcc cggcaagctg gctcacccgc tggccaccca gcacagcccg    5760
ctggcccctc tcctgcagcc catctggcgg agcggcggcg gcggcggcgg cggcggcagg    5820
agaatggcat cagaactggc aatgagcaac tccgacctgc ccaccagtcc cctggccatg    5880
gaatatgtta atgacttcga tctgatgaag tttgaagtga aaaggaacc ggtggagacc     5940 gaccgcatca tcagccagtg cggccgtctc atcgccgggg gctcgctgtc ctccacccc     6000 atgagcacgc cgtgcagctc ggtgccccct tcccccagct tctcggcgcc cagcccgggc    6060
tcgggcagcg agcagaaggc gcacctggaa gactactact ggatgaccgg ctacccgcag    6120
cagctgaacc ccgaggcgct gggcttcagc cccgaggacg cggtcgaggc gctcatcagc    6180
aacagccacc agctccaggg cggcttcgat ggctacgcgc gcggggcgca gcagctggcc    6240
gcggcggccg gggccggtgc cggcgcctcc ttgggcggca gcggcgagga gatgggcccc    6300
gccgccgccg tggtgtccgc cgtgatcgcc gcggccgccg cgcagagcgg cgcgggcccg    6360
cactaccacc accaccacca ccacgccgcc ggccaccacc accacccgac ggccggcgcg    6420 cccgcgccc cggcagcgc ggccgcctcg gccggtggcg ctggggggcgc gggcggcggt    6480 ggcccggcca gcgctggggg cggcggcggc ggcggcggcg gcggaggcgg cggggcgcg    6540 gcggggcgg ggggcgccct gcacccgcac cacgccgccg gcggcctgca cttcgacgac    6600
cgcttctccg acgagcagct ggtgaccatg tctgtgcgcg agctgaaccg gcagctgcgc    6660
ggggtcagca aggaggaggt gatccggctg aagcagaaga ggcggaccct gaaaaaccgc    6720
ggctatgccc agtcctgccg cttcaagagg gtgcagcaga gacacgtcct ggagtcggag    6780
aagaaccagc tgctgcagca agtcgaccac ctcaagcagg agatctccag gctggtgcgc    6840
gagagggacg cgtacaagga gaaatacgag aagttggtga gcagcggctt ccgagaaaac    6900
ggctcgagca gcgacaaccc gtcctctccc gagttttca tgtgagtctg acacgcgatt    6960
ccagctagcc accctgataa gtgctccgcg ggggtccggc tcgggtgtgg gcttgctagt    7020
tctagagcca tgctcgccac cacctcacca ccccacccc caccgagttt ggccccttg     7080 gccccctaca cacacacaaa cccgcacgca cacaccacac acacacacac acacacacac    7140 acacccaca ccctgctcga gtttgtggtg gtggtggctg ttttaaactg gggagggaat     7200
gggtgtctgg ctcatggatt gccaatctga aattctccat aacttgctag cttgtttttt    7260 ttttttttt acacccccc gccccacccc cggacttgca caatgttcaa tgatctcagc     7320
agagttcttc atgtgaaacg ttgatcacct ttgaagcctg catcattcac atattttttc    7380
ttcttcttcc ccttcagttc atgaactggt gttcattttc tgtgtgtgtg tgtgttttat    7440
tttgtttgga tttttttttt taattttact tttagagctt gctgtgttgc ccaccttttt    7500
tccaacctcc accctcactc cttctcaacc catctcttcc gagatgaaag aaaaaaaaaa    7560
gcaaagtttt tttttcttct cctgagttct tcatgtgaga ttgagcttgc aaaggaaaaa    7620
aaaatgtgaa atgttataga cttgcagcgt gccgagttcc atcgggtttt tttttagca    7680 ttgttatgct aaaatagaga aaaaatcct catgaacctt ccacaatcaa gcctgcatca    7740
accttctggg tgtgacttgt gagttttggc cttgtgatgc caaatctgag agtttagtct    7800
gccattaaaa aaactcattc tcatctcatg cattattatg cttgctactt tgtcttagca    7860
acaatgaact ataactgttt caaagacttt atggaaaaga gacattatat taataaaaaa    7920
aaaaagcctg catgctggac atgtatggta taattatttt ttccttttt tttccttttg    7980
```

```
gcttggaaat ggacgttcga agacttatag catggcattc atactttgt tttattgcct    8040 catgactttt ttgagtttag aacaaaacag tgcaaccgta gagccttctt cccatgaaat    8100
tttgcatctg ctccaaaact gctttgagtt actcagaact tcaacctccc aatgcactga    8160
aggcattcct tgtcaaagat accagaatgg gttacacatt taacctggca aacattgaag    8220
aactcttaat gttttctttt taataagaat gacgccccac tttggggact aaaattgtgc    8280
tattgccgag aagcagtcta aaatttattt tttaaaaaga gaaactgccc cattattttt    8340
ggtttgtttt attttattt tatattttt ggcttttggt cattgtcaaa tgtggaatgc    8400
tctgggtttc tagtatataa tttaattcta gtttttataa tctgttagcc cagttaaaat    8460
gtatgctaca gataaaggaa tgttatagat aaatttgaaa gagttaggtc tgtttagctg    8520 tagattttt aaacgattga tgcactaaat tgtttactat tgtgatgtta aggggggtag    8580
agtttgcaag gggactgttt aaaaaagta gcttatacag catgtgcttg caacttaaat    8640
ataagttggg tatgtgtagt ctttgctata ccactgactg tattgaaaac caaagtatta    8700 agagggaaa cgcccctgtt tatatctgta ggggtatttt acattcaaaa atgtatgttt    8760
ttttttcttt tcaaaattaa agtatttggg actgaattgc actaagatat aacctgcaag    8820
catataatac aaaaaaaaat tgcaaaactg tttagaacgc taataaaatt tatgcagtta    8880
taaaaatggc attactgcac agttttaaga tgatgcagat ttttttacag ttgtattgtg    8940
gtgcagaact ggattttctg taacttaaaa aaaaatccac agttttaaag gcaataatca    9000
gtaaatgtta ttttcaggga ctgacatcct gtctttaaaa agaaatgaaa agtaaatctt    9060
accacaataa atataaaaaa atcttgtcag ttacttttct tttacatatt ttgctgtgca    9120
aaattgtttt atatcttgag ttactaacta accacgcgtg ttgttcctat gtgcttttct    9180
ttcattttca attctggtta tatcaagaaa agaataatct acaataataa acggcatttt    9240
tttttgattc tgtactcagt ttcttagtgt acagtttaac tgggcccaac aacctcgtta    9300
aaagtgtaaa atgcatcctt ttctccagtg gaaggattcc tggaggaata gggagacagt    9360
aattcagggt gaaattatag gctgtttttt gaagtgagga ggctggcccc atatactgat    9420
tagcaatatt taatatagat gtaaattatg acctcatttt tttctcccca agttttcag    9480 ttttcaaatg agttgagcca taattgccct tggtaggaaa acaaaacaa acagtggaa    9540 ctaggcttcc tgagcatggc cctacacttc tgatcaggag caaagccatc catagacaga    9600
ggagccggac aaatatggcg catcagaggt ggcttgcgca catatgcatt gaacggtaaa    9660
gagaaacagc gcttgccttt tcactaaagt tgactatttt tccttcttct cttacacacc    9720
gagattttct tgttagcaag gcctgacaag atttaacata aacatgacaa atcatagttg    9780
tttgttttgt tttgctttc tctttaacac tgaagatcat ttgtcttaaa taggaaaaag    9840
aaaatccact ccttacttcc atatttccaa gtacatatct ggtttaaact atgttatcaa    9900
atcatatttc accgtgaata ttcagtggag aacttctcta cctggatgag ctagtaatga    9960
tttcagatca tgctatcccc agaaataaaa gcaaaaaata atacctgtgt ggaatatagg    10020
ctgtgctttg atttactggt atttacccca aaataggctg tgtatggggg ctgacttaaa    10080
gatcccttgg aaagactcaa aactaccttc actagtagga ctcctaagcg ctgacctatt    10140
tttaaatgac acaaattcat gaaactaatg ttacaaattc atgcagtttg cactcttagt    10200
catcttcccc tagcacacca atagaatgtt agacaaagcc agcactgttt tgaaaataca    10260
gccaaacacg atgactttg ttttgttttc tgccgttctt aaaagaaaaa aagataatat    10320
tgcaactctg actgaaagac ttattttaa gaaaacaggt tgtgtttggt gctgctaagt    10380
```

```
tctggccagt ttatcatctg gccttcctgc ctattttta caaaacacga agacagtgtg   10440
taacctcgac attttgacct tcctttatgt gctagtttag acaggctcct gaatccacac   10500
ttaattttgc ttaacaaaag tcttaatagt aaacctcccc tcatgagctt gaagtcaagt   10560
gttcttgact tcagatattt ctttccttt tttttttttt tcctcatcac aactaagaga   10620
tacacaaact ctgaagaagc agaaatggag agaatgcttt taacaaaaaa gcatctgatg   10680
aaagatttta ggcaaacatt ctcaaaataa gagtgatatt ctggatgtag ttattgcagt   10740
tatctcatga caaatgaggc ctggattgga aggaaaatat agttgtgtag aattaagcat   10800
tttgatagga atctacaagg tagttgaata taataagcag gtttgggccc ccaaacttta   10860
gaaaatcaaa tgcaaggtg ctggcaaaaa tgaggtttga gtggctggct gtaagagaag   10920
gttaactcct agtaaaaggc atttttagaa ataacaatta ctgaaaactt tgaagtatag   10980
tgggagtagc aaacaaatac atgtttttt ttcttacaa agaactccta aatcctgagt   11040
aagtgccatt cattacaata agtctctaaa tttaaaaaaa aaaaaatcat atgaggaaat   11100
ctagctttcc cctttacgct gcgtttgatc tttgtctaaa tagtgttaaa attcctttca   11160
ttccaattac agaactgagc ccactcgcaa gttgagcca tcagtgggat acgccacatt   11220
ttggaagccc cagcatcgtg tacttaccag tgtgttcaca aaatgaaatt tgtgtgagag   11280
ctgtacatta aaaaaaatca tcattattat tattatttgc agtcatggag aaccacctac   11340
ccctgacttc tgtttagtct ccttttaaa taaaaattac tgtgttagag aagaaggcta   11400
ttaaatgtag tagttaacta tgcctcttgt ctgggggttt catagagacc ggtaggaaag   11460
cgcactcctg cttttcgatt tatggtgtgt gcaagtaaac aggtgcattg ctttcaacct   11520
gccatactag ttttaaaaat tcactgaaat tacaaagata catatatatg catatatata   11580
atggaaagtt tcccggaatg caacaattag cattttaaaa tcatatatag gcatgcacat   11640
tctaaatagt acttttcat gcttcattgt ttctctggca gataattta ctaagaagaa   11700 aaatagatat tcgactcccc ttccctaaac aaatccacgg gcagaggctc cagcggagcc   11760 gagcccctg gttttctcgt aggccctaga cggtgttgca tttatcagtg atgtcaaacg   11820
tgctcatttg tcagacatag ctgtaaatga aaacaatgtg tggcaaaata caaagttagt   11880
taaatacaca ccctctgtgt gattttttgc tccctttct tttttgctcc tactcaaaaa   11940
aaaaaaaatc acctccttta catttccctg gcttcttgca tgtttccctt ttcaaaaacc   12000
atgtaataat ttttacaat gtatctgaca cattaatata ttgacatcaa ataggcagac   12060
attctacttt tgcctggcaa ataaatctgc tacggagaca tcatttcctc actgtctcaa   12120
agccataact acctgggagt ctttcaacac agaccctcc gatgggaaat gctgtttatt   12180
actgaatgca ggatgctcac gctctgatct tttctccctt gtgcctttac cccagtcatt   12240
tttacttagc aacaccaatt ctagatactt ctgttctgaa gtagaaccac ccccttgcca   12300
cactgccagt tttcctgcta aaagcagtgg acagaagaca gatcatggtc accctcacaa   12360
acatggcaca cagctgtctc ggtagctgca ttcccagcat gtcctggtct aaatatctag   12420
agttgcctat gacacgttca aaggttccca agcacagtac attgggaggc ttttgctgct   12480
gtggccgttg ttttcgttta ggccaactta cttccgtatt cacatactct ggctttacg    12540 aaatacactc ctccagtcta ctaggccaat caatatattt aaaagtctga ttgccacata   12600
agtctctctc tctctctttt tgttttttgt ttgtttgttt ttttctgttt tggctgccgg   12660
tagttaaaga ctgagatagg ttggaagact aaaatacagg agtacatgag tgacaacctt   12720
```

```
cagccgtctg atttccatgc cggtaaaaca cacaaccaag ctcttcttag cgctgctaat   12780
ataaacattc actaagaggg aataggaagt gagatttacc agcttcactt tgctgatttg   12840
caaggttccc cactacgatt cactgtcatt tgattttga aaataatttt tgtccgtctc    12900
tttgaagaaa tgtcttagtt cttttatttt gtttgtttgg ttttttttag agaagtttta   12960
tctgcagtga taggctacaa tttttatctc cgctgattat ttgtcaggat gctgaatgaa   13020
taatttggtc ctgtgccttc cttgttgttc tgaggaaaat aagagaaact tggaagtttg   13080
tttcactctt agcccatcct aaatctaaaa gaagatgtcc caggtccagg caggccatgt   13140
agtagttata aaggaggtgg tccaggtcca gccacctcaa tcaggatttg tttgttttga   13200
agcatttgct taaaagcgga gcaagagtct taacccaact tgccataaca ctgcttttct   13260
cgcttttgat gtaaatcttc aaaattcaga catcaaacag ccccagaaaa ggggaattct   13320
ctccaggcat tgctccgccc cagctcctga acaaacccag ctctgtctag catttttttc   13380
cctagcgggg gtaggggaca gggtgagaga atttcagtct cccaggctgt ctcatgattg   13440
ttagggcata aagaaacaca gtcctgccac aaattgggag catctttacc ctttagagag   13500
aaacaaaaca aaactaaaca aacaaatcaa attgctttgc atgaaggcgt agcaaataaa   13560
atctcgggct ccctgttccc tgcaccattt gtaggaggtg agaaatgagg gaaacaagag   13620 aaagggaac tttaaaagcg ggaggcccag aaataatccc tgttaccagt ctgaatttca     13680
cttgctccgt ggctaacgtc agacctagtg tgcatgtatg ccagaagtaa actaggctcg   13740
gctgtccatt tctttaaaat atgttcacat gtttcctttt tgaaaacaat tttggggact   13800
aaacccaaat ggagagattt gaggaaatcg ttaatgtctt aacatttgag tatatttata   13860
aatgtatcag tctgtgat                                                 13878
```

<210> SEQ ID NO 14
<211> LENGTH: 455
<212> TYPE: PRT
<213> ORGANISM: Artificial Sequence
<220> FEATURE:
<223> OTHER INFORMATION: INB-1-11-8 (H1) Heavy Chain
<220> FEATURE:
<221> NAME/KEY: MISC_FEATURE
<222> LOCATION: (1)..(132)
<223> OTHER INFORMATION: Variable Heavy Chain
<220> FEATURE:
<221> NAME/KEY: MISC_FEATURE
<222> LOCATION: (133)..(138)
<223> OTHER INFORMATION: Start of constant region
<220> FEATURE:
<221> NAME/KEY: MISC_FEATURE
<222> LOCATION: (317)..(416)
<223> OTHER INFORMATION: Variant

<400> SEQUENCE: 14

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Arg Leu Val Thr Pro
            20                  25                  30

Gly Thr Pro Leu Thr Leu Thr Cys Thr Ala Ser Gly Phe Ser Leu Asn
        35                  40                  45

Asn Tyr Pro Met Thr Trp Val Arg Gln Ala Pro Gly Lys Gly Leu Asp
    50                  55                  60

Tyr Ile Gly Val Ile Asn Asn Ser Gly Glu Thr Ala Tyr Ala Thr Trp
65                  70                  75                  80

Ala Lys Arg Arg Phe Thr Ile Ser Arg Thr Ser Thr Thr Leu Tyr Leu
                85                  90                  95

```
Lys Ile Ala Ser Pro Thr Ile Glu Asp Thr Ala Thr Tyr Phe Cys Ala
            100                 105                 110

Arg Gly Gly Pro Val Ser Ser Asp Met Trp Gly Pro Gly Thr Leu Val
            115                 120                 125

Ile Val Ser Ser Gly Gln Pro Lys Ala Pro Ser Val Phe Pro Leu Ala
130                 135                 140

Pro Cys Cys Gly Asp Thr Pro Ser Ser Thr Val Thr Leu Gly Cys Leu
145                 150                 155                 160

Val Lys Gly Tyr Leu Pro Glu Pro Val Thr Val Thr Trp Asn Ser Gly
                165                 170                 175

Thr Leu Thr Asn Gly Val Arg Thr Phe Pro Ser Val Arg Gln Ser Ser
            180                 185                 190

Gly Leu Tyr Ser Leu Ser Ser Val Val Ser Val Thr Ser Ser Ser Gln
            195                 200                 205

Pro Val Thr Cys Asn Val Ala His Pro Ala Thr Asn Thr Lys Val Asp
        210                 215                 220

Lys Thr Val Ala Pro Ser Thr Cys Ser Lys Pro Thr Cys Pro Pro Pro
225                 230                 235                 240

Glu Leu Leu Gly Gly Pro Ser Val Phe Ile Phe Pro Pro Lys Pro Lys
                245                 250                 255

Asp Thr Leu Met Ile Ser Arg Thr Pro Glu Val Thr Cys Val Val Val
            260                 265                 270

Asp Val Ser Gln Asp Asp Pro Glu Val Gln Phe Thr Trp Tyr Ile Asn
            275                 280                 285

Asn Glu Gln Val Arg Thr Ala Arg Pro Pro Leu Arg Glu Gln Gln Phe
290                 295                 300

Asn Ser Thr Ile Arg Val Val Ser Thr Leu Pro Ile Ala His Gln Asp
305                 310                 315                 320

Trp Leu Arg Gly Lys Glu Phe Lys Cys Lys Val His Asn Lys Ala Leu
                325                 330                 335

Pro Ala Pro Ile Glu Lys Thr Ile Ser Lys Ala Arg Gly Gln Pro Leu
            340                 345                 350

Glu Pro Lys Val Tyr Thr Met Gly Pro Pro Arg Glu Glu Leu Ser Ser
            355                 360                 365

Arg Ser Val Ser Leu Thr Cys Met Ile Asn Gly Phe Tyr Pro Ser Asp
370                 375                 380

Ile Ser Val Glu Trp Glu Lys Asn Gly Lys Ala Glu Asp Asn Tyr Lys
385                 390                 395                 400

Thr Thr Pro Ala Val Leu Asp Ser Asp Gly Ser Tyr Phe Leu Tyr Ser
                405                 410                 415

Lys Leu Ser Val Pro Thr Ser Glu Trp Gln Arg Gly Asp Val Phe Thr
            420                 425                 430

Cys Ser Val Met His Glu Ala Leu His Asn His Tyr Thr Gln Lys Ser
        435                 440                 445

Ile Ser Arg Ser Pro Gly Lys
    450                 455

<210> SEQ ID NO 15
<211> LENGTH: 132
<212> TYPE: PRT
<213> ORGANISM: Artificial Sequence
<220> FEATURE:
<223> OTHER INFORMATION: INB-1-11-8 (H1) Variable Heavy Chain

<400> SEQUENCE: 15
```

```
Met Glu Thr Gly Leu Arg Trp Leu Leu Leu Val Ala Val Leu Lys Gly
1               5                   10                  15

Val Gln Cys Gln Ser Leu Glu Glu Ser Gly Gly Arg Leu Val Thr Pro
            20                  25                  30

Gly Thr Pro Leu Thr Leu Thr Cys Thr Ala Ser Gly Phe Ser Leu Asn
            35                  40                  45

Asn Tyr Pro Met Thr Trp Val Arg Gln Ala Pro Gly Lys Gly Leu Asp
        50                  55                  60

Tyr Ile Gly Val Ile Asn Asn Ser Gly Glu Thr Ala Tyr Ala Thr Trp
65                  70                  75                  80

Ala Lys Arg Arg Phe Thr Ile Ser Arg Thr Ser Thr Thr Leu Tyr Leu
                85                  90                  95

Lys Ile Ala Ser Pro Thr Ile Glu Asp Thr Ala Thr Tyr Phe Cys Ala
                100                 105                 110

Arg Gly Gly Pro Val Ser Ser Asp Met Trp Gly Pro Gly Thr Leu Val
            115                 120                 125

Ile Val Ser Ser
            130

<210> SEQ ID NO 16
<211> LENGTH: 236
<212> TYPE: PRT
<213> ORGANISM: Artificial Sequence
<220> FEATURE:
<223> OTHER INFORMATION: INB-1-11-8 (L4) Light Chain
<220> FEATURE:
<221> NAME/KEY: MISC_FEATURE
<222> LOCATION: (1)..(133)
<223> OTHER INFORMATION: Variable Light Chain
<220> FEATURE:
<221> NAME/KEY: MISC_FEATURE
<222> LOCATION: (134)..(139)
<223> OTHER INFORMATION: Start of constant region
<220> FEATURE:
<221> NAME/KEY: MISC_FEATURE
<222> LOCATION: (146)..(149)
<223> OTHER INFORMATION: Variant

<400> SEQUENCE: 16

Met Asp Thr Arg Ala Pro Thr Gln Leu Leu Gly Leu Leu Leu Leu Trp
1               5                   10                  15

Leu Pro Gly Ala Thr Phe Ala Gln Val Leu Thr Gln Thr Ala Ser Pro
            20                  25                  30

Val Ser Ala Val Val Gly Gly Thr Val Thr Ile Asn Cys Gln Ser Ser
            35                  40                  45

Gln Ser Val Tyr Arg Gly Asp Trp Leu Ala Trp Tyr Gln Gln Arg Pro
        50                  55                  60

Gly Gln Pro Pro Lys Leu Leu Ile Tyr Gly Ala Ser Thr Leu Ala Ser
65                  70                  75                  80

Gly Val Pro Ser Arg Phe Lys Gly Ser Gly Ser Gly Thr His Phe Thr
                85                  90                  95

Leu Thr Ile Ser Asp Leu Asp Cys Asp Asp Ala Ala Thr Tyr Tyr Cys
                100                 105                 110

Ala Gly Gly Phe Ser Gly His Ile Tyr Asp Phe Gly Gly Gly Thr Glu
            115                 120                 125

Val Val Val Lys Gly Asp Pro Val Ala Pro Thr Val Leu Ile Phe Pro
            130                 135                 140

Pro Ala Ala Asp Gln Val Ala Thr Gly Thr Val Thr Ile Val Cys Val
145                 150                 155                 160
```

```
Ala Asn Lys Tyr Phe Pro Asp Val Thr Val Thr Trp Glu Val Asp Gly
            165                 170                 175

Thr Thr Gln Thr Thr Gly Ile Glu Asn Ser Lys Thr Pro Gln Asn Ser
            180                 185                 190

Ala Asp Cys Thr Tyr Asn Leu Ser Ser Thr Leu Thr Leu Thr Ser Thr
            195                 200                 205

Gln Tyr Asn Ser His Lys Glu Tyr Thr Cys Lys Val Thr Gln Gly Thr
            210                 215                 220

Thr Ser Val Val Gln Ser Phe Asn Arg Gly Asp Cys
225                 230                 235

<210> SEQ ID NO 17
<211> LENGTH: 133
<212> TYPE: PRT
<213> ORGANISM: Artificial Sequence
<220> FEATURE:
<223> OTHER INFORMATION: INB-1-11-8 (L4) Variable Light Chain

<400> SEQUENCE: 17

Met Asp Thr Arg Ala Pro Thr Gln Leu Leu Gly Leu Leu Leu Leu Trp
1               5                   10                  15

Leu Pro Gly Ala Thr Phe Ala Gln Val Leu Thr Gln Thr Ala Ser Pro
            20                  25                  30

Val Ser Ala Val Val Gly Gly Thr Val Thr Ile Asn Cys Gln Ser Ser
        35                  40                  45

Gln Ser Val Tyr Arg Gly Asp Trp Leu Ala Trp Tyr Gln Gln Arg Pro
    50                  55                  60

Gly Gln Pro Pro Lys Leu Leu Ile Tyr Gly Ala Ser Thr Leu Ala Ser
65                  70                  75                  80

Gly Val Pro Ser Arg Phe Lys Gly Ser Gly Ser Gly Thr His Phe Thr
                85                  90                  95

Leu Thr Ile Ser Asp Leu Asp Cys Asp Asp Ala Ala Thr Tyr Tyr Cys
            100                 105                 110

Ala Gly Gly Phe Ser Gly His Ile Tyr Asp Phe Gly Gly Gly Thr Glu
        115                 120                 125

Val Val Val Lys Gly
    130

<210> SEQ ID NO 18
<211> LENGTH: 13
<212> TYPE: PRT
<213> ORGANISM: Artificial Sequence
<220> FEATURE:
<223> OTHER INFORMATION: CDR1

<400> SEQUENCE: 18

Gln Ser Ser Gln Ser Val Tyr Arg Gly Asp Trp Leu Ala
1               5                   10

<210> SEQ ID NO 19
<211> LENGTH: 7
<212> TYPE: PRT
<213> ORGANISM: Artificial Sequence
<220> FEATURE:
<223> OTHER INFORMATION: CDR2

<400> SEQUENCE: 19

Gly Ala Ser Thr Leu Ala Ser
1               5
```

```
<210> SEQ ID NO 20
<211> LENGTH: 10
<212> TYPE: PRT
<213> ORGANISM: Artificial Sequence
<220> FEATURE:
<223> OTHER INFORMATION: CDR3

<400> SEQUENCE: 20

Ala Gly Gly Phe Ser Gly His Ile Tyr Asp
1               5                   10

<210> SEQ ID NO 21
<211> LENGTH: 5
<212> TYPE: PRT
<213> ORGANISM: Artificial Sequence
<220> FEATURE:
<223> OTHER INFORMATION: CDR1

<400> SEQUENCE: 21

Asn Tyr Pro Met Thr
1               5

<210> SEQ ID NO 22
<211> LENGTH: 16
<212> TYPE: PRT
<213> ORGANISM: Artificial Sequence
<220> FEATURE:
<223> OTHER INFORMATION: CDR2

<400> SEQUENCE: 22

Val Ile Asn Asn Ser Gly Glu Thr Ala Tyr Ala Thr Trp Ala Lys Arg
1               5                   10                  15

<210> SEQ ID NO 23
<211> LENGTH: 8
<212> TYPE: PRT
<213> ORGANISM: Artificial Sequence
<220> FEATURE:
<223> OTHER INFORMATION: CDR3

<400> SEQUENCE: 23

Gly Gly Pro Val Ser Ser Asp Met
1               5

<210> SEQ ID NO 24
<211> LENGTH: 18
<212> TYPE: PRT
<213> ORGANISM: Homo sapiens

<400> SEQUENCE: 24

Glu Gln Lys Ala His Leu Glu Asp Tyr Tyr Trp Met Thr Gly Tyr Pro
1               5                   10                  15

Gln Gln
```

METHOD FOR THE DIAGNOSIS, PROGNOSIS AND TREATMENT OF PROSTATE CANCER METASTASIS

CROSS-REFERENCE TO RELATED APPLICATIONS

This application is a continuation of U.S. application Ser. No. 15/183,419, filed Jun. 15, 2016, which is a continuation-in-part of U.S. application Ser. No. 14/435,128, which is a national stage of International Application No. PCT/IB2013/002866 filed Oct. 9, 2013, which claims priority to U.S. Provisional Patent Application Ser. No. 61/713,318, filed on Oct. 12, 2012, which are incorporated herein by reference in their entireties.

REFERENCE TO SEQUENCE LISTING

The content of the electronically submitted sequence listing (Name: 3190_0030005_ST25.txt, Size: 58,812 bytes, and Date of Creation: Sep. 11, 2018) filed with the application is incorporated herein by reference in its entirety.

BACKGROUND OF THE INVENTION

Field of the Invention

The present invention relates to the diagnosis or the prognosis of metastasis, relapse or recurrence in prostate cancer based on determining if the c-MAF gene, within the 16q22-24 genomic region, is amplified and/or copy gained in a primary tumor sample. Likewise, the invention also relates to a method for the diagnosis or the prognosis of metastasis, relapse, or recurrence in prostate cancer, as well as to a method for designing a customized therapy in a subject with prostate cancer, which comprises determining the c-MAF gene expression level or 16q22-24 amplification and/or copy gain. Finally, the invention relates to the use of a c-MAF inhibitor as a therapeutic target for the treatment of prostate cancer metastasis, relapse or recurrence.

Background Art

The Problem:

Metastasis, a complex process caused by elaborate interactions between tumor cells and the surrounding normal tissues in different vital organs, accounts for 90 percent of all cancer deaths in patients with solid tumors. The molecular and cellular mechanisms that lead primary tumors to form metastases must be understood in order to better address this major life-threatening problem. The identification of metastasis genes and mechanisms is essential for understanding the basic biology of this lethal condition and its implications for clinical practice.

Introduction and Interest: Prostate Organ-Specific Metastasis

Prostate cancer is a form of cancer that develops in the prostate, a gland in the male reproductive system. Most prostate cancers are slow growing; however, there are cases of aggressive prostate cancers. The cancer cells may metastasize (spread) from the prostate to other parts of the body, particularly the bones and lymph nodes. Prostate cancer may cause pain, difficulty in urinating, problems during sexual intercourse, or erectile dysfunction. Other symptoms can potentially develop during later stages of the disease.

Rates of detection of prostate cancers vary widely across the world, with South and East Asia detecting less frequently than in Europe, and especially the United States. Prostate cancer tends to develop in men over the age of fifty and although it is one of the most prevalent types of cancer in men, many never have symptoms, undergo no therapy, and eventually die of other causes. About two-thirds of cases are slow growing, the other third more aggressive and fast developing.

Many factors, including genetics and diet, have been implicated in the development of prostate cancer. The presence of prostate cancer may be indicated by symptoms, physical examination, prostate-specific antigen (PSA), or biopsy. The PSA test increases cancer detection but does not decrease mortality. Moreover, prostate test screening is controversial at the moment and may lead to unnecessary, even harmful, consequences in some patients. Nonetheless, suspected prostate cancer is typically confirmed by taking a biopsy of the prostate and examining it under a microscope. Further tests, such as CT scans and bone scans, may be performed to determine whether prostate cancer has spread.

Management strategies for prostate cancer should be guided by the severity of the disease. Many low-risk tumors can be safely followed with active surveillance. Curative treatment generally involves surgery, various forms of radiation therapy, or, less commonly, cryosurgery; hormonal therapy and chemotherapy are generally reserved for cases of advanced disease (although hormonal therapy may be given with radiation in some cases).

The age and underlying health of the man, the extent of metastasis, appearance under the microscope and response of the cancer to initial treatment are important in determining the outcome of the disease. The decision whether or not to treat localized prostate cancer (a tumor that is contained within the prostate) with curative intent is a patient trade-off between the expected beneficial and harmful effects in terms of patient survival and quality of life.

The specific causes of prostate cancer remain unknown. Genetic background may contribute to prostate cancer risk, as suggested by associations with race, family, and specific gene variants. No single gene is responsible for prostate cancer; many different genes have been implicated. Mutations in BRCA1 and BRCA2, important risk factors for ovarian cancer and breast cancer in women, have also been implicated in prostate cancer. Other linked genes include the Hereditary Prostate cancer gene 1 (HPC1), the androgen receptor, and the vitamin D receptor. TMPRSS2-ETS gene family fusion, specifically TMPRSS2-ERG or TMPRSS2-ETV1/4 promotes cancer cell growth.

Loss of cancer suppressor genes, early in the prostatic carcinogenesis, have been localized to chromosomes 8p, 10q, 13q,and 16q. P53 mutations in the primary prostate cancer are relatively low and are more frequently seen in metastatic settings, hence, p53 mutations are a late event in pathology of prostate cancer. Other tumor suppressor genes that are thought to play a role in prostate cancer include PTEN (gene) and KAI1. Up to 70 percent of men with prostate cancer have lost one copy of the PTEN gene at the time of diagnosis. Relative frequency of loss of E-cadherin and CD44 has also been observed.

Prostate cancer is classified as an adenocarcinoma, or glandular cancer, that begins when normal semen-secreting prostate gland cells mutate into cancer cells. The region of prostate gland where the adenocarcinoma is most common is the peripheral zone. Initially, small clumps of cancer cells remain confined to otherwise normal prostate glands, a condition known as carcinoma in situ or prostatic intraepithelial neoplasia (PIN). Although there is no proof that PIN is a cancer precursor, it is closely associated with cancer.

Over time, these cancer cells begin to multiply and spread to the surrounding prostate tissue (the stroma) forming a tumor. Eventually, the tumor may grow large enough to invade nearby organs such as the seminal vesicles or the rectum, or the tumor cells may develop the ability to travel in the bloodstream and lymphatic system. Prostate cancer is considered a malignant tumor because it is a mass of cells that can invade other parts of the body. This invasion of other organs is called metastasis. Prostate cancer most commonly metastasizes to the bones, lymph nodes, and may invade rectum, bladder and lower ureters after local progression.

Molecular Traits of Prostate Cancer

RUNX2 is a transcription factor that prevents cancer cells from undergoing apoptosis thereby contributing to the development of prostate cancer.

The PI3k/Akt signaling cascade works with the transforming growth factor beta/SMAD signaling cascade to ensure prostate cancer cell survival and protection against apoptosis. X-linked inhibitor of apoptosis (XIAP) is hypothesized to promote prostate cancer cell survival and growth and is a target of research because if this inhibitor can be shut down then the apoptosis cascade can carry on its function in preventing cancer cell proliferation. Macrophage inhibitory cytokine-1 (MIC-1) stimulates the focal adhesion kinase (FAK) signaling pathway which leads to prostate cancer cell growth and survival.

The androgen receptor helps prostate cancer cells to survive and is a target for many anti-cancer research studies; so far, inhibiting the androgen receptor has only proven to be effective in mouse studies. Prostate specific membrane antigen (PSMA) stimulates the development of prostate cancer by increasing folate levels for the cancer cells to use to survive and grow; PSMA increases available folates for use by hydrolyzing glutamated folates.

Diagnosis

The only test that can fully confirm the diagnosis of prostate cancer is a biopsy, the removal of small pieces of the prostate for microscopic examination. However, prior to a biopsy, less invasive testing can be conducted.

There are also several other tests that can be used to gather more information about the prostate and the urinary tract. Digital rectal examination (DRE) may allow a doctor to detect prostate abnormalities. Cystoscopy shows the urinary tract from inside the bladder, using a thin, flexible camera tube inserted down the urethra. Transrectal ultrasonography creates a picture of the prostate using sound waves from a probe in the rectum.

Prostate Imaging

Ultrasound (US) and Magnetic Resonance Imaging (MRI) are the two main imaging methods used for prostate cancer detection.

Biopsy

Micrograph showing a prostate cancer (conventional adenocarcinoma) with perineural invasion. H&E stain.

If cancer is suspected, a biopsy is offered expediently. During a biopsy a urologist or radiologist obtains tissue samples from the prostate via the rectum. A biopsy gun inserts and removes special hollow-core needles (usually three to six on each side of the prostate) in less than a second. Prostate biopsies are routinely done on an outpatient basis and rarely require hospitalization. Fifty-five percent of men report discomfort during prostate biopsy.

Gleason Score

The tissue samples are then examined under a microscope to determine whether cancer cells are present, and to evaluate the microscopic features (or Gleason score) of any cancer found. Prostate specific membrane antigen is a transmembrane carboxypeptidase and exhibits folate hydrolase activity. This protein is overexpressed in prostate cancer tissues and is associated with a higher Gleason score.

Tumor Markers

Tissue samples can be stained for the presence of PSA and other tumor markers in order to determine the origin of malignant cells that have metastasized.

Small cell carcinoma is a very rare (1%) type of prostate cancer that cannot be diagnosed using the PSA. As of 2009 researchers are trying to determine the best way to screen for this type of prostate cancer because it is a relatively unknown and rare type of prostate cancer but very serious and quick to spread to other parts of the body. Possible methods include chromatographic separation methods by mass spectrometry, or protein capturing by immunoassays or immunized antibodies. The test method will involve quantifying the amount of the biomarker PCI, with reference to the Gleason Score. Not only is this test quick, it is also sensitive. It can detect patients in the diagnostic grey zone, particularly those with a serum free to total Prostate Specific Antigen ratio of 10-20%.

The expression of Ki-67 by immunohistochemistry may be a significant predictor of patient outcome for men with prostate cancer.

Classification

An important part of evaluating prostate cancer is determining the stage, or how far the cancer has spread. Knowing the stage helps define prognosis and is useful when selecting therapies. The most common system is the four-stage TNM system (abbreviated from Tumor/Nodes/Metastases). Its components include the size of the tumor, the number of involved lymph nodes, and the presence of any other metastases.

The most important distinction made by any staging system is whether or not the cancer is still confined to the prostate. In the TNM system, clinical T1 and T2 cancers are found only in the prostate, while T3 and T4 cancers have spread elsewhere. Several tests can be used to look for evidence of spread. These include computed tomography to evaluate spread within the pelvis, bone scans to look for spread to the bones, and endorectal coil magnetic resonance imaging to closely evaluate the prostatic capsule and the seminal vesicles. Bone scans should reveal osteoblastic appearance due to increased bone density in the areas of bone metastasis—opposite to what is found in many other cancers that metastasize.

After a prostate biopsy, a pathologist looks at the samples under a microscope. If cancer is present, the pathologist reports the grade of the tumor. The grade tells how much the tumor tissue differs from normal prostate tissue and suggests how fast the tumor is likely to grow. The Gleason system is used to grade prostate tumors from 2 to 10, where a Gleason score of 10 indicates the most abnormalities. The pathologist assigns a number from 1 to 5 for the most common pattern observed under the microscope, then does the same for the second-most-common pattern. The sum of these two numbers is the Gleason score. The Whitmore-Jewett stage is another method sometimes used.

Screening

Prostate cancer screening is an attempt to find unsuspected cancers, and may lead to more specific follow-up tests such as a biopsy, with cell samples taken for closer study. Options include the digital rectal exam (DRE) and the prostate-specific antigen (PSA) blood test. Such screening is controversial and, in some patients, may lead to unnecessary, even harmful, consequences. A 2010 analysis concluded that routine screening with either a DRE or PSA is not supported by the evidence as there is no mortality benefit from screening. More recently, the United States Preventive Services Task Force (USPSTF) recommended against the PSA test for prostate cancer screening in healthy men. This USPSTF recommendation, released in October 2011, is based on "review of evidence" studies concluding that "Prostate-specific antigen-based screening results in small or no reduction in prostate cancer-specific mortality and is associated with harms related to subsequent evaluation and treatments, some of which may be unnecessary.

Modern screening tests have found cancers that might never have developed into serious disease, and that "the slight reduction of risk by surgically removing the prostate or treating it with radiation may not outweigh the substantial side effects of these treatments," an opinion also shared by the CDC.

Aggressive Cancer

If the cancer has spread beyond the prostate, treatment options significantly change, so most doctors that treat prostate cancer use a variety of nomograms to predict the probability of spread. Treatment by watchful waiting/active surveillance, external beam radiation therapy, brachytherapy, cryosurgery, HIFU, and surgery are, in general, offered to men whose cancer remains within the prostate. Hormonal therapy and chemotherapy are often reserved for disease that has spread beyond the prostate. However, there are exceptions: radiation therapy may be used for some advanced tumors, and hormonal therapy is used for some early stage tumors. Cryotherapy (the process of freezing the tumor), hormonal therapy, and chemotherapy may also be offered if initial treatment fails and the cancer progresses.

If the disease has reached clinical stage T3 or T4, it is classified as advanced prostate cancer. Advanced prostate cancer with bone metastasis or lymph node metastasis is more likely to cause Prostate Cancer Symptoms than is an early stage of the disease. Doctors usually check for bone metastasis and lymph node metastasis which are denoted respectively by M and N in clinical staging.

In clinical stage T3, the tumor has extended beyond the prostatic capsule, possibly into the seminal vesicles, and is specifically called extraprostatic extension. Extraprostatic means "independent of the prostate gland." In clinical stage T4, the disease invades surrounding organs (other than the seminal vesicles) such as the bladder neck, external sphincter, or rectum.

Metastasis is more likely to occur during advanced prostate cancer. Metastatic disease refers to prostate cancer that has left the prostate gland and its neighboring organs. Advanced prostate cancer bone metastasis and lymph node metastasis, which can be local or distant, are both associated with advanced prostate cancer. Metastases may involve symptoms that are not in the Prostate Cancer Treatment Guide.

Prostate Cancer Lymph Node Metastasis The body produces a fluid called lymph which contains white blood cells and circulates through the lymphatic system. Lymph nodes are small oval or circular organs that filter this fluid. Cancerous cells that circulate through the body can become trapped in the lymph nodes. Once trapped, cancerous cells can begin their cycle of unhealthy division and result in lymph node metastasis.

There are two types of lymph node metastasis: local and distant. Local lymph node metastasis is designated by clinical stage N1. Two lymph nodes lie on either side of the bladder. Because these nodes are close to the prostate gland, metastasis is considered local. If cancerous cells begin to grow in any other lymph node, the metastasis is considered distant. Distant lymph node metastasis is denoted by clinical stage M1a.

Prostate Cancer Bone Metastasis Primary cases of bone cancer are relatively rare. Patients who develop bone cancer are more likely to develop the disease as a result of advanced prostate cancer metastasis. In prostate cancer, extension leading to bone disease is designated by a clinical stage M1b. If a person develops bone disease as a result of prostate cancer, he does not now have bone cancer. Because the cancer is classified according to where it originated, he has prostate cancer with bone metastasis.

Skeletal metastases occur in more than 80% of advanced-stage prostate cancer and they confer a high level of morbidity, a 5-year survival rate of 25% and median survival of approximately 40 months. Of the estimated one million annual deaths associated with metastatic bone disease in the USA, EU and Japan, approximately 20% are cases of advanced-stage prostate cancer. Treatment-naïve metastatic prostate cancer is largely sensitive to androgen-deprivation therapy but progression to castration-resistant prostate cancer occurs 18-20 months after starting treatment. Metastatic bone disease causes some of the most distressing symptoms of advanced-stage cancer; estimates indicate that treatment of bone pain is required in approximately 30% of men with castration resistant prostate cancer and associated with metastatic bone disease; with 22% requiring treatment for singular or multiple pathological skeletal fractures; 7% for spinal-cord compression; 3-4% for hemiparesis or paresis. At first diagnosis of bone metastasis disease therapeutic intervention will usually involve systemic chemotherapy, hormonal therapy and bisphophonates or Denosumab, which are mostly palliative options with the intention of reducing pain.

In healthy skeletal bone, an equal balance of new bone matrix formation and old bone matrix resorption is achieved via coordinated activity of bone-degrading osteoclasts and bone-forming osteoblasts. During metastasis bone disease, the normal balance of bone resorption and formation is disrupted by the homotypic and heterotypic cell-cell interactions that occur between invading tumor cells, osteoblasts and ostoclasts. Most patients with secondary bone tumors—including those associated with castration resistant prostate cancer-present with osteolytic lesions. Therefore, most treatment strategies in current use or under evaluation in metastatic bone disease have been designed to protect the bone matrix from increased bone degrading activity of osteoclasts. An additional complication that presents in more than 80% of men with castration-resistant prostate cancer and metastasis bone disease are osteosclerotic lesions—also known as bone-forming or osteoblastic lesions—or a combination of both, osteolytic and osteosclerotic lesions—also referred to as mixed lesions. Osteosclerotic lesions are typified by bone deposits with multiple layers of poorly organized type-I collagen fibrils that have a woven appearance and reduced mechanical strength.

Prostate cancer cells preserve, among each subtype, genome-aberration-induced transcriptional changes with high fidelity. The resulting dominant genes reveal molecular events that predict the metastatic outcome despite the existence of substantial genomic, transcriptional, translational, and biological heterogeneity in the overall system. However, it is unknown whether the developmental history of a cancer would result in different or common mediators of site-specific metastasis. Predisposing factors related to the cell of origin may engender different rate-limiting barriers during metastasic progression. Herein, we proposed the use of a new biomarker as a prognostic factor in primary tumors that predicts future bone metastasis events. Moreover, we also propose the use of this gene as a potential therapeutic target to prevent, stop and cure prostate cancer derived bone metastasis.

SUMMARY OF THE INVENTION

In one embodiment, the present invention relates to an in vitro method for the diagnosis of metastasis in a subject with prostate cancer and/or for the prognosis of the tendency to develop metastasis, relapse or recurrence in a subject with prostate cancer, said method comprising: (i) quantifying the c-MAF gene expression level in a prostate tumor sample of said subject and (ii) comparing the expression level obtained in (i) with the expression level of the c-MAF gene in a control sample, wherein the quantification of the c-MAF gene expression level comprises quantifying the messenger RNA (mRNA) of said gene, or a fragment of said mRNA, the complementary DNA (cDNA) of said gene, or a fragment of said cDNA or quantifying the levels of protein encoded by said gene, wherein if the expression level of the c-MAF gene in said tumor sample is increased with respect to the expression level of the c-MAF gene in the control sample, then said subject has a positive diagnosis for metastasis, relapse or recurrence or a greater tendency to develop metastasis, relapse or recurrence.

In one embodiment, the present invention relates to an in vitro method for designing a customized therapy for a subject with prostate cancer which comprises (i) quantifying the c-MAF gene expression level in a prostate tumor sample of said subject, and (ii) comparing the expression level obtained in (i) with the expression level of the c-MAF gene in a control sample, wherein the quantification of the c-MAF gene expression level comprises quantifying the messenger RNA (mRNA) of said gene, or a fragment of said mRNA, the complementary DNA (cDNA) of said gene, or a fragment of said cDNA or quantifying the levels of protein encoded by said gene, wherein if the expression level of the c-MAF gene in the tumor sample is increased with respect to the expression level of the c-MAF gene in the control sample, then said subject is susceptible to receive a therapy intended to prevent, inhibit and/or treat metastasis, relapse or recurrence of the cancer.

In some embodiments, the metastasis is bone metastasis. In certain embodiments, the bone metastasis is osteolytic metastasis.

In one embodiment, the present invention relates to an in vitro method for designing a customized therapy for a subject having prostate cancer with bone metastasis which comprises (i) quantifying the c-MAF gene expression level in a bone metastatic tumor tissue sample of said subject, and (ii) comparing the expression level obtained in step (i) with the expression level of the c-MAF gene in a control sample, wherein the quantification of the c-MAF gene expression level comprises quantifying the messenger RNA (mRNA) of said gene, or a fragment of said mRNA, the complementary DNA (cDNA) of said gene, or a fragment of said cDNA or quantifying the levels of protein encoded by said gene, wherein if the c-MAF gene expression level in the tumor tissue sample is increased with respect to the expression level of the c-MAF gene in the control sample, then said subject is susceptible to receive a therapy intended to prevent or inhibit bone degradation, wherein the agent intended to prevent or inhibit bone degradation is selected from the group consisting of: a bisphosphonate, a RANKL inhibitor, PTH, a PTHLH inhibitor (including neutralizing antibodies and peptides), a PRG analog, strontium ranelate, a DKK-1 inhibitor, a dual MET and VEGFR2 inhibitor, an estrogen receptor modulator, calcitonin, Radium-223, a CCR5 antagonist, a Src kinase inhibitor, a COX-2 inhibitor, an mTor inhibitor, and a cathepsin K inhibitor.

In an embodiment, the RANKL inhibitor is selected from the group consisting of: a RANKL specific antibody, a RANKL-specific nanobody, and osteoprotegerin. In a further embodiment, the RANKL specific antibody is denosumab. In a particular embodiment, the bisphosphonate is zoledronic acid. In one embodiment, the RANKL specific nanobody is ALX-0141. In a certain embodiment, the dual MET and VEGFR2 inhibitor is Cabozantinib.

In one embodiment, the expression level is quantified by means of a quantitative polymerase chain reaction (PCR) or a DNA or RNA array or nucleotide hybridization technique. In a different embodiment, wherein the level of protein is quantified by means of western blot, ELISA, immunohistochemistry or a protein array. In a particular embodiment, the level of protein is quantified using an antibody comprising a heavy chain CDR1 of SEQ ID NO: 21, and/or a heavy chain CDR2 of SEQ ID NO: 22, and/or a heavy chain CDR3 of SEQ ID NO: 23; and/or comprising a light chain CDR1 of SEQ ID NO: 18, and/or a light chain CDR2 of SEQ ID NO: 19 and/or a light chain CDR3 of SEQ ID NO: 20.

In one embodiment, the present invention relates to an in vitro method for diagnosing metastasis, relapse or recurrence in a subject with prostate cancer and/or for the prognosis of the tendency to develop metastasis, relapse or recurrence in a subject with prostate cancer which comprises determining if the c-MAF gene is amplified in a tumor sample of said subject relative to a reference gene copy number, wherein an amplification or gain of the c-MAF gene with respect to said reference gene copy number is indicative of the presence of metastasis, relapse or recurrence or an increased risk of developing metastasis, relapse or recurrence, wherein the amplification or gain of the c-MAF gene is determined by means of determining the amplification or gain of the locus 16q22-q24.

In an embodiment, the amplification of the c-MAF gene is determined by means of determining the amplification of the locus 16q22-q24. In one embodiment, the amplification or gain of the c-MAF gene is determined by means of using a c-MAF gene-specific probe. In a further embodiment, the c-MAF gene-specific probe is a Vysis LSI/IGH MAF Dual Color Dual Fusion Probe. In one embodiment, the reference gene copy number is that of a tumor tissue sample of prostate cancer from a subject who has not suffered metastasis. In an embodiment, the amplification or gain is determined by means of in situ hybridization or PCR.

In one embodiment, the metastasis is bone metastasis. In a further embodiment, the bone metastasis is osteolytic metastasis.

In one embodiment, the present invention relates to a method for treating and/or preventing bone metastasis, relapse or recurrence from prostate cancer comprising administering a c-MAF inhibitory agent selected from the group consisting of: a c-MAF specific siRNA, a c-MAF specific antisense oligonucleotide, a c-MAF specific ribozyme, a c-MAF inhibitory antibody or nanobody, a dominant negative c-MAF variant, a compound from Table 1 or from Table 2, a c-MAF specific small molecule, a c-MAF specific antibody, a c-MAF specific antibody-like molecule, a c-MAF specific structurally constrained (cyclical) peptide, a c-MAF specific stapled peptide, or a c-MAF specific alphabody.

In one embodiment, the present invention relates to a method for the treatment of bone metastasis and/or avoiding or preventing bone degradation in a subject suffering prostate cancer and having elevated c-MAF levels in a metastatic tumor sample with respect to a control sample comprising administering an agent capable of avoiding or preventing bone degradation, wherein the agent capable of avoiding or preventing bone degradation is selected from the group consisting of: a bisphosphonate, a RANKL inhibitor, PTH, PTHLH inhibitor (including neutralizing antibodies and peptides), a PRG analog, strontium ranelate, a DKK-1 inhibitor, a dual MET and VEGFR2 inhibitor, an estrogen receptor modulator, an EGFR inhibitor, calcitonin, Radium-223, a CCR5 antagonist, a Src kinase inhibitor, a COX-2 inhibitor, an mTor inhibitor, and a cathepsin K inhibitor.

In an embodiment, the RANKL inhibitor is selected from the group of: a RANKL specific antibody, a RANKL specific nanobody, and osteoprotegerin. In a particular embodiment, the RANKL specific antibody is denosumab. In another embodiment, the bisphosphonate is zoledronic acid.

In one embodiment, the RANKL specific nanobody is ALX-9141. In an embodiment, the dual MET and VEGFR2 inhibitor is Cabozantinib. In one embodiment, the bone metastasis is osteolytic metastasis.

In one embodiment, the present invention relates to a kit for predicting bone metastasis, relapse or recurrence of a prostate cancer in a subject suffering from said cancer, the kit comprising: a) means for quantifying the expression level of c-MAF in a tumor sample of said subject; and b) means for comparing the quantified level of expression of c-MAF in said sample to a reference c-MAF expression level.

In one embodiment, the present invention relates to an in vitro method for typing a sample of a subject suffering from prostate cancer, the method comprising: a) providing a sample from said subject; b) quantifying the expression level of c-MAF in said sample; c) typing said sample by comparing the quantified expression level of c-MAF to a predetermined reference level of c-MAF expression; wherein the quantification of the c-MAF expression level comprises quantifying the messenger RNA (mRNA) of said gene, or a fragment of said mRNA, the complementary DNA (cDNA) of said gene, or a fragment of said cDNA or quantifying the levels of protein encoded by said gene, wherein said typing provides prognostic information related to the risk of bone metastasis, relapse or recurrence in said subject.

In one embodiment, the present invention relates to a method for preventing, inhibiting or reducing the risk of bone metastasis, relapse or recurrence in a subject suffering from prostate cancer, said method comprising administering to said subject an agent that prevents or reduces bone metastasis, wherein said agent is administered in accordance with a treatment regimen determined from quantifying the expression level of c-MAF in said subject, wherein the quantification of the c-MAF expression level comprises quantifying the messenger RNA (mRNA) of said gene, or a fragment of said mRNA, the complementary DNA (cDNA) of said gene, or a fragment of said cDNA or quantifying the levels of protein encoded by said gene.

In one embodiment, the present invention relates to a method of classifying a subject suffering from prostate cancer into a cohort, comprising: a) determining the expression level of c-MAF in a prostate tumor sample of said subject; b) comparing the expression level of c-MAF in said sample to a predetermined reference level of c-MAF expression; and c) classifying said subject into a cohort based on said expression level of c-MAF in the sample, wherein the quantification of the c-MAF expression level comprises quantifying the messenger RNA (mRNA) of said gene, or a fragment of said mRNA, the complementary DNA (cDNA) of said gene, or a fragment of said cDNA or quantifying the levels of protein encoded by said gene.

In an embodiment, the level of protein is quantified using an antibody comprising a heavy chain CDR1 of SEQ ID NO: 21, and/or a heavy chain CDR2 of SEQ ID NO: 22, and/or a heavy chain CDR3 of SEQ ID NO: 23; and/or comprising a light chain CDR1 of SEQ ID NO: 18, and/or a light chain CDR2 of SEQ ID NO: 19 and/or a light chain CDR3 of SEQ ID NO: 20.

In one embodiment, the present invention relates to a kit for determining a therapy for a subject suffering from prostate cancer, the kit comprising: a) means for quantifying the expression level of c-MAF in a tumor sample of said subject; b) means for comparing the quantified expression level of c-MAF in said sample to a reference c-MAF expression level; and c) means for determining a therapy for preventing, inhibiting and/or reducing bone metastasis, relapse or recurrence in said subject based on the comparison of the quantified expression level to the reference expression level.

In one embodiment, the present invention relates to a kit comprising: i) a reagent for quantifying the expression level of c-MAF in a tumor sample of a subject suffering from prostate cancer, and ii) one or more c-MAF gene expression level indices that have been predetermined to correlate with the risk of bone metastasis, relapse or recurrence.

In an embodiment, the means for quantifying expression comprise a set of probes and/or primers that specifically bind and/or amplify the c-MAF gene, the 16q23 locus or the 16q22-16q24 chromosomal region or an antibody that specifically binds to a c-MAF epitope.

In one embodiment, the present invention relates to a in vitro method for typing a sample of a subject suffering from prostate cancer, the method comprising: (i) providing a tumor sample from said subject; (ii) quantifying the expression level of c-MAF in said sample; (iii) typing said sample by comparing the quantified expression level of c-MAF to a predetermined reference level of c-MAF expression; wherein the quantification of the c-MAF expression level comprises quantifying the messenger RNA (mRNA) of said gene, or a fragment of said mRNA, the complementary DNA (cDNA) of said gene, or a fragment of said cDNA or quantifying the levels of protein encoded by said gene, wherein said typing provides prognostic information related to the risk of bone metastasis, relapse or recurrence in said subject.

In one embodiment, the present invention relates to a method for preventing, inhibiting, or reducing the risk of bone metastasis, relapse or recurrence in a subject suffering from prostate cancer, said method comprising administering or not to said subject an agent that prevents or reduces bone metastasis, wherein said agent is administered in accordance with a treatment regimen determined at least in part from quantifying the expression level of c-MAF in said subject, wherein the quantification of the c-MAF expression level comprises quantifying the messenger RNA (mRNA) of said gene, or a fragment of said mRNA, the complementary DNA (cDNA) of said gene, or a fragment of said cDNA or quantifying the levels of protein encoded by said gene.

In one embodiment, the present invention relates to a method of classifying a subject suffering from prostate cancer into a cohort, comprising: a) determining the expression level of c-MAF in a cancer tumor sample of said subject; b) comparing the expression level of c-MAF in said sample to a predetermined reference level of c-MAF expression; and c) classifying said subject into a cohort based on said expression level of c-MAF in said sample, wherein the quantification of the c-MAF expression level comprises quantifying the messenger RNA (mRNA) of said gene, or a fragment of said mRNA, the complementary DNA (cDNA) of said gene, or a fragment of said cDNA or quantifying the levels of protein encoded by said gene.

In an embodiment, said cohort comprises at least one other individual who has been determined to have a comparable expression level of c-MAF in comparison to said reference expression level. In one embodiment, said expression level of c-MAF in said sample is increased relative to said predetermined reference level, and wherein members of the cohort are classified as having increased risk of bone metastasis, relapse or recurrence. In an embodiment, the cohort is for conducting a clinical trial.

In one embodiment, the present invention relates to an in vitro method for predicting bone metastasis, relapse or recurrence of prostate cancer in a subject suffering said cancer, said method comprising determining if the c-MAF gene is translocated in a tumor sample of said subject, wherein translocation of the c-MAF gene is indicative of an increased risk of bone metastasis, relapse or recurrence.

In one embodiment, the present invention relates to an in vitro method for designing a customized therapy for a subject having prostate cancer with bone metastasis, relapse or recurrence which comprises determining if the c-MAF gene is amplified in a tumor sample of said subject relative to a reference gene copy number, wherein an amplification or gain of the c-MAF gene with respect to said reference gene copy number indicates that the subject is a candidate for receiving a therapy intended to prevent or inhibit bone degradation, wherein the amplification or gain of the c-MAF gene is determined by means of determining the amplification or gain of the locus 16q22-q24, wherein the therapy intended to prevent or inhibit bone degradation is selected from the group consisting of: a bisphosphonate, a RANKL inhibitor, PTH, a PTHLH inhibitor (including neutralizing antibodies and peptides), a PRG analog, strontium ranelate, a DKK-1 inhibitor, a dual MET and VEGFR inhibitor, an estrogen receptor modulator, calcitonin, Radium-223, a CCR5 antagonist, a Src kinase inhibitor, a COX-2 inhibitor, an mTor inhibitor, and a cathepsin K inhibitor.

In some embodiments, the RANKL inhibitor is selected from the group consisting of: a RANKL specific antibody, a RANKL-specific nanobody, and osteoprotegerin. In an embodiment, the RANKL specific antibody is denosumab. In one embodiment, the bisphosphonate is zoledronic acid. In certain embodiments, said means for quantifying expression comprise a set of probes and/or primers that specifically bind and/or amplify the c-MAF gene, the 16q23 locus or the 16q22-16q24 chromosomal region or an antibody that specifically binds to a c-MAF epitope. In particular embodiments, said means for quantifying expression comprise a set of probes and/or primers that specifically bind and/or amplify the c-MAF gene, the 16q23 locus or the 16q22-16q24 chromosomal region or an antibody that specifically binds to a c-MAF epitope. In one embodiment, the antibody that specifically binds to a c-MAF epitope comprises a heavy chain CDR1 of SEQ ID NO: 21, and/or a heavy chain CDR2 of SEQ ID NO: 22, and/or a heavy chain CDR3 of SEQ ID NO: 23; and/or comprises a light chain CDR1 of SEQ ID NO: 18, and/or a light chain CDR2 of SEQ ID NO: 19 and/or a light chain CDR3 of SEQ ID NO: 20.

BRIEF DESCRIPTION OF THE DRAWINGS

FIG. 1. MAF drives bone metastasis in experimental breast cancer metastasis mouse models. A) Western blot depicting MAF protein levels in prostate cancer cell lines PCR, DU-145, LnCaP were tested. All wells were equally loaded with 25 micrograms of total protein. B) Kaplan-Meier curve of bone metastasis-free survival. Parental mock and MAF Short and MAF Long isoform (simultaneously) overexpressing DU-145 cells were injected into the left ventricle and metastasis was determined by bioluminescence. C) Representative bioluminescent images at endpoint of mice hind limbs for each group are shown. Total photon flux of ex vivo hind limbs was measured at endpoint and normalized to day 0. Log rank test was used.

DETAILED DESCRIPTION OF THE INVENTION

Methods for the Diagnosis and Prognosis of Prostate Cancer Metastasis Based on c-MAF Expression Levels The inventors have shown that the c-MAF gene and protein is overexpressed in Prostate cancer metastasis, and that the c-MAF expression levels in primary prostate tumors are correlated to different clinical parameters of prostate cancer, particularly with recurrence, relapse and metastasis probability. Thus, c-MAF overexpression is associated with the onset and high risk of prostate tumor metastasis, particularly in bone. Therefore, c-MAF can be used as a marker for the diagnosis and/or prognosis of metastasis, in particular bone metastasis, in a subject with Prostate cancer.

Thus in one aspect, the invention relates to an in vitro method for the diagnosis of metastasis, relapse or recurrence in a subject with Prostate cancer and/or for the prognosis of the tendency to develop metastasis, relapse or recurrence in a subject with Prostate cancer which comprises
(i) quantifying the c-MAF gene expression level in a tumor sample (e.g., prostate tumor tissue, circulating prostate tumor cell, circulating prostate tumor DNA) from said subject and
(ii) comparing the expression level previously obtained with the expression level of said gene in a control sample, wherein if the expression level of said gene are increased with respect to the expression level of said gene in the control sample, then said subject has a positive diagnosis for metastasis, relapse or recurrence or a greater tendency to develop metastasis, relapse or recurrence, in a preferred site bone metastasis.

The c-MAF gene (v-maf musculoaponeurotic fibrosarcoma oncogene homologue (avian) also known as MAF or MGC71685) is a transcription factor containing a leucine zipper which acts like a homodimer or a heterodimer. Depending on the DNA binding site, the encoded protein can be a transcriptional activator or repressor. The DNA sequence encoding c-MAF is described in the NCBI database under accession number NG_016440 (SEQ ID NO: 1) (coding)). The genomic sequence of c-MAF is set forth in SEQ ID NO:13. The methods of the present invention may utilize either the coding sequence or the genomic DNA sequence. Two messenger RNA are transcribed from said DNA sequence, each of the which will give rise to one of the two c-MAF protein isoforms, the α isoform and the β isoform. The complementary DNA sequences for each of said isoforms are described, respectively, in the NCBI database under accession numbers NM_005360.4 (SEQ ID NO: 2) and NM_001031804.2 (SEQ ID NO: 3). Use of the c-MAF gene to predict the prognosis of triple-negative and ER+ breast cancer is described in Int'l. Appl. No. PCT/IB2013/001204, which is incorporated herein by reference in its entirety. Use of the c-MAF gene to predict the prognosis of thyroid cancer is described in U.S. Prov. Appl.

No. 61/801,769, which is incorporated herein by reference in its entirety. Use of the c-MAF gene to predict the prognosis of renal cell carcinoma is described in U.S. Prov. Appl. No. 61/801,642, which is incorporated herein by reference in its entirety. The use of a gene of interest, including c-MAF and the c-MAF gene locus, to determine the prognosis of an individual suffering breast cancer is described in U.S. Prov. Appl. No. 61/801,718, which is incorporated herein by reference in its entirety. Use of the c-MAF gene to predict the prognosis of lung cancer is found in Int'l Appl. No. PCT/US2013/044584, which is incorporated herein by reference in its entirety.

In the context of the present invention, "metastasis" is understood as the propagation of a cancer from the organ where it started to a different organ. It generally occurs through the blood or lymphatic system. When the cancer cells spread and form a new tumor, the latter is called a secondary or metastatic tumor. The cancer cells forming the secondary tumor are like those of the original tumor. If a Prostate cancer, for example, spreads (metastasizes) to the bone, the secondary tumor is formed of malignant Prostate cancer cells. The disease in the bone is metastatic Prostate cancer and not bone cancer. In a particular embodiment of the method of the invention, the metastasis is Prostate cancer which has spread (metastasized) to the bone.

In the context of the present invention, "recurrence" refers to the return of prostate cancer following a period of time in which no cancer was detected. Prostate cancer may reoccur locally in the prostate or tissue surrounding the prostate. Prostate cancer may also reoccur in nearby lymph nodes or lymph nodes not in the surrounding area. When the prostate cancer reoccurs by spreading to other tissues or travels through the blood stream to recur in bones or other organs, it is also referred to as metastasis. As used herein, recurrence also encompasses the risk of recurrence.

In the context of the present invention, "relapse" refers to the situation when symptoms have decreased, but the subject is not cancer free, and then cancer returns. Prostate cancer may relapse locally in the prostate or tissue surrounding the prostate. Prostate cancer may also relapse in nearby lymph nodes or lymph nodes not in the surrounding area. When the prostate cancer relapses by spreading to other tissues or travels through the blood stream to recur in bones or other organs, it is also referred to as metastasis. As used herein, relapse also encompasses the risk of relapse.

In the present invention, "diagnosis of metastasis in a subject with Prostate cancer" is understood as identifying a disease (metastasis) by means of studying its signs, i.e., in the context of the present invention by means of increased c-MAF gene expression levels (i.e., overexpression) in the Prostate cancer tumor tissue with respect to a control sample.

In the present invention "prognosis of the tendency to develop metastasis in a subject with Prostate cancer" is understood as knowing based on the signs if the Prostate cancer that said subject has will metastasize in the future. In the context of the present invention, the sign is c-MAF gene overexpression in tumor tissue.

The method of the invention comprises in a first step quantifying the c-MAF gene expression level in a tumor tissue sample from a subject.

In a preferred embodiment, the first method of the invention comprises quantifying only the c-MAF gene expression level as a single marker, i.e., the method does not involve determining the expression level of any additional marker.

As used herein, the term "subject" or "patient" refers to all animals classified as mammals and includes but is not limited to domestic and farm animals, primates and humans, for example, human beings, non-human primates, cows, horses, pigs, sheep, goats, dogs, cats, or rodents. Preferably, the subject is a human man or woman of any age or race.

The terms "poor" or "good", as used herein to refer to a clinical outcome, mean that the subject will show a favourable or unfavourable outcome. As will be understood by those skilled in the art, such an assessment of the probability, although preferred to be, may not be correct for 100% of the subjects to be diagnosed. The term, however, requires that a statistically significant portion of subjects can be identified as having a predisposition for a given outcome. Whether a portion is statistically significant can be determined readily by the person skilled in the art using various well known statistic evaluation tools, e.g., determination of confidence intervals, p-value determination, Student's t-test, Mann-Whitney test, etc. Details are found in Dowdy and Wearden, Statistics for Research, John Wiley & Sons, New York 1983. Preferred confidence intervals are at least about 50%, at least about 60%, at least about 70%, at least about 80%, at least about 90% at least about 95%. The p-values are, preferably, 0.05, 0.01, 0.005, or 0.0001 or less. More preferably, at least about 60 percent, at least about 70 percent, at least about 80 percent or at least about 90 percent of the subjects of a population can be properly identified by the method of the present invention.

In the present invention "tumor sample" is understood as a sample (e.g., tumor tissue, circulating tumor cell, circulating tumor DNA) originating from the primary Prostate cancer tumor. Said sample can be obtained by conventional methods, for example biopsy, using methods well known by the persons skilled in related medical techniques. The methods for obtaining a biopsy sample include splitting a tumor into large pieces, or microdissection, or other cell separating methods known in the art. The tumor cells can additionally be obtained by means of cytology through aspiration with a small gauge needle. To simplify sample preservation and handling, samples can be fixed in formalin and soaked in paraffin or first frozen and then soaked in a tissue freezing medium such as OCT compound by means of immersion in a highly cryogenic medium which allows rapid freezing.

As understood by the person skilled in the art, the gene expression levels can be quantified by measuring the messenger RNA levels of said gene or of the protein encoded by said gene.

For this purpose, the biological sample can be treated to physically or mechanically break up the tissue or cell structure, releasing the intracellular components into an aqueous or organic solution for preparing nucleic acids. The nucleic acids are extracted by means of commercially available methods known by the person skilled in the art (Sambroock, J., et al., "Molecular cloning: a Laboratory Manual", 3rd ed., Cold Spring Harbor Laboratory Press, N.Y., Vol. 1-3.)

Thus, the c-MAF gene expression level can be quantified from the RNA resulting from the transcription of said gene (messenger RNA or mRNA) or, alternatively, from the complementary DNA (cDNA) of said gene. Therefore, in a particular embodiment of the invention, the quantification of the c-MAF gene expression levels comprises the quantification of the messenger RNA of the c-MAF gene or a fragment of said mRNA, complementary DNA of the c-MAF gene or a fragment of said cDNA or the mixture thereof.

Virtually any conventional method can be used within the scope of the invention for detecting and quantifying the mRNA levels encoded by the c-MAF gene or of the corresponding cDNA thereof. By way of non-limiting illustration, the mRNA levels encoded by said gene can be quantified using conventional methods, for example, methods comprising mRNA amplification and the quantification of said mRNA amplification product, such as electrophoresis and staining, or alternatively, by Southern blot and using suitable probes, Northern blot and using specific probes of the mRNA of the gene of interest (c-MAF) or of the corresponding cDNA thereof, mapping with 51 nuclease, RT-PCR, hybridization, microarrays, etc., preferably by means of real time quantitative PCR using a suitable marker. Likewise, the cDNA levels corresponding to said mRNA encoded by the c-MAF gene can also be quantified by means of using conventional techniques; in this case, the method of the invention includes a step for synthesizing the corresponding cDNA by means of reverse transcription (RT) of the corresponding mRNA followed by the amplification and quantification of said cDNA amplification product. Conventional methods for quantifying expression levels can be found, for example, in Sambrook et al., 2001. (cited ad supra). These methods are known in the art and a person skilled in the art would be familiar with the normalizations necessary for each technique. For example, the expression measurements generated using multiplex PCR should be normalized by comparing the expression of the genes being measured to so called "housekeeping" genes, the expression of which should be constant over all samples, thus providing a baseline expression to compare against or other control genes whose expression are known to be modulated with cancer.

In a particular embodiment, the c-MAF gene expression levels are quantified by means of quantitative polymerase chain reaction (PCR) or a DNA, RNA array, or nucleotide hybridization technique.

In addition, the c-MAF gene expression level can also be quantified by means of quantifying the expression levels of the protein encoded by said gene, i.e., the c-MAF protein (c-MAF) [NCBI, accession number 075444], or any functionally equivalent variant of the c-MAF protein. There are two c-MAF protein isoforms, the a isoform (NCBI, NP_005351.2) made up of 403 amino acids (SEQ ID NO: 4) and the 0 isoform (NP_001026974.1) made up of 373 amino acids (SEQ ID NO: 5). The c-MAF gene expression level can be quantified by means of quantifying the expression levels of any of the c-MAF protein isoforms. Thus, in a particular embodiment, the quantification of the levels of the protein encoded by the c-MAF gene comprises the quantification of the c-MAF protein.

In the context of the present invention, "functionally equivalent variant of the c-MAF protein" is understood as (i) variants of the c-MAF protein (SEQ ID NO: 4 or SEQ ID NO: 5) in which one or more of the amino acid residues are substituted by a conserved or non-conserved amino acid residue (preferably a conserved amino acid residue), wherein such substituted amino acid residue may or may not be one encoded by the genetic code, or (ii) variants comprising an insertion or a deletion of one or more amino acids and having the same function as the c-MAF protein, i.e., to act as a DNA binding transcription factor. Variants of the c-MAF protein can be identified using methods based on the capacity of c-MAF for promoting in vitro cell proliferation as shown in international patent application WO2005/046731(hereby incorporated by reference in its entirety), based on the capacity of the so-called inhibitor for blocking the transcription capacity of a reporter gene under the control of cyclin D2 promoter or of a promoter containing the c-MAF responsive region (MARE or c-MAF responsive element) in cells expressing c-MAF as described in WO2008098351 (hereby incorporated by reference in its entirety), or based on the capacity of the so-called inhibitor for blocking reporter gene expression under the control of the IL-4 promoter in response to the stimulation with PMA/ionomycin in cells expressing NFATc2 and c-MAF as described in US2009048117A (hereby incorporated by reference in its entirety).

The variants according to the invention preferably have sequence similarity with the amino acid sequence of any of the c-MAF protein isoforms (SEQ ID NO: 4 or SEQ ID NO: 5) of at about least 50%, at least about 60%, at about least 70%, at least about 80%, at least about 90%, at least about 91%, at least about 92%, at least about 93%, at least about 94%, at least about 95%, at least about 96%, at least about 97%, at about least 98% or at about least 99%. The degree of similarity between the variants and the specific c-MAF protein sequences defined previously is determined using algorithms and computer processes which are widely known by the persons skilled in the art. The similarity between two amino acid sequences is preferably determined using the BLASTP algorithm [BLAST Manual, Altschul, S., et al., NCBI NLM NIH Bethesda, Md. 20894, Altschul, S., et al., J. Mol. Biol. 215: 403-410 (1990)].

The c-MAF protein expression level can be quantified by any conventional method which allows detecting and quantifying said protein in a sample from a subject. By way of non-limiting illustration, said protein levels can be quantified, for example, by using antibodies with c-MAF binding capacity (or a fragment thereof containing an antigenic determinant) and the subsequent quantification of the complexes formed. The antibodies used in these assays may or may not be labeled. Illustrative examples of markers that can be used include radioactive isotopes, enzymes, fluorophores, chemiluminescence reagents, enzyme substrates or cofactors, enzyme inhibitors, particles, dyes, etc. There is a wide range of known assays that can be used in the present invention which use unlabeled antibodies (primary antibody) and labeled antibodies (secondary antibody); these techniques include Western-blot or Western transfer, ELISA (enzyme-linked immunosorbent assay), RIA (radioimmunoassay), competitive EIA (competitive enzyme immunoassay), DAS-ELISA (double antibody sandwich ELISA), immunocytochemical and immunohistochemical techniques, techniques based on the use of protein microarrays or biochips including specific antibodies or assays based on colloidal precipitation in formats such as dipsticks. Other ways for detecting and quantifying said c-MAF protein include affinity chromatography techniques, ligand binding assays, etc. When an immunological method is used, any antibody or reagent that is known to bind to the c-MAF protein with a high affinity can be used for detecting the amount thereof. This would include, but is not limited to, the use of an antibody, for example, polyclonal sera, supernatants of hybridomas or monoclonal antibodies, antibody fragments, Fv, Fab, Fab' and F(ab')2, scFv, humanized diabodies, triabodies, tetrabodies, antibodies, nanobodies, alphabodies, stapled peptides, and cyclopeptides. There are commercial anti-c-MAF protein antibodies on the market which can be used in the context of the present invention, such as for example antibodies ab427, ab55502, ab55502, ab72584, ab76817, ab77071 (Abcam plc, 330 Science Park, Cambridge CB4 0FL, United Kingdom), the 075444 monoclonal antibody (Mouse Anti-Human MAF Azide free Monoclonal antibody, Unconjugated, Clone 6b8) of AbD Serotec, etc. There are many commercial companies offering anti-c-MAF antibodies, such as Abnova Corporation, Bethyl Laboratories, Bioworld Technology, GeneTex, etc.

In some embodiments, the c-MAF protein levels are detected by an antigen binding member or fragment thereof. In some embodiments, the binding member is an antigen binding molecule or fragment thereof that binds to human c-MAF. In some embodiments, the antibody binding molecule or fragment thereof comprises a heavy chain CDR1 at least about 70%, about 75%, about 80%, about 85%, about 90%, about 95%, about 99% or about 100% identical to the amino acid sequence of SEQ ID NO: 21, and/or a heavy chain CDR2 at least about 70%, about 75%, about 80%, about 85%, about 90%, about 95%, about 99% or about 100% identical to the amino acid sequence of SEQ ID NO: 22, and/or a heavy chain CDR3 at least about 70%, about 75%, about 80%, about 85%, about 90%, about 95%, about 99% or about 100% identical to the amino acid sequence of SEQ ID NO: 23; and/or comprising a light chain CDR1 at least about 70%, about 75%, about 80%, about 85%, about 90%, about 95%, about 99% or about 100% identical to the amino acid sequence of SEQ ID NO: 18, and/or a light chain CDR2 at least about 70%, about 75%, about 80%, about 85%, about 90%, about 95%, about 99% or about 100% identical to the amino acid sequence of SEQ ID NO: 19 and/or a light chain CDR3 at least about 70%, about 75%, about 80%, about 85%, about 90%, about 95%, about 99% or about 100% identical to the amino acid sequence of SEQ ID NO: 20.

In some embodiments, the antibody or fragment thereof comprises a $V_H$ domain with a sequence that is at least about 70%, at least about 75%, at least about 80%, at least about 85%, at least about 90%, at least about 95%, at least about 99%, at least about 99%, or at least about 100% identical to the amino acid sequence of SEQ ID NO: 15.

In some embodiments, the antigen binding molecule or fragment thereof comprises a $V_L$ domain with a sequence that is at least about 70%, at least about 75%, at least about 80%, at least about 85%, at least about 90%, at least about 95%, at least about 99%, at least about 99%, or at least about 100% identical to the amino acid sequence of SEQ ID NO: 17.

In some embodiments, the antibody or fragment thereof comprises a heavy chain sequence that is at least about 70%, at least about 75%, at least about 80%, at least about 85%, at least about 90%, at least about 95%, at least about 99%, at least about 99%, or at least about 100% identical to the amino acid sequence of SEQ ID NO: 14.

In some embodiments, the antibody or fragment thereof comprises a light chain sequence that is at least about 70%, at least about 75%, at least about 80%, at least about 85%, at least about 90%, at least about 95%, at least about 99%, at least about 99%, or at least about 100% identical to the amino acid sequence of SEQ ID NO: 16.

In some embodiments, the antigen binding molecule or fragment thereof is an antibody. In some embodiments, the antibody is a rabbit antibody, a mouse antibody, a chimeric antibody or a humanized antibody. In one aspect, the present invention is directed to a binding member, functional fragment, antibody or variant thereof that specifically binds to the epitope encoded by SEQ ID NO: 24. In some embodiments, the antibody is any antibody described in Int'l. Appl. No. PCT/IB2015/059562, which is incorporated herein by reference in its entirety.

In a particular embodiment, the c-MAF protein levels are quantified means of western blot, immunohistochemistry, ELISA or a protein array.

The first method of the invention comprises in a second step comparing the c-MAF gene expression level obtained in the tumor sample (including but not limited to a primary tumor biopsy, circulating tumor cells and circulating tumor DNA) from the subject with the expression level of said gene in a control sample.

Once the c-MAF gene expression level in a tumor tissue sample, a circulating tumor cell or circulating tumor DNA from a subject with prostate cancer has been measured and compared with the control sample, if the expression level of said gene is increased with respect to its expression level in the control sample, then it can be concluded that said subject has a positive diagnosis for metastasis or a greater tendency to develop metastasis.

The determination of the c-MAF gene expression level must be correlated with values of a control sample or reference sample. Depending on the type of tumor to be analyzed, the exact nature of the control sample may vary. Thus, in the event that a diagnosis is to be evaluated, then the reference sample is a tumor tissue sample from a subject with prostate cancer that has not metastasized or that corresponds to the median value of the c-MAF gene expression levels measured in a tumor tissue collection in biopsy samples from subjects with prostate cancer which have not metastasized.

Said reference sample is typically obtained by combining equal amounts of samples from a subject population. Generally, the typical reference samples will be obtained from subjects who are clinically well documented and in whom the absence of metastasis is well characterized. In such samples, the normal concentrations (reference concentration) of the biomarker (c-MAF gene) can be determined, for example by providing the mean concentration over the reference population. Various considerations are taken into account when determining the reference concentration of the marker. Among such considerations are the age, weight, sex, general physical condition of the patient and the like. For example, equal amounts of a group of at least about 2, at least about 10, at least about 100 to preferably more than 1000 subjects, preferably classified according to the foregoing considerations, for example according to various age categories, are taken as the reference group. The sample collection from which the reference level is derived will preferably be formed by subjects suffering from the same type of cancer as the patient object of the study (e.g., prostate cancer). Similarly, the reference value within a cohort of patients can be established using a receiving operating curve (ROC) and measuring the area under the curve for all de sensitivity and specificity pairs to determine which pair provides the best values and what the corresponding reference value is. ROC is a standard statistical concept. A description can be found in Stuart G. Baker "The Central Role of Receiver Operating Characteristic (ROC) curves in Evaluating Tests for the Early Detection of Cancer" *Journal of The National Cancer Institute* (2003) Vol 95, No. 7, 511-515.

Once this median or reference value has been established, the level of this marker expressed in tumor tissues from patients with this median value can be compared and thus be assigned to the "increased" expression level. Due to the variability among subjects (for example, aspects referring to age, race, etc.) it is very difficult (if not virtually impossible) to establish absolute reference values of c-MAF expression. Thus, in particular embodiments the reference values for "increased" or "reduced" expression of the c-MAF expression are determined by calculating the percentiles by conventional means which involves performing assays in one or several samples isolated from subjects whose disease is well documented by any of the methods mentioned above the c-MAF expression levels. The "reduced" levels of c-MAF can then preferably be assigned to samples wherein the c-MAF expression levels are equal to or lower than $50^{th}$ percentile in the normal population including, for example, expression levels equal to or lower than the $60^{th}$ percentile in the normal population, equal to or lower than the $70^{th}$ percentile in the normal population, equal to or lower than the $80^{th}$ percentile in the normal population, equal to or lower than the $90^{th}$ percentile in the normal population, and equal to or lower than the $95^{th}$ percentile in the normal population. The "increased" c-MAF gene expression levels can then preferably be assigned to samples wherein the c-MAF gene expression levels are equal to or greater than the $50^{th}$ percentile in the normal population including, for example, expression levels equal to or greater than the $60^{th}$ percentile in the normal population, equal to or greater than the $70^{th}$ percentile in the normal population, equal to or greater than the $80^{th}$ percentile in the normal population, equal to or greater than the $90^{th}$ percentile in the normal population, and equal to or greater than the $95^{th}$ percentile in the normal population.

In the present invention "increased expression levels" or "increased expression level" is understood as the expression level when it refers to the levels of the c-MAF gene greater than those in a reference sample or control sample. Particularly, a sample can be considered to have high c-MAF expression levels when the expression levels in the reference sample are at least about 1.1 times, 1.5 times, 5 times, 10 times, 20 times, 30 times, 40 times, 50 times, 60 times, 70 times, 80 times, 90 times, 100 times or even more with respect to the sample isolated from the patient.

In the context of the present invention, it is understood that "a subject has a positive diagnosis for metastasis" when the Prostate cancer suffered by said subject has metastasized to other organs of the body, in a particular embodiment, to the bone. The term is similarly used for recurrence and relapse.

In yet another embodiment, the metastasis to bone is an osteolytic bone metastasis. As used herein, the expression "osteolytic bone metastasis" refers to a type of metastasis in which bone resorption (progressive loss of the bone density) is produced in the proximity of the metastasis resulting from the stimulation of the osteoclast activity by the tumor cells and is characterized by severe pain, pathological fractures, hypercalcaemia, spinal cord compression and other syndromes resulting from nerve compression.

On the other hand, it is understood in the present invention that "a subject has a greater tendency to develop metastasis" when the probabilities that the Prostate cancer suffered by the subject will metastasize in the future are high. The term is similarly used for recurrence and relapse.

The person skilled in the art will understand that the prediction of the tendency for a primary prostate tumor to metastasize, relapse or reoccur is not intended to be correct for all the subjects to be identified (i.e., for 100% of the subjects). Nevertheless, the term requires enabling the identification of a statistically significant part of the subjects (for example, a cohort in a cohort study). Whether a part is statistically significant can be determined in a simple manner by the person skilled in the art using various well known statistical evaluation tools, for example, the determination of confidence intervals, determination of p values, Student's T test, Mann-Whitney test, etc. Details are provided in Dowdy and Wearden, Statistics for Research, John Wiley and Sons, New York 1983. The preferred confidence intervals are at least about 90%, at least about 95%, at least about 97%, at least 98% or at least 99%. The p values are preferably 0.1, 0.05, 0.01, 0.005 or 0.0001. More preferably, at least about 60%, at least about 70%, at least about 80% or at least about 90% of the subjects of a population can be suitably identified by the method of the present invention.

As used herein, "agent for avoiding or preventing bone degradation" refers to any molecule capable of preventing, inhibiting, treating, reducing, or stopping bone degradation either by stimulating the osteoblast proliferation or inhibiting the osteoclast proliferation or fixing the bone structure.

As used herein, a "c-MAF inhibitory agent" refers to any molecule capable of completely or partially inhibiting the c-MAF gene expression, both by preventing the expression product of said gene from being produced (interrupting the c-MAF gene transcription and/or blocking the translation of the mRNA coming from the c-MAF gene expression) and by directly inhibiting the c-MAF protein activity. C-MAF gene expression inhibitors can be identified using methods based on the capacity of the so-called inhibitor to block the capacity of c-MAF to promote the in vitro cell proliferation, such as shown in the international patent application WO2005/046731 (the entire contents of which are hereby incorporated by reference), based on the capacity of the so-called inhibitor to block the transcription capacity of a reporter gene under the control of the cyclin D2 promoter or of a promoter containing the c-MAF response region (MARE or c-MAF responsive element) in cells which express c-MAF such as described in WO2008098351 (the entire contents of which are hereby incorporated by reference) or based on the capacity of the so-called inhibitor to block the expression of a reporter gene under the control of the IL-4 promoter in response to the stimulation with PMA/ionomycin in cells which express NFATc2 and c-MAF such as described in US2009048117A (the entire contents of which is hereby incorporated by reference).

As used herein, Mammalian target of rapamycin (mTOR) or "mTor" refers to those proteins that correspond to EC 2.7.11.1. mTor enzymes are serine/threonine protein kinases and regulate cell proliferation, cell motility, cell growth, cell survival, and transcription.

As used herein, an "mTor inhibitor" refers to any molecule capable of completely or partially inhibiting the mTor gene expression, both by preventing the expression product of said gene from being produced (interrupting the mTor gene transcription and/or blocking the translation of the mRNA coming from the mTor gene expression) and by directly inhibiting the mTor protein activity. Including inhibitors that have a dual or more targets and among them mTor protein activity.

As used herein, "Src" refers to those proteins that correspond to EC 2.7.10.2. Src is a non-receptor tyrosine kinase and a proto-oncogene. Src may play a role in cell growth and embryonic development.

As used herein, a "Src inhibitor" refers to any molecule capable of completely or partially inhibiting the Src gene expression, both by preventing the expression product of said gene from being produced (interrupting the Src gene transcription and/or blocking the translation of the mRNA coming from the Src gene expression) and by directly inhibiting the Src protein activity.

As used herein, "Prostaglandin-endoperoxide synthase 2", "cyclooxygenase-2" or "COX-2" refers to those proteins that correspond to EC 1.14.99.1. COX-2 is responsible for converting arachidonic acid to prostaglandin endoperoxide H2.

As used herein, a "COX-2 inhibitor" refers to any molecule capable of completely or partially inhibiting the COX-2 gene expression, both by preventing the expression product of said gene from being produced (interrupting the COX-2 gene transcription and/or blocking the translation of the mRNA coming from the COX-2 gene expression) and by directly inhibiting the COX-2 protein activity.

As used herein "outcome" or "clinical outcome" refers to the resulting course of disease and/or disease progression and can be characterized for example by recurrence, period of time until recurrence, relapse, metastasis, period of time until metastasis, number of metastases, number of sites of metastasis and/or death due to disease. For example a good clinical outcome includes cure, prevention of recurrence, prevention of metastasis and/or survival within a fixed period of time (without recurrence), and a poor clinical outcome includes disease progression, metastasis and/or death within a fixed period of time.

"Predicting", as used herein, refers to the determination of the likelihood that the subject suffering lung cancer will develop metastasis, relapse or recurrence to a distant organ. As used herein, "good prognosis" indicates that the subject is expected (e.g. predicted) to survive and/or have no, or is at low risk of having, recurrence, relapse or distant metastases within a set time period. The term "low" is a relative term and, in the context of this application, refers to the risk of the "low" expression group with respect to a clinical outcome (recurrence, distant metastases, etc.). A "low" risk can be considered as a risk lower than the average risk for an heterogeneous cancer patient population. In the study of Paik et al. (2004), an overall "low" risk of recurrence was considered to be lower than 15 percent. The risk will also vary in function of the time period. The time period can be, for example, five years, ten years, fifteen years or even twenty years after initial diagnosis of cancer or after the prognosis was made.

As used herein, "poor prognosis" indicates that the subject is expected e.g. predicted to not survive and/or to have, or is at high risk of having, recurrence, relapse, or distant metastases within a set time period. The term "high" is a relative term and, in the context of this application, refers to the risk of the "high" expression group with respect to a clinical outcome (recurrence, distant metastases, etc.). A "high" risk can be considered as a risk higher than the average risk for a heterogeneous cancer patient population. In the study of Paik et al. (2004), an overall "high" risk of recurrence was considered to be higher than 15 percent. The risk will also vary in function of the time period. The time period can be, for example, five years, ten years, fifteen years or even twenty years of initial diagnosis of cancer or after the prognosis was made.

"Reference value", as used herein, refers to a laboratory value used as a reference for values/data obtained by laboratory examinations of patients or samples collected from patients. The reference value or reference level can be an absolute value; a relative value; a value that has an upper and/or lower limit; a range of values; an average value; a median value, a mean value, or a value as compared to a particular control or baseline value. A reference value can be based on an individual sample value, such as for example, a value obtained from a sample from the subject being tested, but at an earlier point in time. The reference value can be based on a large number of samples, such as from a population of subjects of the chronological age matched group, or based on a pool of samples including or excluding the sample to be tested.

The term "treatment", as used herein, refers to any type of therapy, which aims at terminating, preventing, ameliorating or reducing the susceptibility to a clinical condition as described herein. In a preferred embodiment, the term treatment relates to prophylactic treatment (i.e. a therapy to reduce the susceptibility to a clinical condition), of a disorder or a condition as defined herein. Thus, "treatment," "treating," and their equivalent terms refer to obtaining a desired pharmacologic or physiologic effect, covering any treatment of a pathological condition or disorder in a mammal, including a human. The effect may be prophylactic in terms of completely or partially preventing a disorder or symptom thereof and/or may be therapeutic in terms of a partial or complete cure for a disorder and/or adverse effect attributable to the disorder. That is, "treatment" includes (1) preventing the disorder from occurring or recurring in a subject, (2) inhibiting the disorder, such as arresting its development, (3) stopping or terminating the disorder or at least symptoms associated therewith, so that the host no longer suffers from the disorder or its symptoms, such as causing regression of the disorder or its symptoms, for example, by restoring or repairing a lost, missing or defective function, or stimulating an inefficient process, or (4) relieving, alleviating, or ameliorating the disorder, or symptoms associated therewith, where ameliorating is used in a broad sense to refer to at least a reduction in the magnitude of a parameter, such as inflammation, pain, or immune deficiency.

As used herein, "sample" or "biological sample" means biological material isolated from a subject. The biological sample may contain any biological material suitable for determining the expression level of the c-MAF gene. The sample can be isolated from any suitable biological tissue or fluid such as, for example, tumor tissue, blood, blood plasma, serum, urine or cerebral spinal fluid (CSF).

As used herein, the term "expression level" of a gene as used herein refers to the measurable quantity of gene product produced by the gene in a sample of the subject, wherein the gene product can be a transcriptional product or a translational product. Accordingly, the expression level can pertain to a nucleic acid gene product such as mRNA or cDNA or a polypeptide gene product. The expression level is derived from a subject's sample and/or a reference sample or samples, and can for example be detected de novo or correspond to a previous determination. The expression level can be determined or measured, for example, using microarray methods, PCR methods (such as qPCR), and/or antibody based methods, as is known to a person of skill in the art.

As used herein, the term "gene copy number" refers to the copy number of a nucleic acid molecule in a cell. The gene copy number includes the gene copy number in the genomic (chromosomal) DNA of a cell. In a normal cell (non-tumoral cell), the gene copy number is normally two copies (one copy in each member of the chromosome pair). The gene copy number sometimes includes half of the gene copy number taken from samples of a cell population. "Increased expression level" is understood as the expression level when it refers to the levels of the c-MAF gene greater than those in a reference sample or control sample. This increased levels can be caused without excluding other mechanisms by a gene or 16q23 or 16q22-24 chromosomal locus amplification, copy gain or translocation. Particularly, a sample can be considered to have high c-MAF expression level when the expression level in the sample isolated from the patient is at least about 1.1 times, 1.2 times, 1.3 times, 1.4 times, 1.5 times, 2 times, 3 times, 4 times, 5 times, 10 times, 20 times, 30 times, 40 times, 50 times, 60 times, 70 times, 80 times, 90 times, 100 times or even more with respect to the reference or control.

"Decreased expression level" is understood as the expression level when it refers to the levels of the c-MAF gene less than those in a reference sample or control sample. This decreased level can be caused without excluding other mechanisms by a gene or 16q23 or 16q22-24 chromosomal locus deletion. Particularly, a sample can be considered to have decreased c-MAF expression levels when the expression level in the sample isolated from the patient is at least about 1.1 times, 1.2 times, 1.3 times, 1.4 times, 1.5 times, 2 times, 3 times, 4 times, 5 times, 10 times, 20 times, 30 times, 40 times, 50 times, 60 times, 70 times, 80 times, 90 times, 100 times or even less with respect to the reference or control. In embodiments, a "decreased expression level" is a "low" expression level.

"Probe", as used herein, refers to an oligonucleotide sequence that is complementary to a specific nucleic acid sequence of interest. In some embodiments, the probes may be specific to regions of chromosomes which are known to undergo translocations. In some embodiments, the probes have a specific label or tag. In some embodiments, the tag is a fluorophore. In some embodiments, the probe is a DNA in situ hybridization probe whose labeling is based on the stable coordinative binding of platinum to nucleic acids and proteins. In some embodiments, the probe is described in U.S. patent application Ser. No. 12/067,532 and U.S. patent application Ser. No. 12/181,399, which are incorporated by reference in their entirety, or as described in Swennenhuis et al. "Construction of repeat-free fluorescence in situ hybridization probes" Nucleic Acids Research 40(3):e20 (2012).

"Tag" or "label", as used herein, refers to any physical molecule which is directly or indirectly associated with a probe, allowing the probe or the location of the probed to be visualized, marked, or otherwise captured.

"Translocation", as used herein, refers to the exchange of chromosomal material in unequal or equal amounts between chromosomes. In some cases, the translocation is on the same chromosome. In some cases, the translocation is between different chromosomes. Translocations occur at a high frequency in many types of cancer, including breast cancer and leukemia. Translocations can be either primary reciprocal translocations or the more complex secondary translocations. There are several primary translocations that involve the immunoglobin heavy chain (IgH) locus that are believed to constitute the initiating event in many cancers. (Eychène, A., Rocques, N., and Puoponnot, C., A new MAFia in cancer. 2008. Nature Reviews: Cancer. 8: 683-693.)

"Polyploid" or "polyploidy", as used herein, indicates that the cell contains more than two copies of a gene of interest. In some instances, the gene of interest is MAF. In some embodiments, polyploidy is associated with an accumulation of expression of the gene of interest. In some embodiments, polyploidy is associated with genomic instability. In some embodiments, the genomic instability may lead to chromosome translocations.

"Whole genome sequencing", as used herein, is a process by which the entire genome of an organism is sequenced at a single time. See, e.g., Ng., P. C. amd Kirkness, E. F., Whole Genome Sequencing. 2010. Methods in Molecular Biology. 628: 215-226.

"Exome sequencing", as used herein, is a process by which the entire coding region of the DNA of an organism is sequenced. In exome sequencing, the mRNA is sequenced. The untranslated regions of the genome are not included in exome sequencing. See, e.g., Choi, M. et al., Genetic diagnosis by whole exome capture and massively parallel DNA sequencing. 2009. PNAS. 106(45): 19096-19101.

"Tumor tissue sample" is understood as the tissue sample originating from the prostate cancer tumor, including but not limited to circulating tumor cells and circulating tumor DNA. Said sample can be obtained by conventional methods, for example biopsy, using methods well known by the persons skilled in related medical techniques.

"Osteolytic bone metastasis" refers to a type of metastasis in which bone resorption (progressive loss of the bone density) is produced in the proximity of the metastasis resulting from the stimulation of the osteoclast activity by the tumor cells and is characterized by severe pain, pathological fractures, hypercalcaemia, spinal cord compression and other syndromes resulting from nerve compression.

Method for Designing Customized Therapy of the Invention in Patients with Prostate Tumors As is known in the state of the art, the treatment to be administered to a subject suffering from cancer depends on whether the latter is a malignant tumor, i.e., whether it has high probabilities of undergoing metastasis, relapse, or recurrence or whether the latter is a benign tumor. In the first assumption, the treatment of choice is a systemic treatment such as chemotherapy and in the second assumption, the treatment of choice is a localized treatment such as radiotherapy.

Therefore, as described in the present invention, given that the c-MAF gene overexpression in prostate cancer cells is related to the presence of metastasis, relapse or recurrence the c-MAF gene expression levels allow making decisions in terms of the most suitable therapy for the subject suffering said cancer.

Thus, in another aspect the invention relates to an in vitro method for designing a customized therapy for a subject with prostate cancer, which comprises
(i) quantifying the c-MAF gene expression level in a tumor sample of said subject and
(ii) comparing the expression level previously obtained with the expression level of said gene in a control sample, wherein if the expression level are increased with respect to the expression levels of said gene in the control sample, then said subject is susceptible to receive a therapy aiming to prevent and/or treat the metastasis, relapse or recurrence. In a particular aspect of this method, the subject is then administered at least one therapeutic drug that prevents, inhibits and/or treats the bone metastasis, relapse or recurrence.

In some embodiments, if the c-MAF gene expression level is not increased with respect to said reference value, then said subject is not susceptible to receive a therapy for preventing the bone degradation and/or bone metastasis, relapse or recurrence. In a particular aspect of this method, the subject is then not administered at least one therapeutic drug that prevents, inhibits and/or treats the bone metastasis, relapse or recurrence.

In certain embodiments, if a high risk of reoccurrence is predicted based on the c-MAF level, the subject is susceptible to radical prostatectomy and radiation treatment. In other embodiments, if a low risk of reoccurrence is predicted based on the c-MAF level, the subject may be offered radical prostatectomy but not radiation treatment (adjuvant radiotherapy).

In a particular embodiment, the metastasis is a bone metastasis. In a more preferred embodiment, the bone metastasis is osteolytic metastasis.

The terms and expressions "subject", "prostate cancer", "tumor sample", "metastasis", "determination of expression levels", "c-MAF gene", "increased expression levels", "recurrence", and "relapse" and "control sample" have been described in detail in relation to the first method of the invention and are equally applicable to the second and third method of the invention.

The second method of the invention comprises in a first step quantifying the c-MAF gene expression level in a tumor sample in a subject suffering from prostate cancer.

In a preferred embodiment, the second method of the invention comprises quantifying only the c-MAF gene expression level as a single marker, i.e., the method does not involve determining the expression level of any additional marker.

In the case of the second method of the invention the sample is a primary tumor tissue sample of the subject. In a second step, the c-MAF gene expression level obtained in the tumor sample of the subject is compared with the expression level of said gene in a control sample. The determination of the c-MAF gene expression levels must be related to values of a control sample or reference sample. Depending on the type of tumor to be analyzed, the exact nature of the control sample may vary. Thus preferably the reference sample is a tumor tissue sample of a subject with prostate cancer that has not metastasized, relapsed or reoccurred or that corresponds to the median value of the c-MAF gene expression levels measured in a tumor tissue collection in biopsy samples of subjects with prostate cancer which has not metastasized, relapsed or reoccurred.

In yet another embodiment, an expression level of c-MAF which is above the average indicates increased risk of bone metastasis, relapse or recurrence the risk being proportional to the levels of c-MAF expression, Thus, the risk of bone metastasis, relapse or recurrence in a subject suffering lung cancer is dose-dependent.

Once the c-MAF gene expression level in the sample have been measured and compared with the control sample, if the expression level of said gene are increased with respect to their expression levels in the control sample, then it can be concluded that said subject is susceptible to receiving therapy aiming to prevent (if the subject has yet to undergo metastasis) and/or treat metastasis (if the subject has already experienced metastasis), relapse or recurrence. If such increased expression is not observed then the subject is not administered at least one therapeutic drug that prevents, inhibits and/or treats the bone metastasis, relapse or recurrence.

As used herein, an "agent for avoiding or preventing bone degradation" refers to any molecule capable of treating or stopping bone degradation either by stimulating the osteoblast proliferation or inhibiting the osteoclast proliferation. Illustrative examples of agents used for avoiding and/or preventing bone degradation include, although not limited to:

Parathyroid hormone (PTH) and Parathyroid like hormone (PTHLH) inhibitors (including blocking antibodies) or recombinant forms thereof (teriparatide corresponding to the amino acids 7-34 of PTH). This hormone acts by stimulating the osteoclasts and increasing their activity.

Strontium ranelate: is an alternative oral treatment, and forms part of the group of drugs called "dual action bone agents" (DABAs) because they stimulate the osteoblast proliferation and inhibit the osteoclast proliferation.

"Estrogen receptor modulators" (SERM) refers to compounds which interfere or inhibit the binding of estrogens to the receptor, regardless of the mechanism. Examples of estrogen receptor modulators include, among others, estrogens progestagen, estradiol, droloxifene, raloxifene, lasofoxifene, TSE-424, tamoxifen, idoxifene, L Y353381, LY117081, toremifene, fluvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate 4,4'dihydroxybenzophenone-2,4-dinitrophenyl-hydrazone and SH646.

Calcitonin: directly inhibits the osteoclast activity through the calcitonin receptor. The calcitonin receptors have been identified on the surface of the osteoclasts.

Bisphosphonates: are a group of medicinal products used for the prevention and the treatment of diseases with bone resorption and reabsorption such as osteoporosis and cancer with bone metastasis, the latter being with or without hypercalcaemia, associated to breast cancer and prostate cancer. Examples of bisphosphonates which can be used in the therapy designed by means of the fifth method of the invention include, although not limited to, nitrogenous bisphosphonates (such as pamidronate, neridronate, olpadronate, alendronate, ibandronate, risedronate, incadronate, zoledronate or zoledronic acid, etc.) and non-nitrogenous bisphosphonates (such as etidronate, clodronate, tiludronate, etc.).

"Cathepsin K inhibitors" refers to compounds which interfere in the cathepsin K cysteine protease activity. Non-limiting examples of cathepsin K inhibitors include 4-amino-pyrimidine-2-carbonitrile derivatives (described in the International patent application WO 03/020278 under the name of Novartis Pharma GMBH), pyrrolo-pyrimidines described in the publication WO 03/020721 (Novartis Pharma GMBH) and the publication WO 04/000843 (ASTRAZENECA AB) as well as the inhibitors described in the publications PCT WO 00/55126 of Axys Pharmaceuticals, WO 01/49288 of Merck Frosst Canada & Co. and Axys Pharmaceuticals.

"DKK-1(Dickkopf-1) inhibitor" as used herein refers to any compound which is capable of reducing DKK-1 activity. DKK-1 is a soluble Wnt pathway antagonist expressed predominantly in adult bone and upregulated in myeloma patients with osteolytic lesions. Agents targeting DKK-1 may play a role in preventing osteolytic bone disease in multiple myeloma patients. BHQ880 from Novartis is a first-in-class, fully human, anti-DKK-1 neutralizing antibody. Preclinical studies support the hypothesis that BHQ880 promotes bone formation and thereby inhibits tumor-induced osteolytic disease (Ettenberg S. et al., American Association for Cancer Research Annual Meeting. Apr. 12-16, 2008; San Diego, Calif. Abstract).

"Dual MET and VEGFR2 inhibitor" as used herein refers to any compound which is a potent dual inhibitor of the MET and VEGF pathways designed to block MET driven tumor escape. MET is expressed not only in tumor cells and endothelial cells, but also in osteoblasts (bone-forming cells) and osteoclasts (bone-removing cells). HGF binds to MET on all of these cell types, giving the MET pathway an important role in multiple autocrine and paracrine loops. Activation of MET in tumor cells appears to be important in the establishment of metastatic bone lesions. At the same time, activation of the MET pathway in osteoblasts and osteoclasts may lead to pathological features of bone metastases, including abnormal bone growth (ie, blastic lesions) or destruction (ie, lytic lesion). Thus, targeting the MET pathway may be a viable strategy in preventing the establishment and progression of metastatic bone lesions. Cabozantinib (Exelixis, Inc), formerly known as XL184 (CAS 849217-68-1), is a potent dual inhibitor of the MET and VEGF pathways designed to block MET driven tumor escape. In multiple preclinical studies cabozantinib has been shown to kill tumor cells, reduce metastases, and inhibit angiogenesis (the formation of new blood vessels necessary to support tumor growth). Another suitable dual inhibitors are E7050 (N-[2-Fluoro-4-({2-[4-(4-methylpiperazin-1-yl) piperidin-1-yl] carbonylaminopyridin-4-yl} oxy) phenyl]-N'-(4-fluorophenyl) cyclopropane-1,1-dicarboxamide (2R,3R)-tartrate) (CAS 928037-13-2) or Foretinib (also known as GSK1363089, XL880, CAS 849217-64-7).

"RANKL inhibitors" as used herein refer to any compound which is capable of reducing the RANK activity. RANKL is found on the surface of the osteoblast membrane of the stroma and T-lymphocyte cells, and these T-lymphocyte cells are the only ones which have demonstrated the capacity for secreting it. Its main function is the activation of the osteoclasts, cells involved in the bone resorption. The RANKL inhibitors can act by blocking the binding of RANKL to its receptor (RANK), blocking the RANK-mediated signaling or reducing the expression of RANKL by blocking the transcription or the translation of RANKL. RANKL antagonists or inhibitors suitable for use in the present invention include, without limitation:

a suitable RANK protein which is capable of binding RANKL and which comprises the entire or a fragment of the extracellular domain of a RANK protein. The soluble RANK may comprise the signal peptide and the extracellular domain of the murine or human RANK polypeptides, or alternatively, the mature form of the protein with the signal peptide removed can be used.

Osteoprotegerin or a variant thereof with RANKL-binding capacity.

RANKL-specific antisense molecules

Ribozymes capable of processing the transcribed products of RANKL

Specific anti-RANKL antibodies. "Anti-RANKL antibody or antibody directed against RANKL" is understood herein as all that antibody which is capable of binding specifically to the ligand of the activating receptor for the nuclear factor KB (RANKL) inhibiting one or more RANKL functions. The antibodies can be prepared using any of the methods which are known by the person skilled in the art. Thus, the polyclonal antibodies are prepared by means of immunizing an animal with the protein to be inhibited. The monoclonal antibodies are prepared using the method described by Kohler, Milstein et al. (Nature, 1975, 256: 495). Antibodies suitable in the context of the present invention include intact antibodies which comprise a variable antigen binding region and a constant region, fragments "Fab", "F(ab')2" and "Fab", Fv, scFv, diabodies and bispecific antibodies.

Specific anti-RANKL nanobodies. Nanobodies are antibody-derived therapeutic proteins that contain the unique structural and functional properties of naturally-occurring heavy-chain antibodies. The Nanobody technology was originally developed following the discovery that camelidae (camels and llamas) possess fully functional antibodies that lack light chains. The general structure of nanobodies is FR1-CDR1-FR2-CDR2-FR3-CDR3-FR4 wherein FR1 to FR4 are the framework regions 1 to 4 CDR1 to CDR3 are the complementarity determining regions 1 to 3. These heavy-chain antibodies contain a single variable domain (VHH) and two constant domains (CH2 and CH3). Importantly, the cloned and isolated VHH domain is a perfectly stable polypeptide harbouring the full antigen-binding capacity of the original heavy-chain antibody. These newly discovered VHH domains with their unique structural and functional properties form the basis of a new generation of therapeutic antibodies which Ablynx has named Nanobodies.

In one embodiment, the RANKL inhibitor is selected from the group consisting of a RANKL specific antibody, a RANKL specific nanobody and osteoprotegerin. In a specific embodiment, the anti-RANKL antibody is a monoclonal antibody. In a yet more specific embodiment, the anti-RANKL antibody is Denosumab (Pageau, Steven C. (2009). mAbs 1 (3): 210-215, CAS number 615258-40-7) (the entire contents of which are hereby incorporated by reference). Denosumab is a fully human monoclonal antibody which binds to RANKL and prevents its activation (it does not bind to the RANK receptor). Various aspects of Denosumab are covered by U.S. Pat. Nos. 6,740,522; 7,411,050; 7,097,834; 7,364,736 (the entire contents of each of which are hereby incorporated by reference in their entirety). In another embodiment, the RANKL inhibitor an antibody, antibody fragment, or fusion construct that binds the same epitope as Denosumab.

In a preferred embodiment, the anti-RANKL nanobody is any of the nanobodies as described in WO2008142164, (the contents of which are incorporated in the present application by reference). In a still more preferred embodiment, the anti-RANKL antibody is the ALX-0141 (Ablynx). ALX-0141 has been designed to inhibit bone loss associated with post-menopausal osteoporosis, rheumatoid arthritis, cancer and certain medications, and to restore the balance of healthy bone metabolism.

In a preferred embodiment, the agent preventing the bone degradation is selected from the group consisting of a bisphosphonate, a RANKL inhibitor, PTH and PTHLH inhibitor or a PRG analog, strontium ranelate, a DKK-1 inhibitor, a dual MET and VEGFR2 inhibitor, an estrogen receptor modulator, Radium-223, calcitonin, and a cathepsin K inhibitor. In a more preferred embodiment the agent preventing the bone degradation is a bisphosphonate. In a yet more preferred embodiment, the bisphosphonate is the zoledronic acid.

In one embodiment, a CCR5 antagonist is administered to prevent or inhibit metastasis of the primary prostate cancer tumor to bone or relapse or recurrence. In one embodiment, the CCR5 antagonist is a large molecule. In another embodiment, the CCR5 antagonist is a small molecule. In some embodiments, the CCR5 antagonist is Maraviroc. In some embodiments, the CCR5 antagonist is Vicriviroc. In some aspects, the CCR5 antagonist is Aplaviroc. In some aspects, the CCR5 antagonist is a spiropiperidine CCR5 antagonist. (Rotstein D. M. et al. 2009. Spiropiperidine CCR5 antagonists. Bioorganic & Medicinal Chemistry Letters. 19 (18): 5401-5406. In some embodiments, the CCR5 antagonist is INCB009471 (Kuritzkes, D. R. 2009. HIV-1 entry inhibitors: an overview. Curr. Opin. HIV AIDS. 4(2): 82-7).

In a preferred embodiment the dual MET and VEGFR2 inhibitor is selected from the group consisting of Cabozantinib, Foretinib and E7050.

In another aspect, the treatment is an mTor inhibitor. In some aspects, the mTor inhibitor is a dual mTor/PI3kinase inhibitor. In some aspects, the mTor inhibitor is used to prevent or inhibit metastasis, relapse or recurrence. In some aspects the mTor inhibitor is selected from the group consisting of: ABI009 (sirolimus), rapamycin (sirolimus), Abraxane (paclitaxel), Absorb (everolimus), Afinitor (everolimus), Afinitor with Gleevec, AS703026 (pimasertib), Axxess (umirolimus), AZD2014, BEZ235, Biofreedom (umirolimus), BioMatrix (umirolimus), BioMatrix flex (umirolimus), CC115, CC223, Combo Bio-engineered Sirolimus Eluting Stent ORBUSNEICH (sirolimus), Curaxin CBLC102 (mepacrine), DE109 (sirolimus), DS3078, Endeavor DES (zotarolimus), Endeavor Resolute (zotarolimus), Femara (letrozole), Hocena (antroquinonol), INK128, Inspiron (sirolimus), IPI504 (retaspimycin hydrochloride), KRN951 (tivozanib), ME344, MGA031 (teplizumab), MiStent SES (sirolimus), MKC1, Nobori (umirolimus), OSI027, OVI123 (cordycepin), Palomid 529, PF04691502, Promus Element (everolimus), PWT33597, Rapamune (sirolimus), Resolute DES (zotarolimus), RG7422, SAR245409, SF1126, SGN75 (vorsetuzumab mafodotin), Synergy (everolimus), Taltorvic (ridaforolimus), Tarceva (erlotinib), Torisel (temsirolimus), Xience Prime (everolimus), Xience V (everolimus), Zomaxx (zotarolimus), Zortress (everolimus), Zotarolimus Eluting Peripheral Stent MEDTRONIC (zotarolimus), AP23841, AP24170, ARmTOR26, BN107, BN108, Canstatin GENZYME (canstatin), CU906, EC0371, EC0565, KI1004, LOR220, NV128, Rapamycin ONCOIMMUNE (sirolimus), SB2602, Sirolimus PNP SAMYANG BIOPHARMACEUTICALS (sirolimus), TOP216, VLI27, VS5584, WYE125132, XL388, Advacan (everolimus), AZD8055, Cypher Select Plus Sirolimus eluting Coronary Stent (sirolimus), Cypher Sirolimus eluting coronary stent (sirolimus), Drug Coated Balloon (sirolimus), E-Magic Plus (sirolimus), Emtor (sirolimus), Esprit (everolimus), Evertor (everolimus), HBF0079, LCP-Siro (sirolimus), Limus CLARIS (sirolimus), mTOR Inhibitor CELLZOME, Nevo Sirolimus eluting Coronary Stent (sirolimus), nPT-mTOR, Rapacan (sirolimus), Renacept (sirolimus), ReZolve (sirolimus), Rocas (sirolimus), SF1126, Sirolim (sirolimus), Sirolimus NORTH CHINA (sirolimus), Sirolimus RANBAXY (sirolimus), Sirolimus WATSON (sirolimus) Siropan (sirolimus), Sirova (sirolimus), Supralimus (sirolimus), Supralimus-Core (sirolimus), Tacrolimus WATSON (tacrolimus), TAFA93, Temsirolimus ACCORD (temsirolimus), Temsirolimus SANDOZ (temsirolimus), TOP216, Xience Prime (everolimus), Xience V (everolimus). In a specific aspect the mTor inhibitor is Afinitor (everolimus) (http://www.afinitor.com/index.jsp?usertrack.filter_applied=true&NovaId=4029462064338207963; last accessed Nov. 28, 2012). In another aspect, mTor inhibitors can be identified through methods known in the art. (See, e.g., Zhou, H. et al. Updates of mTor inhibitors. 2010. Anticancer Agents Med. Chem. 10(7): 571-81, which is herein incorporated by reference). In some aspects, the mTor inhibitor is used to treat or prevent or inhibit metastasis in a patient with advanced prostate cancer. In some aspects, the mTor inhibitor is used in combination with a second treatment. In some aspects, the second treatment is any treatment described herein.

In another aspect, the treatment is a Src kinase inhibitor. In some aspects, the Src inhibitor is used to prevent or inhibit metastasis, relapse or recurrence. In some aspects, the Src kinase inhibitor is selected from the group: AZD0530 (saracatinib), Bosulif (bosutinib), ENMD981693, KD020, KX01, Sprycel (dasatinib), Yervoy (ipilimumab), AP23464, AP23485, AP23588, AZD0424, c-Src Kinase Inhibitor KISSEI, CU201, KX2361, SKS927, SRN004, SUNK706, TG100435, TG100948, AP23451, Dasatinib HETERO (dasatinib), Dasatinib VALEANT (dasatinib), Fontrax (dasatinib), Src Kinase Inhibitor KINEX, VX680,(tozasertib lactate), XL228, and SUNK706. In some embodiments, the Src kinase inhibitor is dasatinib. In another aspect, Src kinase inhibitors can be identified through methods known in the art (See, e.g., Sen, B. and Johnson, F. M. Regulation of Src Family Kinases in Human Cancers. 2011. *J. Signal Transduction.* 2011: 14 pages, which is herein incorporated by reference). In some aspects, the Src kinase inhibitor is used to treat or prevent or inhibit metastasis, relapse or recurrence in a patient that is positive for the SRC-responsive signature (SRS). In some aspects, the Src kinase inhibitor is used to treat or prevent or inhibit metastasis in a patient with advanced prostate cancer. In some aspects, the Src kinase inhibitor is used in combination with a second treatment. In some aspects, the second treatment is any treatment described herein.

In another aspect, the treatment is a COX-2 inhibitor. In some aspects, the COX-2 inhibitor is used to prevent or inhibit metastasis, relapse or recurrence. In some aspects, the COX-2 inhibitor is selected from the group: ABT963, Acetaminophen ER JOHNSON (acetaminophen), Acular X (ketorolac tromethamine), BAY1019036 (aspirin), BAY987111 (diphenhydramine, naproxen sodium), BAY11902 (piroxicam), BCIBUCH001 (ibuprofen), Capoxigem (apricoxib), CS502, CS670 (pelubiprofen), Diclofenac HPBCD (diclofenac), Diractin (ketoprofen), GW406381, HCT1026 (nitroflurbiprofen), Hyanalgese-D (diclofenac), HydrocoDex (acetaminophen, dextromethorphan, hydrocodone), Ibuprofen Sodium PFIZER (ibuprofen sodium), Ibuprofen with Acetaminophen PFIZER (acetaminophen, ibuprofen), Impracor (ketoprofen), IP880 (diclofenac), IP940 (indomethacin), ISV205 (diclofenac sodium), JNS013 (acetaminophen, tramadol hydrochloride), Ketoprofen TDS (ketoprofen), LTNS001 (naproxen etemesil), Mesalamine SALIX (mesalamine), Mesalamine SOFAR (mesalamine), Mesalazine (mesalamine), ML3000 (licofelone), MRX7EAT (etodolac), Naproxen IROKO (naproxen), NCX4016 (nitroaspirin), NCX701 (nitroacetaminophen), Nuprin SCOLR (ibuprofen), OMS103HP (amitriptyline hydrochloride, ketoprofen, oxymetazoline hydrochloride), Oralease (diclofenac), OxycoDex (dextromethorphan, oxycodone), P54, PercoDex (acetaminophen, dextromethorphan, oxycodone), PL3100 (naproxen, phosphatidyl choline), PSD508, R-Ketoprofen (ketoprofen), Remura (bromfenac sodium), ROX828 (ketorolac tromethamine), RP19583 (ketoprofen lysine), RQ00317076, SDX101 (R-etodolac), TDS943 (diclofenac sodium), TDT070 (ketoprofen), TPR100, TQ1011 (ketoprofen), TT063 (S-flurbiprofen), UR8880 (cimicoxib), V0498TA01A (ibuprofen), VT122 (etodolac, propranolol), XP20B (acetaminophen, dextropropoxyphene), XP21B (diclofenac potassium), XP21L (diclofenac potassium), Zoenasa (acetylcysteine, mesalamine), Acephen, Actifed Plus, Actifed-P, Acular, Acular LS, Acular PF, Acular X, Acuvail, Advil, Advil Allergy Sinus, Advil Cold and Sinus, Advil Congestion Relief, Advil PM, Advil PM Capsule, Air Salonpas, Airtal, Alcohol-Free NyQuil Cold & Flu Relief, Aleve, Aleve ABDI IBRAHIM, Aleve-D, Alka-Seltzer, Alka-Seltzer BAYER, Alka-Seltzer Extra Strength, Alka-Seltzer Lemon-Lime, Alka-Seltzer Original, Alka-Seltzer Plus, Alka-Seltzer plus Cold and Cough, Alka-Seltzer plus Cold and Cough Formula, Alka-Seltzer Plus Day and Night Cold Formula, Alka-Seltzer Plus Day Non-Drowsy Cold Formula, Alka- Seltzer Plus Flu Formula, Alka-Seltzer Plus Night Cold Formula, Alka-Seltzer Plus Sinus Formula, Alka-Seltzer Plus Sparkling Original Cold Formula, Alka-Seltzer PM, Alka-Seltzer Wake-Up Call, Anacin, Anaprox, Anaprox MINERVA, Ansaid, Apitoxin, Apranax, Apranax abdi, Arcoxia, Arthritis Formula Bengay, Arthrotec, Asacol, Asacol HD, Asacol MEDUNA ARZNEIMITTEL, Asacol ORIFARM, Aspirin BAYER, Aspirin Complex, Aspirin Migraine, AZD3582, Azulfidine, Baralgan M, BAY1019036, BAY987111, BAY11902, BCIBUCH001, Benadryl Allergy, Benadryl Day and Night, Benylin 4 Flu, Benylin Cold and Flu, Benylin Cold and Flu Day and Night, Benylin Cold and Sinus Day and Night, Benylin Cold and Sinus Plus, Benylin Day and Night Cold and Flu Relief, Benylin1 All-In-One, Brexin, Brexin ANGELINI, Bromday, Bufferin, Buscopan Plus, Caldolor, Calmatel, Cambia, Canasa, Capoxigem, Cataflam, Celebrex, Celebrex ORIFARM, Children's Advil Allergy Sinus, Children's Tylenol, Children's Tylenol Cough and Runny Nose, Children's Tylenol plus cold, Children's Tylenol plus Cold and Cough, Children's Tylenol plus cold and stuffy nose, Children's Tylenol plus Flu, Children's Tylenol plus cold & allergy, Children's Tylenol plus Cough & Runny Nose, Children's Tylenol plus Cough & Sore Throat, Children's Tylenol plus multi symptom cold, Clinoril, Codral Cold and Flu, Codral Day and Night Day Tablets, Codral Day and Night Night Tablets, Codral Nighttime, Colazal, Combunox, Contac Cold plus Flu, Contac Cold plus Flu Non-Drowsy, Coricidin D, Coricidin HBP Cold and Flu, Coricidin HBP Day and Night Multi-Symptom Cold, Coricidin HBP Maximum Strength Flu, Coricidin HBP Nighttime Multi-Symptom Cold, Coricidin II Extra Strength Cold and Flu, CS502, CS670, Daypro, Daypro Alta, DDS06C, Demazin Cold and Flu, Demazin Cough, Cold and Flu, Demazin day/night Cold and Flu, Demazin PE Cold and Flu, Demazin PE day/night Cold and Flu, Diclofenac HPBCD, Dimetapp Day Relief, Dimetapp Multi-Symptom Cold and Flu, Dimetapp Night Relief, Dimetapp Pain and Fever Relief, Dimetapp PE Sinus Pain, Dimetapp PE Sinus Pain plus Allergy, Dipentum, Diractin, Disprin Cold 'n' Fever, Disprin Extra, Disprin Forte. Disprin Plus, Dristan Cold, Dristan Junior, Drixoral Plus, Duexis, Dynastat, Efferalgan, Efferalgan Plus Vitamin C, Efferalgan Vitamin C, Elixsure IB, Excedrin Back and Body, Excedrin Migraine, Excedrin PM, Excedrin Sinus Headache, Excedrin Tension Headache, Falcol, Fansamac, Feldene, FeverAll, Fiorinal, Fiorinal with Codeine, Flanax, Flector Patch, Flucam, Fortagesic, Gerbin, Giazo, Gladio, Goody's Back and Body Pain, Goody's Cool Orange, Goody's Extra Strength, Goody's PM, Greaseless Bengay, GW406381, HCT1026, He Xing Yi, Hyanalgese-D, HydrocoDex, Ibuprofen Sodium PFIZER, Ibuprofen with, Acetaminophen PFIZER, Icy Hot SANOFI AVENTIS, Impracor, Indocin, Indomethacin APP PHARMA, Indomethacin MYLAN, Infants' Tylenol, IP880, IP940, Iremod, ISV205, JNS013, Jr. Tylenol, Junifen, Junior Strength Advil, Junior Strength Motrin, Ketoprofen TDS, Lemsip Max, Lemsip Max All in One, Lemsip Max All Night, Lemsip Max Cold and Flu, Lialda, Listerine Mouth Wash, Lloyds Cream, Lodine, Lorfit P, Loxonin, LTNS001, Mersyndol, Mesalamine SALIX, Mesalamine SOFAR, Mesalazine, Mesasal GLAXO, Mesasal SANOFI, Mesulid, Metsal Heat Rub, Midol Complete, Midol Extended Relief, Midol Liquid Gels, Midol PM, Midol Teen Formula, Migranin COATED TABLETS, ML3000, Mobic, Mohrus, Motrin, Motrin Cold and Sinus Pain, Motrin PM, Movalis ASPEN, MRX7EAT, Nalfon, Nalfon PEDINOL, Naprelan, Naprosyn, Naprosyn RPG LIFE SCIENCE, Naproxen IROKO, NCX4016, NCX701, NeoProfen LUNDBECK, Nevanac, Nexcede, Niflan, Norgesic MEDICIS, Novalgin, Nuprin SCOLR, Nurofen, Nurofen Cold and Flu, Nurofen Max Strength Migraine, Nurofen Plus, Nuromol, NyQuil with Vitamin C, Ocufen, OMS103HP, Oralease, Orudis ABBOTT JAPAN, Oruvail, Osteluc, OxycoDex, P54, Panadol, Panadol Actifast, Paradine, Paramax, Parfenac, Pedea, Pennsaid, Pentasa, Pentasa ORIFARM, Peon, Percodan, Percodan-Demi, PercoDex, Percogesic, Perfalgan, PL2200, PL3100, Ponstel, Prexige, Prolensa, PSD508, R-Ketoprofen, Rantudil, Relafen, Remura, Robaxisal, Rotec, Rowasa, ROX828, RP19583, RQ00317076, Rubor, Salofalk, Salonpas, Saridon, SDX101, Seltouch, sfRowasa, Shinbaro, Sinumax, Sinutab, Sinutab, sinus, Spalt, Sprix, Strefen, Sudafed Cold and Cough, Sudafed Head Cold and Sinus, Sudafed PE Cold plus Cough, Sudafed PE Pressure plus Pain, Sudafed PE, Severe Cold, Sudafed PE Sinus Day plus Night Relief Day Tablets, Sudafed PE Sinus Day plus Night Relief Night Tablets, Sudafed PE Sinus plus Anti-inflammatory Pain Relief, Sudafed Sinus Advance, Surgam, Synalgos-DC, Synflex, Tavist allergy/sinus/headache, TDS943, TDT070, Theraflu Cold and Sore Throat, Theraflu Daytime Severe Cold and Cough, Theraflu Daytime Warming Relief, Theraflu Warming Relief Caplets Daytime Multi-Symptom Cold, Theraflu Warming Relief Cold and Chest Congestion, Thomapyrin, Thomapyrin C, Thomapyrin Effervescent, Thomapyrin Medium, Tilcotil, Tispol, Tolectin, Toradol, TPR100, TQ1011, Trauma-Salbe, Trauma-Salbe Kwizda, Treo, Treximet, Trovex, TT063, Tylenol, Tylenol Allergy Multi-Symptom, Tylenol Back Pain, Tylenol Cold & Cough Daytime, Tylenol Cold & Cough Nighttime, Tylenol Cold and Sinus Daytime, Tylenol Cold and Sinus Nighttime, Tylenol Cold Head Congestion Severe, Tylenol Cold Multi Symptom Daytime, Tylenol Cold Multi Symptom Nighttime Liquid, Tylenol Cold Multi Symptom Severe, Tylenol Cold Non-Drowsiness Formula, Tylenol Cold Severe Congestion Daytime, Tylenol Complete Cold, Cough and Flu Night time, Tylenol Flu Nighttime, Tylenol Menstrual, Tylenol PM, Tylenol Sinus Congestion & Pain Daytime, Tylenol Sinus Congestion & Pain Nighttime, Tylenol Sinus Congestion & Pain Severe, Tylenol Sinus Severe Congestion Daytime, Tylenol Ultra Relief, Tylenol with Caffeine and Codeine phosphate, Tylenol with Codeine phosphate, Ultra Strength Bengay Cream, Ultracet, UR8880, V0498TA01A, Vicks NyQuil Cold and Flu Relief, Vicoprofen, Vimovo, Voltaren Emulgel, Voltaren GEL, Voltaren NOVARTIS CONSUMER HEALTH GMBH, Voltaren XR, VT122, Xefo, Xefo Rapid, Xefocam, Xibrom, XL3, Xodol, XP20B, XP21B, XP21L, Zipsor, and Zoenasa. In another aspect, COX-2 inhibitors can be identified through methods known in the art (See, e.g., Dannhardt, G. and Kiefer, W. Cyclooxygenase inhibitors—current status and future prospects. 2001. *Eur. J. Med. Chem.* 36: 109-126, which is herein incorporated by reference). In some aspects, the COX-2 inhibitor is used to treat or prevent or inhibit metastasis in a patient with advanced prostate cancer. In some aspects, the COX-2 inhibitor is used in combination with a second treatment. In some aspects, the second treatment is any treatment described herein. In some aspects, the COX-2 inhibitor is used in combination with a second treatment selected from the group consisting of: Denosumab, Zometa (http://www.us.zometa.com/index.jsp?usertrack.filter_applied=true&NovaId=2935376934467633633; last accessed Dec. 2, 2012), Carbozantinib or Cabozantinib, Antibody or peptide blocking PTHLH (parathyroid hormone like hormone) or PTHrP (parathyroid hormone related protein).

In one embodiment, the treatment is Radium 223. In a preferred embodiment the Radium 223 therapy is Alpharadin (aka, Xofigo) (radium-223 dichloride). Alpharadin uses alpha radiation from radium-223 decay to kill cancer cells. Radium-223 naturally self-targets to bone metastases by virtue of its properties as a calcium-mimic. Alpha radiation has a very short range of 2-10 cells (when compared to current radiation therapy which is based on beta or gamma radiation), and therefore causes less damage to surrounding healthy tissues (particularly bone marrow). With similar properties to calcium, radium-223 is drawn to places where calcium is used to build bone in the body, including the site of faster, abnormal bone growth—such as that seen in the skeletal metastases of men with advanced, castration-resistant prostate cancer. Radium-223, after injection, is carried in the bloodstream to sites of abnormal bone growth. The place where a cancer starts in the body is known as the primary tumor. Some of these cells may break away and be carried in the bloodstream to another part of the body. The cancer cells may then settle in that part of the body and form a new tumor. If this happens it is called a secondary cancer or a metastasis. Most patients with late stage prostate cancer suffer the maximum burden of disease in their bones. The aim with radium-223 is to selectively target this secondary cancer. Any radium-223 not taken-up in the bones is quickly routed to the gut and excreted.

Alternatively a combined treatment can be carried out in which more than one agent from those mentioned above are combined to treat and/or prevent the metastasis, relapse or recurrence or said agents can be combined with other supplements, such as calcium or vitamin D or with a hormone treatment.

When the cancer has metastasized, systemic treatments including but not limited to chemotherapy, hormone treatment, immunotherapy, or a combination thereof are used. Additionally, radiotherapy and/or surgery can be used. The choice of treatment generally depends on the type of primary cancer, the size, the location of the metastasis, the age, the general health of the patient and the types of treatments used previously.

The systemic treatments are those that reach the entire body:
  Chemotherapy is the use of medicaments to destroy cancer cells. The medicaments are generally administered through oral or intravenous route. Sometimes, chemotherapy is used together with radiation treatment.
  Hormone therapy is based on the fact that some hormones promote cancer growth. For example, estrogen in women produced by the ovaries sometimes promotes the breast cancer growth. There are several ways for stopping the production of these hormones. A way is to remove the organs producing them: the ovaries in the case of women, the testicles in the case of the men. More frequently, medicaments to prevent these organs from producing the hormones or to prevent the hormones from acting on the cancer cells can be used.
  Immunotherapy is a treatment that aids the immune system itself of the patient to combat cancer. There are several types of immunotherapy which are used to treat metastasis patients. These include but are not limited to cytokines, monoclonal antibodies and antitumor vaccines.

Method for Designing Customized Therapy of the Invention in Prostate Cancer Patients with Bone Metastasis, Relapse or Recurrence Patients suffering prostate cancer which has already metastasized to the bone and in which there are elevated c-MAF levels may particularly benefit from therapies aimed at preventing the bone degradation caused by the increased osteoclastic activity.

Thus, in another aspect, the invention relates to an in vitro method for designing a customized therapy for a subject with prostate cancer with bone metastasis, relapse or recurrence which comprises
(i) quantifying the c-MAF gene expression level in a metastatic tumor sample from bone of said subject, and
(ii) comparing the expression level previously obtained with the expression level of said gene in a control sample,
wherein if the expression levels are increased with respect to the expression levels of said gene in the control sample, then said subject is susceptible to receive a therapy aiming to prevent the bone degradation.
wherein if the expression level is not increased with respect to said reference value, then said subject is not susceptible to receive a therapy aiming to prevent and/or treat the bone metastasis.

The terms and expressions "subject", "prostate cancer", "tumor sample", "metastasis", "determination of expression levels", "c-MAF gene", "increased expression levels", "relapse" "recurrence" and "control sample" have been described in detail in relation to the first method of the invention and are equally applicable to the second and third method of the invention.

In a preferred embodiment, the bone metastasis is osteolytic metastasis.

The third method of the invention comprises in a first step, quantifying the c-MAF gene expression level in a tumor sample in a subject suffering prostate cancer. In the case of the third method of the invention, in some embodiments, the sample is a tissue sample from bone metastasis.

In a preferred embodiment, the third method of the invention comprises quantifying only the c-MAF gene expression level as a single marker, i.e., the method does not involve determining the expression level of any additional marker.

In a second step the c-MAF gene expression level obtained in the tumor sample of the subject is compared with the expression level of said gene in a control sample. The determination of the c-MAF gene expression levels must be correlated to values of a control sample or reference sample. Depending on the type of tumor to be analyzed, the exact nature of the control sample may vary. Thus, in the case involving the third method of the invention, then the reference sample is a tumor tissue sample of subject with prostate cancer who has not suffered metastasis or that correspond to the median value of the c-MAF gene expression level measured in a tumor tissue collection in biopsy samples of subjects with prostate cancer who has not suffered metastasis.

Once the c-MAF gene expression level in the sample is measured and compared with the control sample, if the expression level of said gene are increased with respect to its expression level in the control sample, then it can be concluded that said subject is susceptible to receive a therapy aiming to avoid or prevent bone degradation.

In certain embodiments, if a high risk of reoccurrence is predicted based on the c-MAF expression level, the subject is susceptible to radical prostatectomy and radiation treatment. In other embodiments, if a low risk of reoccurrence is predicted based on the c-MAF level, the subject may be offered radical prostatectomy but not radiation treatment (adjuvant radiotherapy).

As used herein, an "agent for avoiding or preventing bone degradation" refers to any molecule capable of treating or stopping bone degradation either by stimulating the osteoblast proliferation or inhibiting the osteoclast proliferation. Illustrative examples of agents used for avoiding and/or preventing bone degradation include, although not limited to:

Parathyroid hormone (PTH) and Parathyroid like hormone (PTHLH) inhibitors (including blocking antibodies) or recombinant forms thereof (teriparatide corresponding to the amino acids 7-34 of PTH). This hormone acts by stimulating the osteoclasts and increasing their activity.

Strontium ranelate: is an alternative oral treatment, and forms part of the group of drugs called "dual action bone agents" (DABAs) because they stimulate the osteoblast proliferation and inhibit the osteoclast proliferation.

"Estrogen receptor modulators" (SERM) refers to compounds which interfere or inhibit the binding of estrogens to the receptor, regardless of the mechanism. Examples of estrogen receptor modulators include, among others, estrogens progestagen, estradiol, droloxifene, raloxifene, lasofoxifene, TSE-424, tamoxifen, idoxifene, L Y353381, LY117081, toremifene, fluvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate 4,4'dihydroxybenzophenone-2,4-dinitrophenyl-hydrazone and SH646.

Calcitonin: directly inhibits the osteoclast activity through the calcitonin receptor. The calcitonin receptors have been identified on the surface of the osteoclasts.

Bisphosphonates: are a group of medicinal products used for the prevention and the treatment of diseases with bone resorption and reabsorption such as osteoporosis and cancer with bone metastasis, the latter being with or without hypercalcaemia, associated to breast cancer and prostate cancer. Examples of bisphosphonates which can be used in the therapy designed by means of the fifth method of the invention include, although not limited to, nitrogenous bisphosphonates (such as pamidronate, neridronate, olpadronate, alendronate, ibandronate, risedronate, incadronate, zoledronate or zoledronic acid, etc.) and non-nitrogenous bisphosphonates (such as etidronate, clodronate, tiludronate, etc.).

"Cathepsin K inhibitors" refers to compounds which interfere in the cathepsin K cysteine protease activity. Non-limiting examples of cathepsin K inhibitors include 4-amino-pyrimidine-2-carbonitrile derivatives (described in the International patent application WO 03/020278 under the name of Novartis Pharma GMBH), pyrrolo-pyrimidines described in the publication WO 03/020721 (Novartis Pharma GMBH) and the publication WO 04/000843 (ASTRAZENECA AB) as well as the inhibitors described in the publications PCT WO 00/55126 of Axys Pharmaceuticals, WO 01/49288 of Merck Frosst Canada & Co. and Axys Pharmaceuticals. "DKK-1(Dickkopf-1) inhibitor" as used herein refers to any compound which is capable of reducing DKK-1 activity. DKK-1 is a soluble Wnt pathway antagonist expressed predominantly in adult bone and upregulated in myeloma patients with osteolytic lesions. Agents targeting DKK-1 may play a role in preventing osteolytic bone disease in multiple myeloma patients. BHQ880 from Novartis is a first-in-class, fully human, anti-DKK-1 neutralizing antibody. Preclinical studies support the hypothesis that BHQ880 promotes bone formation and thereby inhibits tumor-induced osteolytic disease (Ettenberg S. et al., American Association for Cancer Research Annual Meeting. Apr. 12-16, 2008; San Diego, Calif. Abstract).

"Dual MET and VEGFR2 inhibitor" as used herein refers to any compound which is a potent dual inhibitor of the MET and VEGF pathways designed to block MET driven tumor escape. MET is expressed not only in tumor cells and endothelial cells, but also in osteoblasts (bone-forming cells) and osteoclasts (bone-removing cells). HGF binds to MET on all of these cell types, giving the MET pathway an important role in multiple autocrine and paracrine loops. Activation of MET in tumor cells appears to be important in the establishment of metastatic bone lesions. At the same time, activation of the MET pathway in osteoblasts and osteoclasts may lead to pathological features of bone metastases, including abnormal bone growth (ie, blastic lesions) or destruction (ie, lytic lesion. Thus, targeting the MET pathway may be a viable strategy in preventing the establishment and progression of metastatic bone lesions. Cabozantinib (Exelixis, Inc), formerly known as XL184 (CAS 849217-68-1), is a potent dual inhibitor of the MET and VEGF pathways designed to block MET driven tumor escape. In multiple preclinical studies cabozantinib has been shown to kill tumor cells, reduce metastases, and inhibit angiogenesis (the formation of new blood vessels necessary to support tumor growth). Another suitable dual inhibitors are E7050 (N-[2-Fluoro-4-({2-[4-(4-methylpiperazin-1-yl) piperidin-1-yl] carbonylaminopyridin-4-yl} oxy) phenyl]-N'-(4-fluorophenyl) cyclopropane-1,1-dicarboxamide (2R,3R)-tartrate) (CAS 928037-13-2) or Foretinib (also known as GSK1363089, XL880, CAS 849217-64-7).

"RANKL inhibitors" as used herein refer to any compound which is capable of reducing the RANK activity. RANKL is found on the surface of the osteoblast membrane of the stroma and T-lymphocyte cells, and these T-lymphocyte cells are the only ones which have demonstrated the capacity for secreting it. Its main function is the activation of the osteoclasts, cells involved in the bone resorption. The RANKL inhibitors can act by blocking the binding of RANKL to its receptor (RANK), blocking the RANK-mediated signaling or reducing the expression of RANKL by blocking the transcription or the translation of RANKL. RANKL antagonists or inhibitors suitable for use in the present invention include, without limitation:

a suitable RANK protein which is capable of binding RANKL and which comprises the entire or a fragment of the extracellular domain of a RANK protein. The soluble RANK may comprise the signal peptide and the extracellular domain of the murine or human RANK polypeptides, or alternatively, the mature form of the protein with the signal peptide removed can be used.

Osteoprotegerin or a variant thereof with RANKL-binding capacity.

RANKL-specific antisense molecules

Ribozymes capable of processing the transcribed products of RANKL

Specific anti-RANKL antibodies. "Anti-RANKL antibody or antibody directed against RANKL" is understood herein as all that antibody which is capable of binding specifically to the ligand of the activating receptor for the nuclear factor κB (RANKL) inhibiting one or more RANKL functions. The antibodies can be prepared using any of the methods which are known by the person skilled in the art. Thus, the polyclonal antibodies are prepared by means of immunizing an animal with the protein to be inhibited. The monoclonal antibodies are prepared using the method described by Kohler, Milstein et al. (Nature, 1975, 256: 495). Antibodies suitable in the context of the present invention include intact antibodies which comprise a variable antigen binding region and a constant region, fragments "Fab", "F(ab')2" and "Fab", Fv, scFv, diabodies and bispecific antibodies.

Specific anti-RANKL nanobodies. Nanobodies are antibody-derived therapeutic proteins that contain the unique structural and functional properties of naturally-occurring heavy-chain antibodies. The Nanobody technology was originally developed following the discovery that camelidae (camels and llamas) possess fully functional antibodies that lack light chains. The general structure of nanobodies is FR1-CDR1-FR2-CDR2-FR3-CDR3-FR4 wherein FR1 to FR4 are the framework regions 1 to 4 CDR1 to CDR3 are the complementarity determining regions 1 to 3. These heavy-chain antibodies contain a single variable domain (VHH) and two constant domains (CH2 and CH3). Importantly, the cloned and isolated VHH domain is a perfectly stable polypeptide harbouring the full antigen-binding capacity of the original heavy-chain antibody. These newly discovered VHH domains with their unique structural and functional properties form the basis of a new generation of therapeutic antibodies which Ablynx has named Nanobodies.

In one embodiment, the RANKL inhibitor is selected from the group consisting of a RANKL specific antibody, a RANKL specific nanobody and osteoprotegerin. In a specific embodiment, the anti-RANKL antibody is a monoclonal antibody. In a yet more specific embodiment, the anti-RANKL antibody is Denosumab (Pageau, Steven C. (2009). mAbs 1 (3): 210-215, CAS number 615258-40-7) (the entire contents of which are hereby incorporated by reference). Denosumab is a fully human monoclonal antibody which binds to RANKL and prevents its activation (it does not bind to the RANK receptor). Various aspects of Denosumab are covered by U.S. Pat. Nos. 6,740,522; 7,411,050; 7,097,834; 7,364,736 (the entire contents of each of which are hereby incorporated by reference in their entirety). In another embodiment, the RANKL inhibitor an antibody, antibody fragment, or fusion construct that binds the same epitope as Denosumab.

In a preferred embodiment, the anti-RANKL nanobody is any of the nanobodies as described in WO2008142164, (the contents of which are incorporated in the present application by reference). In a still more preferred embodiment, the anti-RANKL antibody is the ALX-0141 (Ablynx). ALX-0141 has been designed to inhibit bone loss associated with post-menopausal osteoporosis, reumatoid arthritis, cancer and certain medications, and to restore the balance of healthy bone metabolism.

In a preferred embodiment, the agent preventing the bone degradation is selected from the group consisting of a bisphosphonate, a RANKL inhibitor, PTH and PTHLH inhibitor or a PRG analog, strontium ranelate, a DKK-1 inhibitor, a dual MET and VEGFR2 inhibitor, an estrogen receptor modulator, Radium-223, calcitonin, and a cathepsin K inhibitor. In a more preferred embodiment the agent preventing the bone degradation is a bisphosphonate. In a yet more preferred embodiment, the bisphosphonate is the zoledronic acid.

In one embodiment, a CCR5 antagonist is administered to prevent or inhibit metastasis of the primary prostate cancer tumor to bone, relapse or recurrence. In one embodiment, the CCR5 antagonist is a large molecule. In another embodiment, the CCR5 antagonist is a small molecule. In some embodiments, the CCR5 antagonist is Maraviroc (Velasco-Veláquez, M. et al. 2012. CCR5 Antagonist Blocks Metastasis of Basal Breast Cancer Cells. Cancer Research. 72:3839-3850.). In some embodiments, the CCR5 antagonist is Vicriviroc. Velasco-Veláquez, M. et al. 2012. CCR5 Antagonist Blocks Metastasis of Basal Breast Cancer Cells. Cancer Research. 72:3839-3850.). In some aspects, the CCR5 antagonist is Aplaviroc (Demarest J. F. et al. 2005. Update on Aplaviroc: An HIV Entry Inhibitor Targeting CCR5. Retrovirology 2(Suppl. 1): S13). In some aspects, the CCR5 antagonist is a spiropiperidine CCR5 antagonist. (Rotstein D. M. et al. 2009. Spiropiperidine CCR5 antagonists. Bioorganic & Medicinal Chemistry Letters. 19 (18): 5401-5406. In some embodiments, the CCR5 antagonist is INCB009471 (Kuritzkes, D. R. 2009. HIV-1 entry inhibitors: an overview. Curr. Opin. HIV AIDS. 4(2): 82-7).

In a preferred embodiment the dual MET and VEGFR2 inhibitor is selected from the group consisting of Cabozantinib, Foretinib and E7050.

In another aspect, the treatment is an mTor inhibitor. In some aspects, the mTor inhibitor is a dual mTor/PI3kinase inhibitor. In some aspects, the mTor inhibitor is used to prevent or inhibit metastasis, relapse or recurrence. In some aspects the mTor inhibitor is selected from the group consisting of: ABI009 (sirolimus), rapamycin (sirolimus), Abraxane (paclitaxel), Absorb (everolimus), Afinitor (everolimus), Afinitor with Gleevec, AS703026 (pimasertib), Axxess (umirolimus), AZD2014, BEZ235, Biofreedom (umirolimus), BioMatrix (umirolimus), BioMatrix flex (umirolimus), CC115, CC223, Combo Bio-engineered Sirolimus Eluting Stent ORBUSNEICH (sirolimus), Curaxin CBLC102 (mepacrine), DE109 (sirolimus), DS3078, Endeavor DES (zotarolimus), Endeavor Resolute (zotarolimus), Femara (letrozole), Hocena (antroquinonol), INK128, Inspiron (sirolimus), IPI504 (retaspimycin hydrochloride), KRN951 (tivozanib), ME344, MGA031 (teplizumab), MiStent SES (sirolimus), MKC1, Nobori (umirolimus), OSI027, OVI123 (cordycepin), Palomid 529, PF04691502, Promus Element (everolimus), PWT33597, Rapamune (sirolimus), Resolute DES (zotarolimus), RG7422, SAR245409, SF1126, SGN75 (vorsetuzumab mafodotin), Synergy (everolimus), Taltorvic (ridaforolimus), Tarceva (erlotinib), Torisel (temsirolimus), Xience Prime (everolimus), Xience V (everolimus), Zomaxx (zotarolimus), Zortress (everolimus), Zotarolimus Eluting Peripheral Stent MEDTRONIC (zotarolimus), AP23841, AP24170, ARmTOR26, BN107, BN108, Canstatin GENZYME (canstatin), CU906, EC0371, EC0565, KI1004, LOR220, NV128, Rapamycin ONCOIMMUNE (sirolimus), SB2602, Sirolimus PNP SAMYANG BIOPHARMACEUTICALS (sirolimus), TOP216, VLI27, VS5584, WYE125132, XL388, Advacan (everolimus), AZD8055, Cypher Select Plus Sirolimus eluting Coronary Stent (sirolimus), Cypher Sirolimus eluting coronary stent (sirolimus), Drug Coated Balloon (sirolimus), E-Magic Plus (sirolimus), Emtor (sirolimus), Esprit (everolimus), Evertor (everolimus), HBF0079, LCP-Siro (sirolimus), Limus CLARIS (sirolimus), mTOR Inhibitor CELLZOME, Nevo Sirolimus eluting Coronary Stent (sirolimus), nPT-mTOR, Rapacan (sirolimus), Renacept (sirolimus), ReZolve (sirolimus), Rocas (sirolimus), SF1126, Sirolim (sirolimus), Sirolimus NORTH CHINA (sirolimus), Sirolimus RANBAXY (sirolimus), Sirolimus WATSON (sirolimus) Siropan (sirolimus), Sirova (sirolimus), Supralimus (sirolimus), Supralimus-Core (sirolimus), Tacrolimus WATSON (tacrolimus), TAFA93, Temsirolimus ACCORD (temsirolimus), Temsirolimus SANDOZ (temsirolimus), TOP216, Xience Prime (everolimus), Xience V (everolimus). In a specific aspect the mTor inhibitor is Afinitor (everolimus) (http://www.afinitor.com/index.jsp?usertrack.filter_applied=true&NovaId=4029462064338207963; last accessed Nov. 28, 2012). In another aspect, mTor inhibitors can be identified through methods known in the art. (See, e.g., Zhou, H. et al. Updates of mTor inhibitors. 2010. Anticancer Agents Med. Chem. 10(7): 571-81, which is herein incorporated by reference). In some aspects, the mTor inhibitor is used to treat or prevent or inhibit metastasis in a patient with advanced prostate cancer. In some aspects, the mTor inhibitor is used in combination with a second treatment. In some aspects, the second treatment is any treatment described herein.

In another aspect, the treatment is a Src kinase inhibitor. In some aspects, the Src inhibitor is used to prevent or inhibit metastasis, relapse or recurrence. In some aspects, the Src kinase inhibitor is selected from the group: AZD0530 (saracatinib), Bosulif (bosutinib), ENMD981693, KD020, KX01, Sprycel (dasatinib), Yervoy (ipilimumab), AP23464, AP23485, AP23588, AZD0424, c-Src Kinase Inhibitor KISSEI, CU201, KX2361, SKS927, SRN004, SUNK706, TG100435, TG100948, AP23451, Dasatinib HETERO (dasatinib), Dasatinib VALEANT (dasatinib), Fontrax (dasatinib), Src Kinase Inhibitor KINEX, VX680,(tozasertib lactate), XL228, and SUNK706. In some embodiments, the Src kinase inhibitor is dasatinib. In another aspect, Src kinase inhibitors can be identified through methods known in the art (See, e.g., Sen, B. and Johnson, F. M. Regulation of Src Family Kinases in Human Cancers. 2011. *J. Signal Transduction.* 2011: 14 pages, which is herein incorporated by reference). In some aspects, the Src kinase inhibitor is used to treat or prevent or inhibit metastasis, relapse or recurrence in a patient that is positive for the SRC-responsive signature (SRS). In some aspects, the Src kinase inhibitor is used to treat or prevent or inhibit metastasis in a patient with advanced prostate cancer. In some aspects, the Src kinase inhibitor is used in combination with a second treatment. In some aspects, the second treatment is any treatment described herein.

In another aspect, the treatment is a COX-2 inhibitor. In some aspects, the COX-2 inhibitor is used to prevent or inhibit metastasis, relapse or recurrence. In some aspects, the COX-2 inhibitor is selected from the group: ABT963, Acetaminophen ER JOHNSON (acetaminophen), Acular X (ketorolac tromethamine), BAY1019036 (aspirin), BAY987111 (diphenhydramine, naproxen sodium), BAY11902 (piroxicam), BCIBUCH001 (ibuprofen), Capoxigem (apricoxib), CS502, CS670 (pelubiprofen), Diclofenac HPBCD (diclofenac), Diractin (ketoprofen), GW406381, HCT1026 (nitroflurbiprofen), Hyanalgese-D (diclofenac), HydrocoDex (acetaminophen, dextromethorphan, hydrocodone), Ibuprofen Sodium PFIZER (ibuprofen sodium), Ibuprofen with Acetaminophen PFIZER (acetaminophen, ibuprofen), Impracor (ketoprofen), IP880 (diclofenac), IP940 (indomethacin), ISV205 (diclofenac sodium), JNS013 (acetaminophen, tramadol hydrochloride), Ketoprofen TDS (ketoprofen), LTNS001 (naproxen etemesil), Mesalamine SALIX (mesalamine), Mesalamine SOFAR (mesalamine), Mesalazine (mesalamine), ML3000 (licofelone), MRX7EAT (etodolac), Naproxen IROKO (naproxen), NCX4016 (nitroaspirin), NCX701 (nitroacetaminophen), Nuprin SCOLR (ibuprofen), OMS103HP (amitriptyline hydrochloride, ketoprofen, oxymetazoline hydrochloride), Oralease (diclofenac), OxycoDex (dextromethorphan, oxycodone), P54, PercoDex (acetaminophen, dextromethorphan, oxycodone), PL3100 (naproxen, phosphatidyl choline), PSD508, R-Ketoprofen (ketoprofen), Remura (bromfenac sodium), ROX828 (ketorolac tromethamine), RP19583 (ketoprofen lysine), RQ00317076, SDX101 (R-etodolac), TDS943 (diclofenac sodium), TDT070 (ketoprofen), TPR100, TQ1011 (ketoprofen), TT063 (S-flurbiprofen), UR8880 (cimicoxib), V0498TA01A (ibuprofen), VT122 (etodolac, propranolol), XP20B (acetaminophen, dextropropoxyphene), XP21B (diclofenac potassium), XP21L (diclofenac potassium), Zoenasa (acetylcysteine, mesalamine), Acephen, Actifed Plus, Actifed-P, Acular, Acular LS, Acular PF, Acular X, Acuvail, Advil, Advil Allergy Sinus, Advil Cold and Sinus, Advil Congestion Relief, Advil PM, Advil PM Capsule, Air Salonpas, Airtal, Alcohol-Free NyQuil Cold & Flu Relief, Aleve Aleve ABDI IBRAHIM, Aleve-D, Alka-Seltzer, Alka-Seltzer BAYER, Alka-Seltzer Extra Strength, Alka-Seltzer Lemon-Lime, Alka-Seltzer Original, Alka-Seltzer Plus, Alka-Seltzer plus Cold and Cough, Alka-Seltzer plus Cold and Cough Formula, Alka-Seltzer Plus Day and Night Cold Formula, Alka-Seltzer Plus Day Non-Drowsy Cold Formula, Alka-Seltzer Plus Flu Formula, Alka-Seltzer Plus Night Cold Formula, Alka-Seltzer Plus Sinus Formula, Alka-Seltzer Plus Sparkling Original Cold Formula, Alka-Seltzer PM, Alka-Seltzer Wake-Up Call, Anacin, Anaprox, Anaprox MINERVA, Ansaid, Apitoxin, Apranax, Apranax abdi, Arcoxia, Arthritis Formula Bengay, Arthrotec, Asacol, Asacol HD, Asacol MEDUNA ARZNEIMITTEL, Asacol ORIFARM, Aspirin BAYER, Aspirin Complex, Aspirin Migran, AZD3582, Azulfidine, Baralgan M, BAY1019036, BAY987111, BAY11902, BCIBUCH001, Benadryl Allergy, Benadryl Day and Night, Benylin 4 Flu, Benylin Cold and Flu, Benylin Cold and Flu Day and Night, Benylin Cold and Sinus Day and Night, Benylin Cold and Sinus Plus, Benylin Day and Night Cold and Flu Relief, Benylin1 All-In-One, Brexin, Brexin ANGELINI, Bromday, Bufferin, Buscopan Plus, Caldolor, Calmatel, Cambia, Canasa, Capoxigem, Cataflam, Celebrex, Celebrex ORIFARM, Children's Advil Allergy Sinus, Children's Tylenol, Children's Tylenol Cough and Runny Nose, Children's Tylenol plus cold, Children's Tylenol plus Cold and Cough, Children's Tylenol plus cold and stuffy nose, Children's Tylenol plus Flu, Children's Tylenol plus cold & allergy, Children's Tylenol plus Cough & Runny Nose, Children's Tylenol plus Cough & Sore Throat, Children's Tylenol plus multi symptom cold, Clinoril, Codral Cold and Flu, Codral Day and Night Day Tablets, Codral Day and Night Night Tablets, Codral Nighttime, Colazal, Combunox, Contac Cold plus Flu, Contac Cold plus Flu Non-Drowsy, Coricidin D, Coricidin HBP Cold and Flu, Coricidin HBP Day and Night Multi-Symptom Cold, Coricidin HBP Maximum Strength Flu, Coricidin HBP Nighttime Multi-Symptom Cold, Coricidin II Extra Strength Cold and Flu, CS502, CS670, Daypro, Daypro Alta, DDS06C, Demazin Cold and Flu, Demazin Cough, Cold and Flu, Demazin day/night Cold and Flu, Demazin PE Cold and Flu, Demazin PE day/night Cold and Flu, Diclofenac HPBCD, Dimetapp Day Relief, Dimetapp Multi-Symptom Cold and Flu, Dimetapp Night Relief, Dimetapp Pain and Fever Relief, Dimetapp PE Sinus Pain, Dimetapp PE Sinus Pain plus Allergy, Dipentum, Diractin, Disprin Cold 'n' Fever, Disprin Extra, Disprin Forte, Disprin Plus, Dristan Cold, Dristan Junior, Drixoral Plus, Duexis, Dynastat, Efferalgan, Efferalgan Plus Vitamin C, Efferalgan Vitamin C, Elixsure IB, Excedrin Back and Body, Excedrin Migraine, Excedrin PM, Excedrin Sinus Headache, Excedrin Tension Headache, Falcol, Fansamac, Feldene, Fever-All, Fiorinal, Fiorinal with Codeine, Flanax, Flector Patch, Flucam, Fortagesic, Gerbin, Giazo, Gladio, Goody's Back and Body Pain, Goody's Cool Orange, Goody's Extra Strength, Goody's PM, Greaseless Bengay, GW406381, HCT1026, He Xing Yi, Hyanalgese-D, HydrocoDex, Ibuprofen Sodium PFIZER, Ibuprofen with, Acetaminophen PFIZER, Icy Hot SANOFI AVENTIS, Impracor, Indocin, Indomethacin APP PHARMA, Indomethacin MYLAN, Infants' Tylenol, IP880, IP940, Iremod, ISV205, JNS013, Jr. Tylenol, Junifen, Junior Strength Advil, Junior Strength Motrin, Ketoprofen TDS, Lemsip Max, Lemsip Max All in One, Lemsip Max All Night, Lemsip Max Cold and Flu, Lialda, Listerine Mouth Wash, Lloyds Cream, Lodine, Lorfit P, Loxonin, LTNS001, Mersyndol, Mesalamine SALIX, Mesalamine SOFAR, Mesalazine, Mesasal GLAXO, Mesasal SANOFI, Mesulid, Metsal Heat Rub, Midol Complete, Midol Extended Relief, Midol Liquid Gels, Midol PM, Midol Teen Formula, Migranin COATED TABLETS, ML3000, Mobic, Mohrus, Motrin, Motrin Cold and Sinus Pain, Motrin PM, Movalis ASPEN, MRX7EAT, Nalfon, Nalfon PEDINOL, Naprelan, Naprosyn, Naprosyn RPG LIFE SCIENCE, Naproxen IROKO, NCX4016, NCX701, NeoProfen LUNDBECK, Nevanac, Nexcede, Niflan, Norgesic MEDICIS, Novalgin, Nuprin SCOLR, Nurofen, Nurofen Cold and Flu, Nurofen Max Strength Migraine, Nurofen Plus, Nuromol, NyQuil with Vitamin C, Ocufen, OMS103HP, Oralease, Orudis ABBOTT JAPAN, Oruvail, Osteluc, OxycoDex, P54, Panadol, Panadol Actifast, Paradine, Paramax, Parfenac, Pedea, Pennsaid, Pentasa, Pentasa ORIFARM, Peon, Percodan, Percodan-Demi, PercoDex, Percogesic, Perfalgan, PL2200, PL3100, Ponstel, Prexige, Prolensa, PSD508, R-Ketoprofen, Rantudil, Relafen, Remura, Robaxisal, Rotec, Rowasa, ROX828, RP19583, RQ00317076, Rubor, Salofalk, Salonpas, Saridon, SDX101, Seltouch, sfRowasa, Shinbaro, Sinumax, Sinutab, Sinutab, sinus, Spalt, Sprix, Strefen, Sudafed Cold and Cough, Sudafed Head Cold and Sinus, Sudafed PE Cold plus Cough, Sudafed PE Pressure plus Pain, Sudafed PE, Severe Cold, Sudafed PE Sinus Day plus Night Relief Day Tablets, Sudafed PE Sinus Day plus Night Relief Night Tablets, Sudafed PE Sinus plus Anti-inflammatory Pain Relief, Sudafed Sinus Advance, Surgam, Synalgos-DC, Synflex, Tavist allergy/sinus/headache, TDS943, TDT070, Theraflu Cold and Sore Throat, Theraflu Daytime Severe Cold and Cough, Theraflu Daytime Warming Relief, Theraflu Warming Relief Caplets Daytime Multi-Symptom Cold, Theraflu Warming Relief Cold and Chest Congestion, Thomapyrin, Thomapyrin C, Thomapyrin Effervescent, Thomapyrin Medium, Tilcotil, Tispol, Tolectin, Toradol, TPR100, TQ1011, Trauma-Salbe, Trauma-Salbe Kwizda, Treo, Treximet, Trovex, TT063, Tylenol, Tylenol Allergy Multi-Symptom, Tylenol Back Pain, Tylenol Cold & Cough Daytime, Tylenol Cold & Cough Nighttime, Tylenol Cold and Sinus Daytime, Tylenol Cold and Sinus Nighttime, Tylenol Cold Head Congestion Severe, Tylenol Cold Multi Symptom Daytime, Tylenol Cold Multi Symptom Nighttime Liquid, Tylenol Cold Multi Symptom Severe, Tylenol Cold Non-Drowsiness Formula, Tylenol Cold Severe Congestion Daytime, Tylenol Complete Cold, Cough and Flu Night time, Tylenol Flu Nighttime, Tylenol Menstrual, Tylenol PM, Tylenol Sinus Congestion & Pain Daytime, Tylenol Sinus Congestion & Pain Nighttime, Tylenol Sinus Congestion & Pain Severe, Tylenol Sinus Severe Congestion Daytime, Tylenol Ultra Relief, Tylenol with Caffeine and Codeine phosphate, Tylenol with Codeine phosphate, Ultra Strength Bengay Cream, Ultracet, UR8880, V0498TA01A, Vicks NyQuil Cold and Flu Relief, Vicoprofen, Vimovo, Voltaren Emulgel, Voltaren GEL, Voltaren NOVARTIS CONSUMER HEALTH GMBH, Voltaren XR, VT122, Xefo, Xefo Rapid, Xefocam, Xibrom, XL3, Xodol, XP20B, XP21B, XP21L, Zipsor, and Zoenasa. In another aspect, COX-2 inhibitors can be identified through methods known in the art (See, e.g., Dannhardt, G. and Kiefer, W. Cyclooxygenase inhibitors—current status and future prospects. 2001. Eur. J. Med. Chem. 36: 109-126, which is herein incorporated by reference). In some aspects, the COX-2 inhibitor is used to treat or prevent or inhibit metastasis in a patient with advanced prostate cancer. In some aspects, the COX-2 inhibitor is used in combination with a second treatment. In some aspects, the second treatment is any treatment described herein. In some aspects, the COX-2 inhibitor is used in combination with a second treatment selected from the group consisting of: Denosumab, Zometa (http://www.us.zometa.com/index.jsp?usertrack.filter_applied=true&NovaId=2935376934467633633; last accessed Dec. 2, 2012), Carbozantinib or Cabozantinib, Antibody or peptide blocking PTHLH (parathyroid hormone like hormone) or PTHrP (parathyroid hormone related protein).

In one embodiment, the treatment is Radium 223. In a preferred embodiment the Radium 223 therapy is Alpharadin (aka, Xofigo) (radium-223 dichloride). Alpharadin uses alpha radiation from radium-223 decay to kill cancer cells. Radium-223 naturally self-targets to bone metastases by virtue of its properties as a calcium-mimic. Alpha radiation has a very short range of 2-10 cells (when compared to current radiation therapy which is based on beta or gamma radiation), and therefore causes less damage to surrounding healthy tissues (particularly bone marrow). With similar properties to calcium, radium-223 is drawn to places where calcium is used to build bone in the body, including the site of faster, abnormal bone growth—such as that seen in the skeletal metastases of men with advanced, castration-resistant prostate cancer. Radium-223, after injection, is carried in the bloodstream to sites of abnormal bone growth. The place where a cancer starts in the body is known as the primary tumor. Some of these cells may break away and be carried in the bloodstream to another part of the body. The cancer cells may then settle in that part of the body and form a new tumor. If this happens it is called a secondary cancer or a metastasis. Most patients with late stage prostate cancer suffer the maximum burden of disease in their bones. The aim with radium-223 is to selectively target this secondary cancer. Any radium-223 not taken-up in the bones is quickly routed to the gut and excreted.

Alternatively a combined treatment can be carried out in which more than one agent from those mentioned above are combined to treat and/or prevent the metastasis, relapse or recurrence or said agents can be combined with other supplements, such as calcium or vitamin D or with a hormone treatment.

Method of Diagnosis or Prognosis of Metastasis, Relapse or Recurrence in Prostate Cancer Based on Detecting the Amplification or Gain of the c-MAF Gene In one aspect, the invention relates to an in vitro method for the diagnosis of metastasis, relapse or recurrence in a subject with prostate cancer (hereinafter, fourth diagnosis method of the invention) and/or for the prognosis of the tendency to develop metastasis, relapse or recurrence in a subject with prostate cancer which comprises determining if the c-MAF gene is amplified in a tumor tissue sample of said subject; wherein if said gene is amplified with respect to a control sample, then said subject has a positive diagnosis for metastasis, relapse or recurrence or a greater tendency to develop metastasis, relapse or recurrence.

The terms "c-MAF gene", "metastasis", "tumor sample", "prostate cancer", "diagnosis of metastasis in a subject with prostate cancer", "prognosis of the tendency to develop metastasis in a subject with prostate cancer", "subject", "patient", "subject having a positive diagnosis of metastasis", "subject having a greater tendency to develop metastasis", "relapse" and "recurrence" have been described in detail in the context of the first method of the invention and are equally applicable to the fourth method of the invention.

In a particular embodiment, the degree of amplification or gain of the c-MAF gene can be determined by means of determining the amplification or gain of a chromosome region containing said gene. Preferably, the chromosome region the amplification or gain of which is indicative of the existence of amplification or gain of the c-MAF gene is the locus 16q22-q24 which includes the c-MAF gene. The locus 16q22-q24 is located in chromosome 16, in the long arm of said chromosome and in a range between band 22 and band 24. This region corresponds in the NCBI database with the contigs NT_010498.15 and NT_010542.15. In another preferred embodiment, the degree of amplification or gain of the c-MAF gene can be determined by means of using a probe specific for said gene.

The fourth diagnosis/prognosis method of the invention comprises, in a first step, determining if the c-MAF gene is amplified in a tumor sample of a subject. To that end, the amplification or gain of the c-MAF gene in the tumor sample is compared with respect to a control sample.

The term "amplification of a gene" as understood herein refers to a process through which various copies of a gene or of a gene fragment are formed in an individual cell or a cell line. The copies of the gene are not necessarily located in the same chromosome. The duplicated region is often called an "amplicon". Normally, the amount of mRNA produced, i.e., the gene expression level also increases in proportion to the copy number of a particular gene.

The term "gain" refers any chromosomal copy number increase from the norm. I.e., in a diploid organism, 3 copies of a gene in a cell would be a gain. In some embodiments, "gain" includes the term "copy gain", and is used synonymously with "copy number".

In a particular embodiment, the fourth method of the invention for the diagnoses of metastasis in a subject with prostate cancer and/or for the prognosis of the tendency to develop metastasis, relapse or recurrence in a subject with prostate cancer, comprises determining the c-MAF gene copy number in a tumor sample of said subject and comparing said copy number with the copy number of a control or reference sample, wherein if the c-MAF copy number is greater with respect to the c-MAF copy number of a control sample, then the subject has a positive diagnosis of metastasis, relapse or recurrence or a greater tendency to develop metastasis, relapse or recurrence.

The control sample refers to a tumor sample of a subject with prostate cancer who has not suffered metastasis or that correspond to the median value of the c-MAF gene copy number measured in a tumor tissue collection in biopsy samples of subjects with prostate cancer who have not suffered metastasis. Said reference sample is typically obtained by combining equal amounts of samples from a subject population. If the c-MAF gene copy number is increased with respect to the copy number of said gene in the control sample, then subject has a positive diagnosis for metastasis or a greater tendency to develop metastasis.

As used herein, the term "gene copy number" refers to the copy number of a nucleic acid molecule in a cell. The gene copy number includes the gene copy number in the genomic (chromosomal) DNA of a cell. In a normal cell (non-tumoral cell), the gene copy number is normally two copies (one copy in each member of the chromosome pair). The gene copy number sometimes includes half of the gene copy number taken from samples of a cell population.

In the present invention, "increased gene copy number" is understood as when the c-MAF gene copy number is more than the copy number that a reference sample or control sample has. In particular, it can be considered that a sample has an increased c-MAF copy number when the copy number is more than 2 copies, for example, 3, 4, 5, 6, 7, 8, 9 or 10 copies, and even more than 10 copies of the c-MAF gene. In embodiments, "increased gene copy number" is determined based on an average of copies per cells counted. In embodiments, it can be considered that a sample has an increased c-MAF copy number when the average copy number per cell counted is more than 2 copies, for example, 2.1, 2.2, 2.3, 2.4, 2.5, 2.6, 2.7, 2.8, 2.9, 3, 4, 5, 6, 7, 8, 9 or 10 copies, and even more than 10 copies of the c-MAF gene.

In the present invention, "decreased gene copy number" is understood as when the c-MAF gene copy number is less than the copy number that a reference sample or control sample has. These decreased gene copy number can be caused without excluding other mechanisms by a gene or 16q23 or 16q22-24 chromosomal locus deletions. In particular, it can be considered that a sample has a decreased c-MAF copy number when the copy number is less than 2 copies of the c-MAF gene.

In the present invention, a "not increased gene copy number" is understood as when the c-MAF gene copy number or the average c-MAF gene copy number is less than the copy number that a reference sample or positive for the increase sample has. The not increased gene copy number can be caused without excluding other mechanisms by no increase in gene or 16q23 or 16q22-24 chromosomal locus amplification, copy gain or translocation. In particular, it can be considered that a sample has not an increased c-MAF copy number or c-MAF average copy number when the copy number is less than 2.1, 2.2, 2.3, 2.4, 2.5, 2.6, 2.7, 2.8, 2.9 copies of the c-MAF gene.

In some embodiments, the amplification or gain is in region at the 16q23 locus. In some embodiments, the amplification or gain is in any part of the chromosomal region between Chr. 16—79,392,959 bp to 79,663,806 bp (from centromere to telomere). In some embodiments, the amplification or gain is in the genomic region between Chr. 16—79,392,959 bp to 79,663,806 bp, but excluding DNA repeating elements. In some embodiments, amplification or gain is measured using a probe specific for that region.

In a particular embodiment, the amplification, gain or the copy number is determined by means of in situ hybridization or PCR.

Methods for determining whether the c-MAF gene or the chromosome region 16q22-q24 is amplified are widely known in the state of the art. Said methods include, without limitation, in situ hybridization (ISH) (such as fluorescence in situ hybridization (FISH), chromogenic in situ hybridization (CISH) or silver in situ hybridization (SISH)), genomic comparative hybridization or polymerase chain reaction (such as real time quantitative PCR). For any ISH method, the amplification, gain or the copy number can be determined by counting the number of fluorescent points, colored points or points with silver in the chromosomes or in the nucleus.

The fluorescence in situ hybridization (FISH) is a cytogenetic technique which is used for detecting and locating the presence or absence of specific DNA sequences in chromosomes. FISH uses fluorescence probes which only bind to some parts of the chromosome with which they show a high degree of sequence similarity. In a typical FISH method, the DNA probe is labeled with a fluorescent molecule or a hapten, typically in the form of fluor-dUTP, digoxigenin-dUTP, biotin-dUTP or hapten-dUTP which is incorporated in the DNA using enzymatic reactions, such as nick translation or PCR. The sample containing the genetic material (the chromosomes) is placed on glass slides and is denatured by a formamide treatment. The labeled probe is then hybridized with the sample containing the genetic material under suitable conditions which will be determined by the person skilled in the art. After the hybridization, the sample is viewed either directly (in the case of a probe labeled with fluorine) or indirectly (using fluorescently labeled antibodies to detect the hapten).

In the case of CISH, the probe is labeled with digoxigenin, biotin or fluorescein and is hybridized with the sample containing the genetic material in suitable conditions.

Any marking or labeling molecule which can bind to a DNA can be used to label the probes used in the fourth method of the invention, thus allowing the detection of nucleic acid molecules. Examples of labels for the labeling include, although not limited to, radioactive isotopes, enzyme substrates, cofactors, ligands, chemiluminescence agents, fluorophores, haptens, enzymes and combinations thereof. Methods for labeling and guideline for selecting suitable labels for different purposes can be found, for example, in Sambrook et al. (Molecular Cloning: A Laboratory Manual, Cold Spring Harbor, N.Y., 1989) and Ausubel et al. (In Current Protocols in Molecular Biology, John Wiley and Sons, New York, 1998).

Once the existence of amplification or gain is determined, either by directly determining the amplification or gain of the c-MAF gene or by determining the amplification or gain of the locus 16q22-q24, and after being compared with the amplification or gain of said gene in the control sample, if amplification or gain in the c-MAF gene is detected, it is indicative of the fact that the subject has a positive diagnosis for metastasis or a greater tendency to develop metastasis.

The determination of the amplification of the c-MAF gene needs to be correlated with values of a control sample or reference sample that correspond to the level of amplification of the c-MAF gene measured in a tumor tissue sample of a subject with prostate cancer who has not suffered metastasis or that correspond to the median value of the amplification of the c-MAF gene measured in a tumor tissue collection in biopsy samples of subjects with prostate cancer who have not suffered metastasis. Said reference sample is typically obtained by combining equal amounts of samples from a subject population. In general, the typical reference samples will be obtained from subjects who are clinically well documented and in whom the absence of metastasis is well characterized. The sample collection from which the reference level is derived will preferably be made up of subjects suffering the same type of cancer as the patient object of the study. Once this median value has been established, the level of amplification of c-MAF in tumor tissues of patients can be compared with this median value, and thus, if there is amplification, the subject has a positive diagnosis of metastasis or a greater tendency to develop metastasis.

In a preferred embodiment, the metastasis is bone metastasis. In a yet more preferred embodiment, the bone metastasis is osteolytic bone metastasis. As used herein, the expression "osteolytic bone metastasis" refers to a type of metastasis in which bone resorption (progressive loss of bone density) is produced in the proximity of the metastasis resulting from the stimulation of the osteoclast activity by the tumor cells and is characterized by severe pain, pathological fractures, hypercalcaemia, spinal cord compression and other syndromes resulting from nerve compression.

Method of Prognosis of Metastasis, Relapse or Recurrence in Prostate Cancer Based on Detecting the Translocation of the c-MAF Gene In another aspect, the invention relates to an in vitro method for predicting the clinical outcome of a patient suffering from prostate cancer, which comprises determining if the c-MAF gene is translocated in a sample of said subject wherein a translocation of the c-MAF gene is indicative of a poor clinical outcome.

In another aspect, the invention relates to an in vitro method for predicting the clinical outcome of a patient suffering prostate cancer, which comprises determining if the c-MAF gene is translocated in a sample of said subject wherein a translocation of the c-MAF gene is indicative of a poor clinical outcome.

In some embodiments, the translocated gene is from the region at the 16q23 locus. In some embodiments, the translocated gene is from any part of the chromosomal region between Chr. 16—79,392,959 bp to 79,663,806 bp (from centromere to telomere). In some embodiments, the translocated gene is from the genomic region between Chr. 16—79,392,959 bp to 79,663,806 bp, but excluding DNA repeating elements. In some embodiments, the translocation is measured using a probe specific for that region.

In a particular embodiment, the translocation of the c-MAF gene can be determined by means of determining the translocation of a chromosome region containing said gene. In one embodiment, the translocation is the t(14,16) translocation. In another embodiment, the chromosome region that is translocated is from locus 16q22-q24. The locus 16q22-q24 is located in chromosome 16, in the long arm of said chromosome and in a range between band 22 and band 24. This region corresponds in the NCBI database with the contigs NT_010498.15 and NT_010542.15. In a preferred embodiment, the c-MAF gene translocates to chromosome 14 at the locus 14q32, resulting in the translocation t(14, 16)(q32,q23). This translocation places the MAF gene next to the strong enhancers in the IgH locus, which, in some cases, leads to overexpression of MAF. (Eychéne, A., Rocques, N., and Puoponnot, C., A new MAFia in cancer. 2008. *Nature Reviews: Cancer.* 8: 683-693.)

In a preferred embodiment, the translocation of the c-MAF gene can be determined by means of using a probe specific for said translocation. In some embodiments, the translocation is measured using a dual color probe. In some embodiments, the translocation is measured using a dual fusion probe. In some embodiments, the translocation is measured using a dual color, dual fusion probe. In some embodiments, the translocation is measured using two separate probes.

In another preferred embodiment, the translocation of the c-MAF gene is determined using the Vysis LSI IGH/MAF Dual Color dual fusion probe (http://www.abbottmolecular.com/us/products/analyte-specific-reagent/fish/vysis-lsiigh-maf-dual-color-dual-fusion-probe.html; last accessed Nov. 5, 2012), which comprises a probe against 14q32 and 16q23. In another preferred embodiment, the translocation of the c-MAF gene is determined using a Kreatech diagnostics MAF/IGH gt(14;16) Fusion probe (http://www.kreatech.com/products/repeat-freetm-poseidontm-fish-probes/hematology/maf-igh-gt1416-fusion-probe.html; last accessed Nov. 5, 2012), an Abnova MAF FISH probe (http://www.abnova.com/products/products_detail.asp?Catalog_id=FA0375; last accessed Nov. 5, 2012), a Cancer Genetics Italia IGH/MAF Two Color, Two Fusion translocation probe (http://www.cancer-geneticsitalia.com/dna-fish-probe/ighmaf/; last accessed Nov. 5, 2012), a Creative Bioarray IGH/MAF-t(14;16)(q32;q23) FISH probe (http://www.creative-bioarray.com/products.asp?cid=35&page=10; last accessed Nov. 5, 2012), a Amp Laboratories multiple myeloma panel by FISH (http://www.aruplab.com/files/technical-bulletins/Multiple%20Myeloma%20%28MM%29%20by%20FISH.pdf; last accessed Nov. 5, 2012), an Agilent probe specific to 16q23 or 14q32 (http://www.genomics.agilent.com/ProductSearch.aspx?chr=16&start=79483700&end=79754340; last accessed Nov. 5, 2012; http://www.genomics.agilent.com/ProductSearch.aspx?Pageid=3000&ProductID=637; last accessed Nov. 5, 2012), a Dako probe specific to 16q23 or 14q32 (http://www.dako.com/us/ar42/psg42806000/baseproducts_surefish.htm?setCountry=true&purl=ar42/psg42806000/baseproducts_surefish.htm?undefined&submit=Accept%20country; last accessed Nov. 5, 2012), a Cytocell IGH/MAF Translocation, Dual Fusion Probe (http://www.zentech.be/uploads/docs/products_info/prenatalogy/cytocell%202012-2013%20catalogue%5B3%5D.pdf; last accessed Nov. 5, 2012), a Metasystems XL IGH/MAF Translocation—Dual Fusion Probe (http://www.metasystems-international.com/index.php?option=com_joodb&view=article&joobase=5&id=12%3Ad-5029-100-og&Itemid=272; last accessed Nov. 5, 2012), a Zeiss FISH Probes XL, 100 µl, IGH/MAFB (https://www.micro-shop.zeiss.com/?s=440675675dedc6&l=en&p=uk&f=r&i=5000&o=&h=25&n=l&sd=000000-0528-231-uk; last accessed Nov. 5, 2012) or a Genycell Biotech IGH/MAF Dual Fusion Probe (http://www.google.com/url?sa=t&rct=j&q=&esrc=s&source=web&cd=l&ved=0CCQQFjAA&url=http%3A%2F%2Fwww.genycell.es%2Fimages%2Fproductos%2Fbrochures%2Flphmie6_86.ppt&ei=MhGYU0i3GKWH0QG1t4DoDw&usg=AFQjCNEqQMbT8vQGjJbi9riEf31VgoFTFQ&sig2=V5IS8juEMVHB18Mv2Xx_Ww; last accessed Nov. 5, 2012)

In some embodiments, the label on the probe is a fluorophore. In some embodiments, the fluorophore on the probe is orange. In some embodiments, the fluorophore on the probe is green. In some embodiments, the fluorophore on the probe is red. In some cases, the fluorophore on the probe is yellow. In some embodiments, one probe is labeled with a red fluorophore, and one with a green fluorophore. In some embodiments, one probe is labeled with a green fluorophore and one with an orange fluorophore. In some cases, the fluorophore on the probe is yellow. For instance, if the MAF-specific probe is labeled with a red fluorophore, and the IGH-specific probe is labeled with a green fluorophore, if white is seen it indicates that the signals overlap and translocation has occurred.

In some embodiments, the fluorophore is SpectrumOrange. In some embodiments, the fluorophore is SpectrumGreen. In some embodiments, the fluorophore is DAPI. In some embodiments, the fluorophore is PlatinumBright405 In some embodiments, the fluorophore is PlatinumBright415. In some embodiments, the fluorophore is PlatinumBright495. In some embodiments, the fluorophore is PlatinumBright505. In some embodiments, the fluorophore is PlatinumBright550. In some embodiments, the fluorophore is PlatinumBright547. In some embodiments, the fluorophore is PlatinumBright570. In some embodiments, the fluorophore is PlatinumBright590. In some embodiments, the fluorophore is PlatinumBright647. In some embodiments, the fluorophore is PlatinumBright495/550. In some embodiments, the fluorophore is PlatinumBright415/495/550. In some embodiments, the fluorophore is DAPI/PlatinumBright495/550. In some embodiments, the fluorophore is FITC. In some embodiments, the fluorophore is Texas Red. In some embodiments, the fluorophore is DEAC. In some embodiments, the fluorophore is R6G. In some embodiments, the fluorophore is Cy5. In some embodiments, the fluorophore is FITC, Texas Red and DAPI. In some embodiments, a DAPI counterstain is used to visualize the translocation, amplification, gain or copy number alteration.

One embodiment of the invention comprises a method in which in a first step it is determined if the c-MAF gene is translocated in a sample of a subject. In a preferred embodiment, the sample is a tumor tissue sample.

In a particular embodiment, a method of the invention for the prognosis of the tendency to develop bone metastasis in a subject with prostate cancer comprises determining the c-MAF gene copy number in a sample of said subject wherein the c-MAF gene is translocated and comparing said copy number with the copy number of a control or reference sample, wherein if the c-MAF copy number is greater with respect to the c-MAF copy number of a control sample, then the subject has a greater tendency to develop bone metastasis.

Methods for determining whether the c-MAF gene or the chromosome region 16q22-q24 is translocated are widely known in the state of the art and include those described previously for the amplification of c-MAF. Said methods include, without limitation, in situ hybridization (ISH) (such as fluorescence in situ hybridization (FISH), chromogenic in situ hybridization (CISH) or silver in situ hybridization (SISH)), genomic comparative hybridization or polymerase chain reaction (such as real time quantitative PCR). For any ISH method, the amplification, the gain, the copy number, or the translocation can be determined by counting the number of fluorescent points, colored points or points with silver in the chromosomes or in the nucleus. In other embodiments, the detection of copy number alterations and translocations can be detected through the use of whole genome sequencing, exome sequencing or by the use of any PCR derived technology. For instance, PCR can be performed on samples of genomic DNA to detect translocation. In one embodiment, quantitative PCR is used. In one embodiment, PCR is performed with a primer specific to the c-MAF gene and a primer specific to the IGH promoter region; if a product is produced, translocation has occurred.

In some embodiments, the amplification, gain and copy number of the c-MAF gene are determined after translocation of the c-MAF gene is determined. In some embodiments, the probe is used to determine if the cell is polyploid for the c-MAF gene. In some embodiments, a determination of polyploidy is made by determining if there are more than 2 signals from the gene of interest. In some embodiments, polyploidy is determined by measuring the signal from the probe specific for the gene of interest and comparing it with a centromeric probe or other probe.

Method of Prognosis of Clinical Outcome in Prostate Cancer Based on Detecting the Amplification, Gain or Translocation of the c-MAF Gene In another aspect, the invention relates to an in vitro method (hereinafter seventh method of the invention) for predicting the clinical outcome of a patient suffering prostate cancer, which comprises determining if the c-MAF gene is amplified or translocated in a sample of said subject relative to a reference gene copy number wherein an amplification or gain of the c-MAF gene with respect to said reference gene copy number is indicative of a poor clinical outcome.

The seventh method of the invention comprises, in a first step, determining if the c-MAF gene is amplified in a sample of a subject. The determination of the amplification or gain of the c-MAF is carried out essentially as described in the fifth method of the invention. In a preferred embodiment the sample is a tumor tissue sample. In a preferred embodiment, the amplification or gain of the c-MAF gene is determined by means of determining the amplification or gain of the locus 16q23 or 16q22-q24. In another preferred embodiment, the amplification or gain of the c-MAF gene is determined by means of using a c-MAF gene-specific probe.

In a second step, the seventh method of the invention comprises comparing said copy number with the copy number of a control or reference sample, wherein if the c-MAF copy number is greater with respect to the c-MAF copy number of a control sample, then this is indicative of a poor clinical outcome.

In a preferred embodiment, the c-MAF gene is amplified with respect to a reference gene copy number when the c-MAF gene copy number is higher than the copy number that a reference sample or control sample has. In one example, the c-MAF gene is said to be "amplified" if the genomic copy number of the c-MAF gene is increased by at least about 2- (i.e., 6 copies), 3- (i.e., 8 copies), 4-, 5-, 6-, 7-, 8-, 9-, 10-, 15-, 20-, 25-, 30-, 35-, 40-, 45-, or 50-fold in a test sample relative to a control sample. In another example, a c-MAF gene is said to be "amplified" if the genomic copy number of the c-MAF gene per cell is at least about 3, 4, 5, 6, 7, 8, 9, 10, 11, 12, 13, 14, 15, 16, 17, 18, 19, 20, 21, 22, 23, 24, 25, 26, 27, 28, 29, 30, and the like.

In another embodiment, the reference gene copy number is the gene copy number in a sample of prostate cancer, from a subject who has not suffered bone metastasis.

In another embodiment, the amplification or gain is determined by means of in situ hybridization or PCR.

In another embodiment and as described in the present invention, given that the chr16q22-24, including the c-MAF gene, is amplified in prostate cancer cells is related to the presence of metastasis, relapse or recurrence the chr16q22-24, including the c-MAF gene, amplification or gain allow making decisions in terms of the most suitable therapy for the subject suffering said cancer.

Thus, in another aspect the invention relates to an in vitro method for designing a customized therapy for a subject with prostate cancer, which comprises
(i) quantifying the chr16q22-24, including the c-MAF gene, amplification in a tumor sample of said subject and
(ii) comparing the chr16q22-24, including the c-MAF gene, amplification previously obtained with the degree of amplification of said gene in a control sample,
wherein if the chr16q22-24, including the c-MAF gene, is amplified with respect to the number of copies of said genomic region in the control sample, then said subject is susceptible to receive a therapy aiming to prevent and/or treat the metastasis, relapse or recurrence. In a particular aspect of this method, the subject is then administered at least one therapeutic drug that prevents, inhibits and/or treats the bone metastasis, relapse or recurrence.
wherein if the chr16q22-24, including the c-MAF gene, is not amplified with respect to the number of copies of said genomic region in the reference sample, then said subject is not susceptible to receive a therapy for preventing the bone degradation. In a particular aspect of this method, the subject is then not administered at least one therapeutic drug that prevents, inhibits and/or treats the bone metastasis, relapse or recurrence.

The invention relates to a therapeutic drug that prevents, inhibits and/or treats the bone metastasis, relapse or recurrence from those previously listed.

Therapeutic Methods of the Invention

Treating Bone Metastasis, Relapse or Recurrence Using c-MAF Inhibitory Agents

A c-MAF gene expression inhibitory agent or an inhibitory agent of the protein encoded by said gene can be used in the treatment and/or the prevention of prostate cancer metastasis, relapse or recurrence.

Therefore, in another aspect, the invention relates to the use of a c-MAF gene expression inhibitory agent or an inhibitory agent of the protein encoded by said gene (hereinafter, inhibitory agent of the invention) in the preparation of a medicinal product for treating and/or preventing prostate cancer metastasis, relapse or recurrence. Alternatively, the invention relates to a c-MAF gene expression inhibitory agent or an inhibitory agent of the protein encoded by said gene for use in the treatment and/or the prevention of prostate cancer metastasis, relapse or recurrence. Alternatively, the invention relates to a method for treating the prostate cancer metastasis, relapse or recurrence in a subject which comprises administering a c-MAF inhibitor to said subject. As used herein, a "c-MAF inhibitory agent" refers to any molecule capable of completely or partially inhibiting the c-MAF gene expression, both by preventing the expression product of said gene from being produced (interrupting the c-MAF gene transcription and/or blocking the translation of the mRNA coming from the c-MAF gene expression) and by directly inhibiting the c-MAF protein activity. C-MAF gene expression inhibitors can be identified using methods based on the capacity of the so-called inhibitor to block the capacity of c-MAF to promote the in vitro cell proliferation, such as shown in the international patent application WO2005/046731 (hereby incorporated by reference in its entirety), based on the capacity of the so-called inhibitor to block the transcription capacity of a reporter gene under the control of the cyclin D2 promoter or of a promoter containing the c-MAF response region (MARE or c-MAF responsive element) in cells which express c-MAF such as described in WO2008098351 (hereby incorporated by reference in its entirety) or based on the capacity of the so-called inhibitor to block the expression of a reporter gene under the control of the IL-4 promoter in response to the stimulation with PMA/ionomycin in cells which express NFATc2 and c-MAF such as described in US2009048117A (hereby incorporated by reference in its entirety).

By way of non-limiting illustration, c-MAF inhibitory agents suitable for use in the present invention include antisense oligonucleotides, interference RNAs (siRNAs), catalytic RNAs or specific ribozymes and inhibitory antibodies.

Antisense Oligonucleotides

An additional aspect of the invention relates to the use of isolated "antisense" nucleic acids to inhibit expression, for example, for inhibiting transcription and/or translation of a nucleic acid which encodes c-MAF the activity of which is to be inhibited. The antisense nucleic acids can be bound to the target potential of the drug by means of conventional base complementarity or, for example, in the case of binding to Double stranded DNA through specific interaction in the large groove of the double helix. Generally, these methods refer to a range of techniques generally used in the art and they include any method which is based on the specific binding to oligonucleotide sequences.

An antisense construct of the present invention can be administered, for example, as an expression plasmid which, when is transcribed in cell, produces RNA complementary to at least one unique part of the cellular mRNA encoding c-MAF. Alternatively, the antisense construct is an oligonucleotide probe generated ex vivo which, when introduced into the cell, produces inhibition of gene expression hybridizing with the mRNA and/or gene sequences of a target nucleic acid. Such oligonucleotide probes are preferably modified oligonucleotides which are resistant to endogenous nucleases, for example, exonucleases and/or endonucleases and are therefore stable in vivo. Examples of nucleic acid molecules for use thereof as an antisense oligonucleotides are DNA analogs of phosphoramidate, phosphothionate and methylphosphonate (see also U.S. Pat. Nos. 5,176,996; 5,264,564; and 5,256,775) (hereby incorporated by reference in their entireties). Additionally, the general approximations for constructing oligomers useful in the antisense therapy have been reviewed, for example, in Van der Krol et al., BioTechniques 6: 958-976, 1988; and Stein et al., Cancer Res 48: 2659-2668, 1988.

With respect to the antisense oligonucleotide, the oligodeoxyribonucleotide regions derived from the starting site of the translation, for example, between −10 and +10 of the target gene are preferred. The antisense approximations involve the oligonucleotide design (either DNA or RNA) that are complementary to the mRNA encoding the target polypeptide. The antisense oligonucleotide will be bound to the transcribed mRNA and translation will be prevented.

The oligonucleotides which are complementary to the 5' end of the mRNA, for example the non translated 5' sequence up to and including the start codon AUG must function in the most efficient manner to inhibit translation. Nevertheless, it has been shown that the sequences complementary to the non translated 3' sequences of the mRNA are also efficient for inhibiting mRNA translation (Wagner, Nature 372: 333, 1994). Therefore, complementary oligonucleotides could be used at the non translated 5' or 3' regions, non coding regions of a gene in an antisense approximation to inhibit the translation of that mRNA. The oligonucleotides complementary to the non translated 5' region of the mRNA must include the complement of the start codon AUG. The oligonucleotides complementary to the coding region of the mRNA are less efficient translation inhibitors but they could also be used according to the invention. If they are designed to hybridize with the 5' region, 3' region or the coding region of the mRNA, the antisense nucleic acids must have at least about six nucleotides long and preferably have less than approximately 100 and more preferably less than approximately 50, 25, 17 or 10 nucleotides long.

Preferably, in vitro studies are performed first to quantify the capacity of the antisense oligonucleotides for inhibiting gene expression. Preferably these studies use controls which distinguish between antisense gene inhibition and non specific biological effects of the oligonucleotides. Also preferably these studies compared the levels of target RNA or protein with that of an internal control of RNA or protein. The results obtained using the antisense oligonucleotides can be compared with those obtained using a control oligonucleotide. Preferably the control oligonucleotide is approximately of the same length as the oligonucleotide to be assayed and that the oligonucleotide sequence does not differ from the antisense sequence more than it is deemed necessary to prevent the specific hybridization to the target sequence.

The antisense oligonucleotide can be a single or double stranded DNA or RNA or chimeric mixtures or derivatives or modified versions thereof. The oligonucleotide can be modified in the base group, the sugar group or the phosphate backbone, for example, to improve the stability of the molecule, its hybridization capacity etc. The oligonucleotide may include other bound groups, such as peptides (for example, for directing them to the receptors of the host cells) or agents for facilitating transport through the cell membrane (see, for example, Letsinger et al., Proc. Natl. Acad. Sci. U.S.A. 86: 6553-6556, 1989; Lemaitre et al., Proc. Natl. Acad. Sci. 84: 648-652, 1987; PCT Publication No. WO 88/09810) or the blood-brain barrier (see, for example, PCT Publication No. WO 89/10134), intercalating agents (see, for example, Zon, Pharm. Res. 5: 539-549, 1988). For this purpose, the oligonucleotide can be conjugated to another molecule, for example, a peptide, a transporting agent, hybridization triggered cleaving agent, etc.

The antisense oligonucleotides may comprise at least one group of modified base. The antisense oligonucleotide may also comprise at least a modified sugar group selected from the group including but not limited to arabinose, 2-fluoro-arabinose, xylulose, and hexose. The antisense oligonucleotide may also contain a backbone similar to a neutral peptide. Such molecules are known as peptide nucleic acid (PNA) oligomers and are described, for example, in Perry-O'Keefe et al., Proc. Natl. Acad. Sci. U.S.A. 93: 14670, 1996, and in Eglom et al., Nature 365: 566, 1993.

In yet another embodiment, the antisense oligonucleotide comprises at least one modified phosphate backbone. In yet another embodiment, the antisense oligonucleotide is an alpha-anomeric oligonucleotide.

While antisense oligonucleotides complementary to the coding region of the target mRNA sequence can be used, those complementary to the transcribed non translated region can also be used.

In some cases, it may be difficult to reach the sufficient intracellular concentrations of the antisense to suppress the endogenous mRNA translation. Therefore, a preferred approximation uses a recombinant DNA construct in which the antisense oligonucleotide is placed under the control of a strong pol III or pol II promoter.

Alternatively, the target gene expression can be reduced by directing deoxyribonucleotide sequences complementary to the gene regulating region (i.e., the promoter and/or enhancers) to form triple helix structures preventing gene transcription in the target cells in the body (see in general, Helene, Anticancer Drug Des. 6(6): 569-84, 1991). In certain embodiments, the antisense oligonucleotides are antisense morpholines.

siRNA

Small interfering RNA or siRNA are agents which are capable of inhibiting the expression of a target gene by means of RNA interference. A siRNA can be chemically synthesized, can be obtained by means of in vitro transcription or can be synthesized in vivo in the target cell. Typically, the siRNA consist of a double stranded RNA between 15 and 40 nucleotides long and may contain a 3' and/or 5' protruding region of 1 to 6 nucleotides. The length of the protruding region is independent of the total length of the siRNA molecule. The siRNA act by means of degrading or silencing the target messenger after transcription.

The siRNA of the invention are substantially homologous to the mRNA of the c-MAF encoding gene or to the gene sequence which encodes said protein. "Substantially homologous" is understood as having a sequence which is sufficiently complementary or similar to the target mRNA such that the siRNA is capable of degrading the latter through RNA interference. The siRNA suitable for causing said interference include siRNA formed by RNA, as well as siRNA containing different chemical modifications such as:

siRNA in which the bonds between the nucleotides are different than those appearing in nature, such as phosphorothionate bonds.

Conjugates of the RNA strand with a functional reagent, such as a fluorophore.

Modifications of the ends of the RNA strands, particularly of the 3' end by means of the modification with different hydroxyl functional groups in 2' position.

Nucleotides with modified sugars such as O-alkylated residues on 2' position like 2'-O-methylribose or 2'-O-fluororibose.

Nucleotides with modified bases such as halogenated bases (for example 5-bromouracil and 5-iodouracil), alkylated bases (for example 7-methylguanosine).

The siRNA can be used as is, i.e., in the form of a double stranded RNA with the aforementioned characteristics. Alternatively, the use of vectors containing the sense and antisense strand sequence of the siRNA is possible under the control of suitable promoters for the expression thereof in the cell of interest.

Vectors suitable for expressing siRNA are those in which the two DNA regions encoding the two strands of siRNA are arranged in tandem in one and the same DNA strand separated by a spacer region which, upon transcription, forms a loop and wherein a single promoter directs the transcription of the DNA molecule giving rise to shRNA.

Alternatively, the use of vectors in which each of the strands forming the siRNA is formed from the transcription of a different transcriptional unit is possible. These vectors are in turn divided into divergent and convergent transcription vectors. In divergent transcription vectors, the transcriptional units encoding each of the DNA strands forming the siRNA are located in tandem in a vector such that the transcription of each DNA strand depends on its own promoter which may be the same or different (Wang, J. et al., 2003, Proc. Natl. Acad. Sci. USA., 100:5103-5106 and Lee, N. S., et al., 2002, Nat. Biotechnol., 20:500-505). In convergent transcription vectors, the DNA regions giving rise to the siRNA form the sense and antisense strands of a DNA region which are flanked by two reverse promoters. After the transcription of the sense and antisense RNA strands, the latter will form the hybrid for forming a functional siRNA. Vectors with reverse promoter systems in which 2 U6 promoters (Tran, N. et al., 2003, BMC Biotechnol., 3:21), a mouse U6 promoter and a human H1 promoter (Zheng, L., et al., 2004, Proc. Natl. Acad. Sci. USA., 135-140 and WO 2005026322) and a human U6 promoter and a mouse H1 promoter (Kaykas, A. and Moon, R., 2004, BMC Cell Biol., 5:16) are used have been described.

Promoters suitable for use thereof in the expression of siRNA from convergent or divergent expression vectors include any promoter or pair of promoters compatible with the cells in which the siRNA is to be expressed. Thus, promoters suitable for the present invention include but are not necessarily limited to constitutive promoters such as those derived from the genomes of eukaryotic viruses such as the polyoma virus, adenovirus, SV40, CMV, avian sarcoma virus, hepatitis B virus, the metallothionein gene promoter, the thymidine kinase gene promoter of the herpes simplex virus, retrovirus LTR regions, the immunoglobulin gene promoter, the actin gene promoter, the EF-1alpha gene promoter as well as inducible promoters in which the protein expression depends on the addition of a molecule or an exogenous signal such as the tetracycline system, the NFkappaB/UV light system, the Cre/Lox system and the heat shock gene promoter, the regulatable RNA polymerase II promoters described in WO/2006/135436 as well as specific tissue promoters (for example, the PSA promoter described in WO2006012221). In a preferred embodiment, the promoters are RNA polymerase III promoters which act constitutively. The RNA polymerase III promoters are found in a limited number of genes such as 5S RNA, tRNA, 7SL RNA and U6 snRNA. Unlike other RNA polymerase III promoters, type III promoters do not require any intragenic sequence but rather need sequences in 5' direction comprising a TATA box in positions −34 and −24, a proximal sequence element or PSE between −66 and −47 and, in some cases, a distal sequence element or DSE between positions −265 and −149. In a preferred embodiment, the type III RNA polymerase III promoters are the human or murine H1 and U6 gene promoters. In a yet more preferred embodiment, the promoters are 2 human or murine U6 promoters, a mouse U6 promoter and a human H1 promoter or a human U6 promoter and a mouse H1 promoter.

The siRNA can be generated intracellularly from the so called shRNA (short hairpin RNA) characterized in that the antiparallel strands forming the siRNA are connected by a loop or hairpin region. The shRNAs can be encoded by plasmids or viruses, particularly retroviruses, and are under the control of a promoter. Promoters suitable for expressing shRNA are those indicated in the paragraph above for expressing siRNA.

Vectors suitable for expressing siRNA and shRNA include prokaryotic expression vectors such as pUC18, pUC19, Bluescript and the derivatives thereof, mp18, mp19, pBR322, pMB9, ColE1, pCR1, RP4, phages and shuttle vectors such as pSA3 and pAT28, yeast expression vectors such as 2-micron plasmid type vectors, integration plasmids, YEP vectors, centromeric plasmids and the like, insect cell expression vectors such as pAC series vectors and pVL series vectors, plant expression vectors such as pIBI, pEarleyGate, pAVA, pCAMBIA, pGSA, pGWB, pMDC, pMY, pORE series vectors and the like and viral vector-based (adenovirus, viruses associated with adenoviruses as well as retroviruses and particularly lentiviruses) higher eukaryotic cell expression vectors or non-viral vectors such as pcDNA3, pHCMV/Zeo, pCR3.1, pEF1/His, pIND/GS, pRc/HCMV2, pSV40/Zeo2, pTRACER-HCMV, pUB6/V5-His, pVAX1, pZeoSV2, pCI, pSVL and pKSV-10, pBPV-1, pML2d and pTDT1. In a preferred embodiment, the vectors are lentiviral vectors.

The siRNA and shRNA of the invention can be obtained using a series of techniques known by the person skilled in the art. The region of the nucleotide sequence taken as a basis for designing the siRNA is not limiting and it may contain a region of the coding sequence (between the start codon and the end codon) or it may alternatively contain sequences of the non-translated 5' or 3' region preferably between 25 and 50 nucleotides long and in any position in 3' direction position with respect to the start codon. One way of designing a siRNA involves the identification of the AA(N19)TT motifs wherein N can be any nucleotide in the c-MAF gene sequence, and the selection of those having a high G/C content. If said motif is not found, it is possible to identify the NA(N21) motif wherein N can be any nucleotide.

c-MAF specific siRNAs include the siRNA described in WO2005046731 (hereby incorporated by reference in its entirety), one of the strands of which is ACGG-CUCGAGCAGCGACAA (SEQ ID NO: 6). Other c-MAF specific siRNA sequences include but are not limited to CUUACCAGUGUGUUCACAA (SEQ ID NO: 7), UGGAAGACUACUACUGGAUG (SEQ ID NO: 8), AUUUGCAGUCAUGGAGAACC (SEQ ID NO: 9), CAAGGAGAAAUACGAGAAGU (SEQ ID NO: 10), ACAAGGAGAAAUACGAGAAG (SEQ ID NO: 11) and ACCUGGAAGACUACUACUGG (SEQ ID NO: 12).

DNA Enzymes

On the other hand, the invention also contemplates the use of DNA enzymes to inhibit the expression of the c-MAF gene of the invention. DNA enzymes incorporate some of the mechanistic features of both antisense and ribozyme technologies. DNA enzymes are designed such that they recognize a particular target nucleic acid sequence similar to the antisense oligonucleotide, nevertheless like the ribozyme they are catalytic and specifically cleave the target nucleic acid.

Ribozymes

Ribozyme molecules designed for catalytically cleaving transcription products of a target mRNA to prevent the translation of the mRNA which encodes c-MAF the activity of which is to be inhibited, can also be used. Ribozymes are enzymatic RNA molecules capable of catalyzing specific RNA cleaving. (For a review, see, Rossi, Current Biology 4: 469-471, 1994). The mechanism of a ribozyme action involves a specific hybridization of a ribozyme molecule sequence to a complementary target RNA followed by an endonucleolytic cleavage event. The composition of the ribozyme molecules preferably includes one or more sequences complementary to the target mRNA and the well-known sequence responsible for cleaving the mRNA or a functionally equivalent sequence (see, for example, U.S. Pat. No. 5,093,246).

The ribozymes used in the present invention include hammer-head ribozymes and endoribonuclease RNA (hereinafter "Cech type ribozymes") (Zaug et al., Science 224: 574-578, 1984.

The ribozymes can be formed by modified oligonucleotides (for example to improve the stability, targeting, etc.) and they should be distributed to cells expressing the target gene in vivo. A preferred distribution method involves using a DNA construct which "encodes" the ribozyme under the control of a strong constitutive pol III or pol II promoter such that the transfected cells will produce sufficient amounts of the ribozyme to destroy the endogenous target messengers and to inhibit translation. Since the ribozymes are catalytic, unlike other antisense molecules, a low intracellular concentration is required for its efficiency.

Inhibitory Antibodies

In the context of the present invention, "inhibitory antibody" is understood as any antibody capable of binding specifically to the c-MAF protein and inhibiting one or more of the functions of said protein, preferably those related to transcription. The antibodies can be prepared using any of the methods which are known by the person skilled in the art, some of which have been mentioned above. Thus, the polyclonal antibodies are prepared by means of immunizing an animal with the protein to be inhibited. The monoclonal antibodies are prepared using the method described by Kohler, Milstein et al. (Nature, 1975, 256: 495). In the context of the present invention, suitable antibodies include intact antibodies comprising a variable antigen binding region and a constant region, "Fab", "F(ab')2" and "Fab'", Fv, scFv fragments, diabodies, bispecific antibodies, alphabodies, cyclopeptides and stapled peptides. Once antibodies with c-MAF protein binding capacity are identified, those capable of inhibiting the activity of this protein will be selected using an inhibitory agent identification assay.

Inhibitory Peptides

As used herein, the term "inhibitory peptide" refers to those peptides capable of binding to the c-MAF protein and inhibiting its activity as has been explained above, i.e., preventing the c-MAF from being able to activate gene transcription.

Negative c-MAF Dominants

Since the proteins from the maf family are capable of homodimerizing and heterodimerizing with other members of the AP-1 family such as Fos and Jun, one way of inhibiting c-MAF activity is by means of using negative dominants capable of dimerizing with c-MAF but lacking the capacity for activating transcription. Thus, the negative c-MAF dominants can be any of the small maf proteins existing in the cell and lacking two-thirds of the amino terminal end containing the transactivation domain (for example, mafK, mafF, mafg and pi 8) (Fujiwara et al (1993) Oncogene 8, 2371-2380; Igarashi et al. (1995) J. Biol. Chem. 270, 7615-7624; Andrews et al. (1993) Proc. Natl. Acad. Sci. USA 90, 11488-11492; Kataoka et al. (1995) Mol. Cell. Biol. 15, 2180-2190) (Kataoka et al. (1996) Oncogene 12, 53-62).

Alternatively, the negative c-MAF dominants include c-MAF variants which maintain the capacity for dimerizing with other proteins but lack the capacity for activating transcription. These variants are, for example, those lacking the c-MAF transactivation domain located at the N-terminal end of the protein. Thus, negative c-MAF dominant variants include in an illustrative manner the variants in which at least amino acids 1 to 122, at least amino acids 1-187 or at least amino acids 1 to 257 (by considering the numbering of human c-MAF as described in U.S. Pat. No. 6,274,338, hereby incorporated by reference in its entirety) have been removed.

The invention contemplates the use of both the negative c-MAF dominant variants and of polynucleotides encoding c-MAF under the operative control of a promoter suitable for expression in target cell. The promoters that can be used for regulating the polynucleotide transcription of the invention can be constitutive promoters, i.e., promoters directing the transcription at a basal level, or inducible promoters in which the transcriptional activity requires an external signal. Constitutive promoters suitable for regulating transcription are, among others, the CMV promoter, the SV40 promoter, the DHFR promoter, the mouse mammary tumor virus (MMTV) promoter, the Ia elongation factor (EF1a) promoter, the albumin promoter, the ApoA1 promoter, the keratin promoter, the CD3 promoter, the immunoglobulin heavy or light chain promoter, the neurofilament promoter, the neuron specific enolase promoter, the L7 promoter, the CD2 promoter, the myosin light chain kinase promoter, the HOX gene promoter, the thymidine kinase promoter, the RNA polymerase II promoter, the MyoD gene promoter, the phosphoglyceratekinase (PGK) gene promoter, the low density lipoprotein (LDL) promoter, the actin gene promoter. In a preferred embodiment, the promoter regulating the expression of the transactivator is the PGK gene promoter. In a preferred embodiment, the promoter regulating the polynucleotide transcription of the invention is the RNA polymerase promoter of the T7 phage.

Preferably, the inducible promoters that can be used in the context of the present invention are those responding to an inducer agent showing zero or negligible basal expression in the absence of an inducer agent and are capable of promoting the activation of gene located in the 3' position. Depending on the type of inducer agent, the inducible promoters are classified as Tet on/off promoters (Gossen, M. and H. Bujard (1992) Proc. Natl. Acad. Sci. USA, 89:5547-5551; Gossen, M. et al., 1995, Science 268:1766-1769; Rossi, F. M. V. and H. M. Blau, 1998, Curr. Opin. Biotechnol. 9:451-456); Pip on/off promoters (U.S. Pat. No. 6,287,813); antiprogestin-dependent promoters (US 2004132086), ecdysone-dependent promoters (Christopherson et al., 1992, Proc. Natl. Acad. Sci. USA, 89:6314-6318; No et al., 1996, Proc. Natl. Acad. Sci. USA, 93:3346-3351, Suhr et al., 1998, Proc. Natl. Acad. Sci. USA, 95:7999-8004 and WO9738117), a metal-lothionein-dependent promoter (WO8604920) and rapamycin-dependent promoters (Rivera et al., 1996, Nat. Med. 2:1028-32).

Vectors suitable for expressing the polynucleotide encoding the negative c-MAF dominant variant include vectors derived from prokaryotic expression vectors such as pUC18, pUC19, Bluescript and derivatives thereof, mp18, mp19, pBR322, pMB9, ColE1, pCR1, RP4, phages and shuttle vectors such as pSA3 and pAT28, yeast expression vectors such as 2-micron type plasmid vectors, integration plasmids, YEP vectors, centromeric plasmids and the like, insect cell expression vectors such as pAC series vectors and pVL series vectors, plant expression vectors such as pIBI, pEarleyGate, pAVA, pCAMBIA, pGSA, pGWB, pMDC, pMY, pORE series vectors and the like and viral vector-based (adenoviruses, viruses associated with adenoviruses as well as retroviruses and particularly lentiviruses) higher eukaryotic cell expression vectors OR non-viral vectors such as pSilencer 4.1-CMV (Ambion), pcDNA3, pcDNA3.1/hyg pHCMV/Zeo, pCR3.1, pEF1/His, pIND/GS, pRc/HCMV2, pSV40/Zeo2, pTRACER-HCMV, pUB6/V5-His, pVAX1, pZeoSV2, pCI, pSVL and pKSV-10, pBPV-1, pML2d and pTDT1.

Other Inhibitory Compounds of the c-MAF Protein Activity

Other c-MAF inhibitory compounds suitable for use in the present invention include:

TABLE 1 small molecules with c-MAF inhibiting capacity

I  Endiandric acid H derivatives such as those described in WO2004014888 corresponding to the general formula

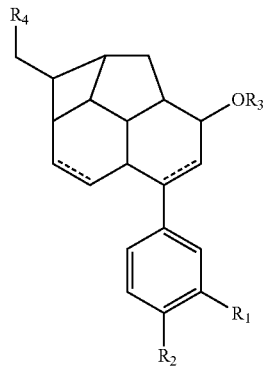

wherein
$R_1$ and $R_2$ are, independently of one another,
1.0 H or
2.0 a O—$C_1$-$C_6$-alkyl, —O—$C_2$-$C_6$-alkenyl, —O—$C_2$-$C_6$-alkynyl or —O—$C_6$-$C_{10}$-aryl group, in which alkyl, alkenyl and alkynyl are straight-chain or branched, and in which the alkyl, alkenyl and alkynyl groups are mono- or disubstituted with:
2.1 —OH,
2.2 =O,
2.3 —O—$C_1$-C6-alkyl, in which alkyl is straight-chain or branched,
2.4 —O—$C_2$-$C_6$-alkenyl, in which alkenyl is straight-chain or branched,
2.5 $C_6$-$C_{10}$-aryl,
2.6 —NH—$C_1$-$C_6$-alkyl, in which alkyl is straight-chain or branched,
2.7 —NH—$C_2$-$C_6$-alkenyl, in which alkenyl is straight-chain or branched,
2.8 —$NH_2$ or
2.9 halogen,
and in which the aryl group, is optionally mono- or disubstituted with the substituent 2.1 or 2.3 to 2.9,
in which the substituents 2.3, 2.4, 2.6 and 2.7 may be further substituted with —CN, -amide or -oxime functions, and 2.5 may be further substituted with —CN or amide functions, or $R_1$ and $R_2$ together form a ring, wherein $R_1$ and $R_2$ mean a —O—[($C_1$-$C_6$)-alkylene]—O— group, TABLE 1-continued small molecules with c-MAF inhibiting capacity R$_3$ is
1.0 H or
2.0 a O—C$_1$-C$_6$-alkyl, —O—C$_2$-C$_6$-alkenyl, —O—C$_2$-C$_6$-alkynyl or —O—C$_6$-C$_{10}$-aryl
group, in which alkyl, alkenyl and alkynyl are straight-chain or branched, and in
which the alkyl, alkenyl and alkynyl groups are mono- or disubstituted with:
2.1 —OH,
2.2 =O,
2.3 —O—C$_1$-C$_6$-alkyl, in which alkyl is straight-chain or branched,
2.4 —O—C$_2$-C$_6$-alkenyl, in which alkenyl is straight-chain or branched,
2.5 C$_6$-C$_{10}$-aryl,
2.6 —NH—C$_1$-C$_6$-alkyl, in which alkyl is straight-chain or branched,
2.7 —NH—C$_2$-C$_6$-alkenyl, in which alkenyl is straight-chain or branched,
2.8 —NH$_2$ or
2.9 halogen,
and in which the aryl group, is optionally mono- or disubstituted with the
substituent 2.1 or 2.3 to 2.9,
in which the substituents 2.3, 2.4, 2.6 and 2.7 may be further substituted with
—CN, -amide or -oxime functions, and 2.5 may be further substituted with —CN or
amide functions
R$_4$ is CO$_2$R$_3$, CO$_2$NHR$_3$, CHO, CH$_2$OR$_3$, CH$_2$OSi(R$_3$)$_3$, CH$_2$Br, CH$_2$CN, in which
R$_3$ is as defined above,
and, in particular, the compounds

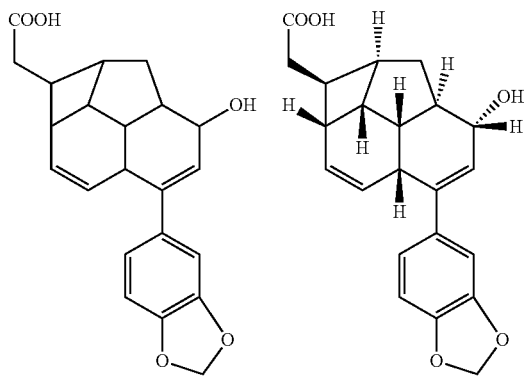

II   8-hydroxyquinoline derivatives such as those described in WO2009146546 of
general formula

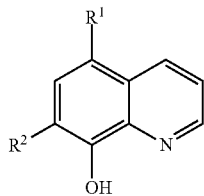

wherein
R$_1$ is selected from the group consisting of NO$_2$, NH$_2$, NH(C$_1$-C$_6$-alkyl) and
N(C$_1$-C$_6$-alkyl)(C$_1$-C$_6$-alkyl),
R$_2$ is selected from H, halogen, C$_1$-C$_6$ alkyl, and fluoro-substituted C$_1$-C$_6$ alkyl,
or
R$_1$ is Cl and R$_2$ is Br or H,
and, preferably, the compounds

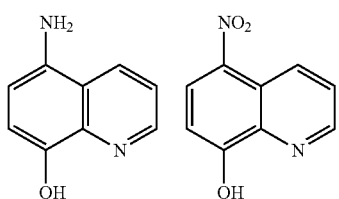

TABLE 1-continued small molecules with c-MAF inhibiting capacity

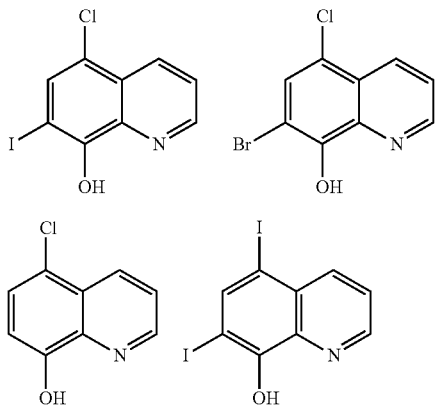

III Clioquinol (5-chloro-7-iodoquinolin-8-ol) as described in WO09049410
IV Compounds such as those described in WO08098351 of general formula

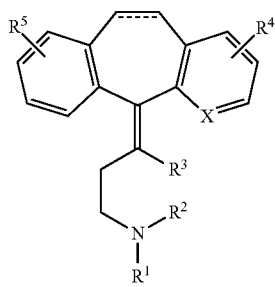

wherein
═─:─:─: is a single or double bond,
$R^1$ is selected from the group consisting of H, $C_1$-$C_4$ alkyl, C(O)O $C_1$-$C_4$ alkyl, C(O) $C_1$-$C_4$ alkyl and C(O)NH $C_1$-$C_4$ alkyl;
$R^2$ is selected from H and $C_1$-$C_4$ alkyl;
$R^3$ is selected from H and $C_1$-$C_4$ alkyl;
or $R^2$ and $R^3$ are bound together along with the carbon and nitrogen atoms to which they are bound to form a piperidine ring,
$R^4$ and $R^5$ are independently selected from H, halogen, hydroxy, $C_1$-$C_4$ alkyl, fluoro-substituted $C_1$-$C_4$ alkyl and $C_1$-$C_4$ alkoxy; and
X is selected from C and N,
and preferred compounds such as
Cyproheptadine (4-(5H-dibenzo-[a,d]cyclohepten-5-ylidene)-1-methylpiperidine hydrochloride),
Amitriptyline (3-(10,11-dihydro-5H-dibenzo[[a,d]]cycloheptene-5-ylidene)-N,N-dimethyl-1-propanamine),
Loratadine (Ethyl 4-(8-chloro-5,6-dihydro-11H-benzo[5,6]cyclohepta[1,2-b]pyridin-11-ylidene)-1-piperidinecarboxylate,
Cyclobenzrapine (3-(5H-dibenzo[a,d]cyclohepten-5-ylidene)- N,N-dimethyl-1-propanamine).
V Nivalenol (12,13-epoxy-3,4,7,15-tetrahydroxytrichothec-9-en-8-one) as described in WO0359249

Other c-MAF inhibitors are described in the patent application WO2005063252, such as shown in the following table (Table 2).

TABLE 2

| c-MAF inhibitors | |
|---|---|
| Antagonist | Reference for cdk2 inhibitory activity |
| Purine Analogs | |
| Purvalanols such as 2-(1R-Isopropyl-2-hydroxyethylamino)-6-(3-chloroanilino)-9- | Gray, N. S. et al., Science, 281, 533-538 (1998); |

TABLE 2-continued c-MAF inhibitors

| Antagonist | Reference for cdk2 inhibitory activity |
|---|---|
| isopropylpurine having a molecular formula $C_{19}H_{25}ClN_6O$ available from Sigma-Aldrich under the trade name Purvalanol A (#P4484, Sigma-Aldrich, St. Louis, MO), Purvalanol B, aminopurvalanol, compound 52 (where isopropyl of purvalanol A is replaced with H) | Chang, Y. T. et al., Chem. Biol., 6, 361-375 (1999). |
| 2-(Hydroxyethylamino)-6-benzylamino-9-methylpurine having a molecular formula $C_{15}H_{18}N_6O$ available from Sigma-Aldrich under the trade name Olomoucine (#O0886), 2-(2'-Hydroxyethylamino)-6-benzylamino-9-isopropylpurine having a molecular formula $C_{17}H_{22}N_6O$ available from Sigma-Aldrich under the trade name $N^9$-isopropylolomoucine (#I0763); CVT-313 | Vesely, J., et al., (1994) Eur. J. Biochem., 224, 771-86, 11; Brooks, E. E., et al., (1997) J. Biol. Chem., 272, 29207-11 |
| 6-(Benzylamino)-2(R)-[[1-(hydroxymethyl)propyl]amino]-9-isopropylpurine 2-(R)-[[9-(1-methylethyl)-6-[(phenylmethyl)amino]-9H-purin-2-yl]amino]-1-butanol having a molecular formula of $C_{19}H_{26}N_6O$ available from Sigma-Aldrich under the trade name Roscovitine (#R7772), methoxyroscovitine | Wang, D. et al., J. Virol., 75, 7266-7279 (2001); McClue, S. J. et al., Int. J. Cancer, 102, 463-468 (2002); Meijer, L., et al., (1997) Eur. J. Biochem., 243, 527-36 |
| Purine analog N2-(cis-2-Aminocyclohexyl)-N6-(3-chlorophenyl)-9-ethyl-9H-purine-2,6-diamine having a molecular formula of $C_{19}H_{24}ClN_7$ available from Sigma-Aldrich under the trade name CGP74514 (#C3353) | Imbach, P. et al., Bioorg. Med. Chem. Lett., 9, 91-96 (1999); Dreyer, M. K. et al., J. Med. Chem., 44, 524-530 (2001). |
| CGP79807, a purine analog of CGP74514 (supra) where Cl is replaced with CN, OH is removed, and the ortho position of cyclohexane ring is $NH_2$ | Imbach, P. et al., Bioorg. Med. Chem. Lett., 9, 91-96 (1999); Dreyer, M. K. et al., J. Med. Chem., 44, 524-530 (2001). |
| purine analog such as O6-cyclohexylmethyl guanine NU2058 | Arris, C. E. et al., J. Med. Chem., 43, 2797-2804 (2000); Davies et al, Nature Structural Biology, 9: 10, 745-749, 2002 |
| purine analog such as NU6102 | Arris, C. E. et al., J. Med. Chem., 43, 2797-2804 (2000); Davies, T. G. et al., Nat. Struct. Biol., 9, 745-749 (2002). |
| isopentenyl-adenine | Vesely, J., et al., (1994) Eur. J. Biochem., 224, 771-86 |
| Nonpurine based agents | |
| Indirubins such as indirubin-3'-monoxime having a molecular formula of $C_{16}H_{11}N_3O_2$ available from Sigma-Aldrich under the trade name (#I0404), indirubin 5-sulfonate, 5-chloro indirubin | Davies, T. G. et al., Structure, 9, 389-397 (2001); Marko, D. et al., Br. J. Cancer, 84, 283-289 (2001); Hoessel, R., et al., (1999) Nat. Cell Biol., 1, 60-7; PCT/US02/30059 to Hellberg et al., published as WO 03/027275. |
| Oxindole 1 of Fischer as referenced in column 2 of this table, (#IN118, JMAR Chemical, Indenopyrazoles | Porcs-Makkay, M., et al., Tetrahedron 2000, 56, 5893; Org. Process Res. Dev. 2000, 4, 10 Nugiel, D. A. et al., J. Med. Chem., 44, 1334-1336 (2001); Nugiel, D. A. et al., J. Med. Chem., 45, 5224-5232 (2002); Yue, E. W. et al., J. Med. Chem., 45, 5233-5248 (2002). |
| Pyrido(2,3-d)pyrimidine-7-ones, compound 3 of Fischer | Barvian, M. et al., J. Med. Chem., 43, 4606-4616 (2000); Toogood, P. L., Med. Res. Rev., 21, 487-498 (2001). |
| Quinazolines such as anilinoquinazoline | Sielecki, T. M. et al., Bioorg. Med. Chem. Lett., 11, 1157-1160 (2001); Mettey et al., J. Med. Chem. 2003, 46, 222-236. |
| Thiazoles such as fused thiazole, 4-{[(7-Oxo-6,7-dihydro-8H-[1,3]thiazolo[5,4-e]indol-8-ylidene)methyl]amino}-N-(2-pyridyl)benzenesulfonamide having a molecular formula of $C_{21}H_{15}N_5O_3S_2$ available from Sigma-Aldrich under the trade name GW8510 (#G7791) | Davis, S. T. et al., Science, 291, 134-137 (2001); PCT/US02/30059 to Hellberg et al., published as WO 03/027275. |
| Flavopiridols such as flavopiridol (L86 8275; NCS 649890, National Cancer Institute, Bethesda, MD) and a dechloro derivative | Carlson, B. A., et al., (1996) Cancer Res., 56, 2973-8 |
| Alkaloids such as Staurosporine (#S1016, A.G. Scientific, San Diego, CA) or UCN-01 (7- | Rialet, V., et al., (1991) Anticancer Res., 11, 1581-90; |

TABLE 2-continued c-MAF inhibitors

| Antagonist | Reference for cdk2 inhibitory activity |
|---|---|
| hydroxystaurosporine) National Cancer Institute, Bethesda, MD | Wang, Q., et al., (1995) Cell Growth Differ., 6, 927-36, Akiyama, T., et al., (1997) Cancer Res., 57, 1495-501, Kawakami, K., et al., (1996) Biochem, Biophys. Res. Commun., 219, 778-83 |
| Paullones such as 9-Bromo-7,12-dihydro-indolo[3,2-d][1]benzazepin-6(5H)-one having a molecular formula of $C_{16}H_{11}BrN_2O$ available from Sigma-Aldrich under the trade name kenpaullone (#K3888), or 9-Nitro-7,12-dihydroindolo-[3,2-d][1]benzazepin-6(5)-one having a molecular formula of $C_{16}H_{11}N_3O_3$ available from Sigma-Aldrich under the trade name alsterpaullone (#A4847) | Zaharevitz, D. W. et al., Cancer Res., 59, 2566-2569 (1999); Schultz, C. et al., J. Med. Chem., 42, 2909-2919 (1999); Zaharevitz, D. W., et al., (1999) Cancer Res., 59, 2566-9; PCT/US02/30059 to Hellberg et al., published as WO 03/027275. |
| CGP 41251, an alkaloid | Begemann, M., et al., (1998) Anticancer Res., 18, 2275-82; Fabbro et al., *Pharmacol Ther.* 1999 May-June; 82(2-3): 293-301 |
| Hymenialdisines such as 10z-hymenialdisine having a molecular formula of $C_{11}H_{10}BrN_5O_2$ available from Biochemicals.net, a division of A.G. Scientific, Inc. (San Diego, CA) (H-1150) | Meijer, L., et al., (1999) Chemistry & Biology, 7, 51-63; PCT/US02/30059 to Hellberg et al., published as WO 03/027275. |
| CGP60474, a phenylaminopyrimidine | 21; WO95/09853, Zimmermann et al., Sep. 21, 1994 |
| Thiazolopyrimidine 2 | Attaby et al., *Z. Naturforsch.* 54b, 788-798 (1999) |
| Diarylurea | Honma, T. et al., J. Med. Chem., 44, 4628-4640 (2001), Honma, T. et al., J. Med. Chem., 44, 4615-4627 (2001). |
| (2R)-2,5-Dihydro-4-hydroxy-2-[(4-hydroxy-3-(3-methyl-2-butenyl)phenyl)methyl]-3-(4-hydroxyphenyl)-5-oxo-2-furancarboxylic acid methyl ester having a molecular formula of $C_{24}H_{24}O_7$ available from Sigma-Aldrich under the trade name Butyrolactone-I (B7930) | Kitagawa, M. et al., Oncogene, 8, 2425-2432 (1993). |
| Aloisine A, Cat. No. 128125 (Calbiochem, San Diego, CA) | Mettey et al., *J. Med. Chem.* 2003, 46, 222-236 |

In a preferred embodiment, the c-MAF inhibitory agents are used for the treatment and/or prevention of bone metastasis, relapse or recurrence. In a yet more preferred embodiment, the bone metastasis is osteolytic metastasis.

The c-MAF inhibitory agents are typically administered in combination with a pharmaceutically acceptable carrier.

The term "carrier" refers to a diluent or an excipient whereby the active ingredient is administered. Such pharmaceutical carriers can be sterile liquids such as water and oil, including those of a petroleum, animal, plant or synthetic origin such peanut oil, soy oil, mineral oil, sesame oil and the like. Water or aqueous saline solutions and aqueous dextrose and glycerol solutions, particularly for injectable solutions, are preferably used as carriers. Suitable pharmaceutical carriers are described in "Remington's Pharmaceutical Sciences" by E. W. Martin, 1995. Preferably, the carriers of the invention are approved by the state or federal government regulatory agency or are listed in the United States Pharmacopeia or other pharmacopeia generally recognized for use thereof in animals and more particularly in human beings.

The carriers and auxiliary substances necessary for manufacturing the desired pharmaceutical dosage form of the pharmaceutical composition of the invention will depend, among other factors, on the pharmaceutical dosage form chosen. Said pharmaceutical dosage forms of the pharmaceutical composition will be manufactured according to the conventional methods known by the person skilled in the art. A review of the different methods for administering active ingredients, excipients to be used and processes for producing them can be found in "Tratado de Farmacia Galénica", C. Faulí i Trillo, Luzán 5, S. A. 1993 Edition. Examples of pharmaceutical compositions include any solid composition (tablets, pills, capsules, granules, etc.) or liquid composition (solutions, suspensions or emulsions) for oral, topical or parenteral administration. Furthermore, the pharmaceutical composition may contain, as deemed necessary, stabilizers, suspensions, preservatives, surfactants and the like.

For use in medicine, the c-MAF inhibitory agents can be found in the form of a prodrug, salt, solvate or clathrate, either isolated or in combination with additional active agents and can be formulated together with a pharmaceutically acceptable excipient. Excipients preferred for use thereof in the present invention include sugars, starches, celluloses, rubbers and proteins. In a particular embodiment, the pharmaceutical composition of the invention will be formulated in a solid pharmaceutical dosage form (for example tablets, capsules, pills, granules, suppositories, sterile crystal or amorphous solids that can be reconstituted to provide liquid forms etc.), liquid pharmaceutical dosage form (for example solutions, suspensions, emulsions, elixirs, lotions, ointments etc.) or semisolid pharmaceutical dosage form (gels, ointments, creams and the like). The pharmaceutical compositions of the invention can be administered by any route, including but not limited to the oral route, intravenous route, intramuscular route, intraarterial route, intramedularry route, intrathecal route, intraventricular router, transdermal route, subcutaneous route, intraperitoneal route, intranasal route, enteric route, topical route, sublingual route or rectal route. A review of the different ways for administering active ingredients, of the excipients to be used and of the manufacturing processes thereof can be found in Tratado de Farmacia Galénica, C. Faulí i Trillo, Luzán 5, S. A., 1993 Edition and in Remington's Pharmaceutical Sciences (A. R. Gennaro, Ed.), 20$^{th}$ edition, Williams & Wilkins PA, USA (2000). Examples of pharmaceutically acceptable carriers are known in the state of art and include phosphate buffered saline solutions, water, emulsions such as oil/water emulsions, different types of wetting agents, sterile solutions, etc. The compositions comprising said carriers can be formulated by conventional processes known in the state of the art.

In the event that nucleic acids (siRNA, polynucleotides encoding siRNA or shRNA or polynucleotides encoding negative c-MAF dominants) are administered the invention contemplates pharmaceutical compositions particularly prepared for administering said nucleic acids. The pharmaceutical compositions can comprise said naked nucleic acids, i.e., in the absence of compounds protecting the nucleic acids from degradation by the nucleases of the body, which entails the advantage that the toxicity associated with the reagents used for transfection is eliminated. Administration routes suitable for naked compounds include the intravascular route, intratumor route, intracranial route, intraperitoneal route, intrasplenic route, intramuscular route, subretinal route, subcutaneous route, mucosal route, topical route and oral route (Templeton, 2002, DNA Cell Biol., 21:857-867). Alternatively, the nucleic acids can be administered forming part of liposomes conjugated to cholesterol or conjugated to compounds capable of promoting the translocation through cell membranes such as the Tat peptide derived from the HIV-1 TAT protein, the third helix of the homeodomain of the *D. melanogaster* antennapedia protein, the herpes simplex virus VP22 protein, arginine oligomers and peptides as described in WO07069090 (Lindgren, A. et al., 2000, Trends Pharmacol. Sci, 21:99-103, Schwarze, S. R. et al., 2000, Trends Pharmacol. Sci., 21:45-48, Lundberg, M et al., 2003, Mol Therapy 8:143-150 and Snyder, E. L. and Dowdy, S. F., 2004, Pharm. Res. 21:389-393). Alternatively, the polynucleotide can be administered forming part of a plasmid vector or viral vector, preferably adenovirus-based vectors, in adeno-associated viruses or in retroviruses such as viruses based on murine leukemia virus (MLV) or on lentivirus (HIV, FIV, EIAV).

The c-MAF inhibitory agents or the pharmaceutical compositions containing them can be administered at a dose of less than 10 mg per kilogram of body weight, preferably less than 5, 2, 1, 0.5, 0.1, 0.05, 0.01, 0.005, 0.001, 0.0005, 0.0001, 0.00005 or 0.00001 mg per kg of body weight. The unit dose can be administered by injection, inhalation or topical administration.

The dose depends on the severity and the response of the condition to be treated and it may vary between several days and months or until the condition subsides. The optimal dosage can be determined by periodically measuring the concentrations of the agent in the body of the patient. The optimal dose can be determined from the EC50 values obtained by means of previous in vitro or in vivo assays in animal models. The unit dose can be administered once a day or less than once a day, preferably less than once every 2, 4, 8 or 30 days. Alternatively, it is possible to administer a starting dose followed by one or several maintenance doses, generally of a lesser amount than the starting dose. The maintenance regimen may involve treating the patient with a dose ranging between 0.01 µg and 1.4 mg/kg of body weight per day, for example 10, 1, 0.1, 0.01, 0.001, or 0.00001 mg per kg of body weight per day. The maintenance doses are preferably administered at the most once every 5, 10 or 30 days. The treatment must be continued for a time that will vary according to the type of disorder the patient suffers, the severity thereof and the condition of the patient. After treatment, the progress of the patient must be monitored to determine if the dose should be increased in the event that the disease does not respond to the treatment or the dose is reduced if an improvement of the disease is observed or if unwanted side effects are observed.

Treatment or Prevention of the Bone Degradation in Prostate Cancer Patients with Bone Metastasis, Relapse or Recurrence Having Elevated c-MAF Levels Patients suffering prostate cancer which has metastasized in bone and in which there are elevated c-MAF levels in said metastasis, relapse or recurrence may benefit particularly from therapies aimed at preventing the bone degradation caused by the increased osteoclastic activity.

Thus, in another aspect, the invention relates to the use of an agent for avoiding or preventing bone degradation in the preparation of a medicinal product for the prevention and/or the treatment of the bone metastasis, relapse or recurrence in a subject suffering prostate cancer and having elevated c-MAF levels in a tumor tissue sample, in some embodiments a metastatic tumor tissue sample, with respect to a control sample.

Alternatively, the invention relates to an agent for avoiding or preventing bone degradation for use in the prevention and/or the treatment of the bone metastasis, relapse or recurrence in a subject suffering prostate cancer and has elevated c-MAF levels in a tumor tissue sample, in some embodiments in a metastatic tumor tissue sample, with respect to a control sample.

Alternatively, the invention relates to a method of prevention and/or treatment of the degradation in a subject suffering prostate cancer and has elevated c-MAF levels in a tumor tissue sample, in some embodiments in a metastatic tumor tissue sample, with respect to a control sample, which comprises administering an agent for avoiding or preventing bone degradation to said subject.

In a particular embodiment, the bone metastasis is osteolytic metastasis.

The terms and expressions "subject", "prostate cancer", "tumor sample", "metastasis", "c-MAF gene", "increased or elevated expression levels", "relapse" or "recurrence" and "control sample" have been described in detail in relation with the first method of the invention and are equally applicable to the agent for avoiding or preventing bone degradation.

Agents capable of avoiding or preventing bone degradation suitable for the therapeutic method described in the present invention have been described in detail above in the context of the customized therapy method.

The reference or control sample is a tumor sample of a subject with prostate cancer who has not suffered metastasis or that corresponds to the median value of the c-MAF gene expression levels measured in a tumor tissue collection in biopsy samples of subjects with prostate cancer who have not suffered metastasis.

Methods for determining or quantifying if the c-MAF levels are elevated with respect to a control sample have been described in detail in relation with the first method of the invention and are equally applicable to the agent for avoiding or preventing bone degradation.

Alternatively a combined treatment can be carried out, in which more than one agent for avoiding or preventing bone degradation from those mentioned above are combined to treat and/or prevent the metastasis or said agents can be combined with other supplements, such as calcium or vitamin D or with a hormone.

The agents for avoiding or preventing bone degradation are typically administered in combination with a pharmaceutically acceptable carrier. The term "carrier" and the types of carriers have been defined above for the c-MAF inhibitory agent, as well as the form and the dose in which they can be administered and are equally applicable to the agent for avoiding or preventing bone degradation.

The following examples illustrate the invention and do not limit the scope thereof.

Kits of the Invention

In another aspect, the invention relates to a kit for predicting bone metastasis, relapse or recurrence of a prostate cancer, in a subject suffering from said cancer, the kit comprising: a) means for quantifying the expression level of c-MAF in a sample of said subject; and b) means for comparing the quantified level of expression of c-MAF in said sample to a reference c-MAF expression level.

In another aspect, the invention relates to a kit for predicting the clinical outcome of a subject suffering from bone metastasis, relapse or recurrence from a prostate cancer, the kit comprising: a) means for quantifying the expression level of c-MAF in a sample of said subject; and b) means for comparing the quantified expression level of c-MAF in said sample to a reference c-MAF expression level.

In another aspect the invention relates to a kit for determining a therapy for a subject suffering from prostate cancer, the kit comprising: a) means for quantifying the expression level of c-MAF in a sample of said subject; b) means for comparing the quantified expression level of c-MAF in said sample to a reference c-MAF expression level; and c) means for determining a therapy for preventing and/or reducing bone metastasis, relapse or recurrence in said subject based on the comparison of the quantified expression level to the reference expression level. d) means for excluding a therapy for preventing and/or reducing bone metastasis, relapse or recurrence in said subject based on the comparison of the quantified expression level to the reference expression level.

In another aspect the invention relates to a kit comprising: i) a reagent for quantifying the expression level of c-MAF in a sample of a subject suffering from prostate cancer, and ii) one or more c-MAF gene expression level indices that have been predetermined to correlate with the risk of bone metastasis, relapse or recurrence.

Means for quantifying the expression level of c-MAF in a sample of said subject have been previously described in detail including 16q23 and 16q22-24 locus amplification, gain and/or translocation. In some embodiments, the means for quantifying the c-MAF expression is any antibody, antigen binding molecule or fragment described herein. In some embodiments, the antibody is any antibody described in Int'l. Appl. No. PCT/IB2015/059562, which is incorporated herein by reference in its entirety.

In a preferred embodiment, means for quantifying expression comprise a set of probes and/or primers that specifically bind and/or amplify the c-MAF gene.

In particular embodiment the prostate cancer is prostate adenoma or prostate small cell carcinoma cancer.

In particular embodiment the kit is applied, but not limited, to a prostate cancer biopsy, circulating prostate cancer cell, circulating prostate tumor DNA.

All the particular embodiments of the methods of the present invention are applicable to the kits of the invention and to their uses.

Method for typing a sample of a subject suffering prostate cancer.

In another aspect, the invention relates to an in vitro method for typing a sample of a subject suffering from prostate cancer, the method comprising:
a) providing a sample from said subject;
b) quantifying the expression level of c-MAF in said sample;
c) typing said sample by comparing the quantified expression level of c-MAF to a predetermined reference level of c-MAF expression;
wherein said typing provides prognostic information related to the risk of bone metastasis, relapse or recurrence in said subject.

Means for quantifying the expression level of c-MAF in a sample of said subject have been previously described in detail including 16q23 and 16q22-24 locus amplification, gain and/or translocation.

In a preferred embodiment the sample is a tumor tissue sample, a circulating tumor cell or a circulating tumor DNA.

Method for classifying a subject suffering from prostate cancer.

In another aspect, the invention relates to a method for classifying a subject suffering from prostate cancer into a cohort, comprising: a) determining the expression level of c-MAF in a sample of said subject; b) comparing the expression level of c-MAF in said sample to a predetermined reference level of c-MAF expression; and c) classifying said subject into a cohort based on said expression level of c-MAF in the sample.

Means for quantifying the expression level of c-MAF in a sample of said subject have been previously described in detail including 16q23 and 16q22-24 locus amplification, gain and/or translocation.

In particular embodiment the prostate cancer is an adenoma or a small cell carcinoma.

In a preferred embodiment the sample is a tumor tissue sample, a circulating tumor cell or a circulating DNA.

In a preferred embodiment said cohort comprises at least one other individual who has been determined to have a comparable expression level of c-MAF in comparison to said reference expression level.

In another preferred embodiment said expression level of c-MAF in said sample is increased relative to said predetermined reference level, and wherein the members of the cohort are classified as having increased risk of bone metastasis, relapse or recurrence.

In another preferred embodiment said cohort is for conducting a clinical trial.

In a preferred embodiment, the sample is a tumor tissue sample.

EXAMPLES

Clinical Relevance and Prognostic Value of the Bone-Specific Metastasis Gene c-MAF was tested in a tissue micro array (TMA) including 37 Prostate tumor biopsies for which the clinical annotations of time to bone metastasis or visceral metastasis ever was known. These tumors are representative of all Prostate cancer subtypes and stages. The levels of c-MAF were determined by immunohistochemistry (IHC) using a c-MAF specific antibody and the association between the levels of c-MAF expression and risk of bone relapse was established by means of Odds ratio (OR) calculations. The OR is a measure of effect size, describing the strength of association or non-independence between two binary data. OR is described in Glas, A. S. "The diagnostic odds ratio: a single indicator of test performance" (2003) *J. of Clinical Epidemiology* 56: 1129-1135. The Odds ratio describes the strength of association or non-independence between two binary data values (gene of interest positive or negative, bone metastasis positive or negative). In some embodiments, the Odds ratio is at least about 1, 1.2, 1.2, 1.3, 1.4, 1.5, 1.6, 1.7, 1.8, 1.9, 2, 3, 4, or 5. These samples in the TMA are paraffin embedded primary tumor tissue from Prostate tumors. These samples were collected at the Vall d'Hebron Oncology Institute and Vall d'Hebron Hospital during regular clinical practice together with the relevant clinical data needed and the approval of the clinical committee.

The samples were selected fulfill the following criteria:

5 samples belonged to patients with local disease (MO) at diagnosis with a confirmed bone relapse at any time of follow-up.

29 samples belonged to patients at diagnosis that remain metastasis free after at least 5 years.

The remaining 3 tumors are from patients MO at diagnosis that latter had a relapse in any location other than bone.

Example 1 c-MAF Expression is Associated with Risk of Metastasis, in Particular Bone Metastasis
Immunohistochemistry Analysis c-MAF immunostaining was performed on TMAs. This TMA was built on glass slides and IHC was done using the Dako Link Platform according the Operating Procedure Briefly, the immunostaining was done on 3 μm TMA tumor tissue sections, placed on positively charged glass slides (Superfrost or similar) in a Dako Link platform. After deparaffinization, heat antigen retrieval was performed in pH 6.1, 0.01 mol/L citrate-based buffered solution (Dako). Endogenous peroxidase was quenched. The mouse polyclonal anti-c-MAF antibody (Santa Cruz) 1:100 dilution was used for 30 minutes at room temperature, followed by incubation with an anti-rabbit Ig dextran polymer coupled with peroxidase (Flex+, Dako). Sections were then visualized with 3,3'-diaminobenzidine (DAB) and counterstained with Hematoxylin.

c-MAF immunostaining was scored by a computerized algorithm. Nine representative images from each specimen were acquired at 10-nm wavelength intervals between 420 and 700 nm, using a DM2000 Leica microscope equipped with the Nuance FX Multispectral Imaging System (CRI Inc). The positive signals were converted from transmission to optical density units by taking the negative log of the ratio of the sample divided by the reference cube using a Beer law conversion. A computer-aided threshold was set, which created a pseudo-color image that highlighted all of the positive signals. Previous analyses supported the quantitative measurement of c-MAF expression.

Only the nuclei of epithelial cells (normal and malignant), but not stromal cells or lymphocytes, were automatically detected by setting distinct size threshold and confirmed by a pathologist. For each case was calculated the mean value of the signal intensity of all regions of interest for statistical analysis.
Prognostic and Predictive Value of c-MAF for Metastasis and Bone Metastasis in Prostate Cancer The prognostic and predictive value of c-MAF expression for metastasis of Prostate cancer was evaluated. C-MAF protein levels were determined by immunohistochemistry (IHC). MAF immunostaining was scored by a computerized measurement. The output of the computerized measurement produced a continuous data ranging from 1160 to 99760 optical density units (O.D.) for c-MAF expression. The cut off (10000 O.D.) for high and low expression was determined based on a receiving operating curve as per standard procedures.

The results are summarized in table 3.

TABLE 3

| c-MAF protein expression levels | | |
|---|---|---|
| | Bone metastasis | |
| c-MAF expression | NO | Yes |
| <=10,000 OD | 21 | 2 |
| >10,000 OD | 5 | 6 |

Based on this values the odds ratio of risk of suffering bone metastasis in the c-MAF high group versus the low was OR (bone metastasis at any time)=12.60 (95% C.I. 1.93-82.09)

Based on the second cohort analyzed, we extracted some diagnostic clinical features. c-MAF high level of protein expression predicts bone metastasis with a sensitivity of 0.75, a specificity of 0.81. This is summarized and expressed in percentages including the confidence intervals in table 4.

TABLE 4

| | | C.I. 95% |
|---|---|---|
| Sensitivity | 75.0% | 40.9%-92.9% |
| Specificity | 80.8% | 62.1%-91.5% |

The c-MAF gene or protein expression in Prostate tumors identifies a population at risk of metastasis, in particular bone metastasis at any time.

Example 2

Gain of 16q22-24 Chromosomal Region (CNA, Copy Number Alteration) is Associated with Risk of Bone Metastasis We tested whether a gain in chr16q22-q24, which included c-MAF genomic loci, is associated with risk of bone metastasis in Prostate cancer patients. To this end we used a method that identifies chr16q22-q24 amplifications, in this case by means of a chr16q23 and chr14q32 dual fluorescence in situ hybridization (FISH) probe to measure the number of copies of the chr16q22-24 region. We also used the chr14q32 probe to normalize tumor polyploidy.

Fluorescent in situ hybridization (FISH) analysis of 16q23, within the 16q22-24, genomic region amplification, including the c-MAF gene, was performed on TMA above described using a fluorescence DM2000 Leica microscope according to the Operating Procedure. We used a SpectrumOrange probe mix that flanks the MAF gene genomic region and is composed of two segments that are each approximately 350 kb with an approximately 2.2 Mb gap. The centromeric segment is located at chr16:75729985-76079705 (March 2006 assembly, UCSC Genome Browser) and the telomeric segment is located at chr16:78290003-78635873 (March 2006 assembly, UCSC Genome Browser). This probe flanks five genes VAT1L, CLEC3A, WWOX, 5srRNA and MAF (ordered from centromer to telomer).

Briefly, 16q23 region amplification, including the MAF gene, and 14q32 control region, including the IgH gene, were determined by FISH on 5 μm sections of the TMA using standard procedures. Deparaffinized tissue sections were treated with 0.2 M HCl and then with sodium thiocyanate, to eliminate salt precipitates. Pretreated slides were incubated for 10 min in a solution of proteinase K at 37° C. The slides were then postfixed in buffered formalin. The 16q23/14q32 DNA probes fluorescently labeled were denatured at 78° C. for 5 min and hybridized overnight at 37° C. on a hotplate. Washes were performed for 2 min at 72° C. in a solution of 2×SSC/0.3% Nonidet P40. Tissue sections were counterstained with 10 µl of 4,6-diamino-2-phenylindole (DAPI counterstain).

Results were captured with a fluorescence DM2000 Leica microscope and analyzed with the Nuance FX Multispectral Imaging System. FISH scoring of fluorescence signals (red for 16q23 and green for control 14q32 region) were carried out by counting the number of each region copies in an average of 50 non-overlapping nuclei for each case. The prognostic and predictive value of chromosomal 16q22-24 CNA gain association with bone metastasis in Prostate cancer was evaluated. chr16q23 and chr14q32 region number of copies per nuclei were determined by FISH. The expected number of each probe signal was two per nuclei. Amplification was considered when the average 16q23 probe signals were more than more than 1.5 when normalized per 14q32 region number of copies.

The results are summarized in table 5 and 6.

TABLE 7

Diagnostic clinical features based on Chr16q22-24 CNA gain
(>=1.5 16q23 copies per cell normalized to chr14q32)
for the prediction of prostate cancer risk of metastasis

|  |  | C.I. 95% |
| --- | --- | --- |
| Sensitivity | 75.0% | 40.9%-92.9% |
| Specificity | 93.1% | 78.0%-98.1% |

TABLE 8

Diagnostic clinical features based on Chr16q22-24 CNA gain
(>=1.5 16q23 copies per cell normalized to chr14q32)
for the prediction of prostate cancer risk of bone metastasis

|  |  | CI 95% |
| --- | --- | --- |
| Sensitivity | 60.0% | 23.1%-88.2% |
| Specificity | 96.9% | 84.3%-99.4% |

Based on these values we calculated the odds ratio of risk of suffering metastasis and bone metastasis in the chr16q22-24 gain or CNA gain positive group versus the negative. Based on this estimation, the OR for the chr16q22-24 CNA positive patients to suffer a metastasis was 40.50 (95% CI 4.72-347.82), and the OR for the chr16q22-24 CNA gain normalized using 14q32 positive patients versus the control and bone metastasis was 46.50 (95% CI 3.20-676.24). The small size of the cohort made the estimates imprecise but within a clinically relevant OR of at least 4.72 and 3.20 with a 95% confidence in each case.

Based on the data analyzed by FISH, we extracted some diagnostic clinical features. Chr16q22-24 CNA gain (>=1.5 16q23 copies per cell normalized to chr14q32) predicts Prostate cancer risk of metastasis with a sensitivity of 0.75, a specificity of 0.93. This results expressed in percentages are summarized as follows in table 7 including 95% confidence intervals (C.I.).

TABLE 5

Ratio chr16q23/chr14q32 and risk of metastasis.
A tumor will be positive for a 16q22-24 CNA gain
based on a cut off >= to 1.5 copies of the 16q23
normalized by number of copies of the 14q32.

|  | Metastasis | |
| --- | --- | --- |
| Ratio 16q23/14q32 | NO | Yes |
| <=1.5 | 27 | 2 |
| >1.5 | 2 | 6 |

Based on the data analyzed by FISH, we extracted some diagnostic clinical features. Chr16q22-24 CNA gain (>=1.5 16q23 copies per cell normalized to chr14q32) predicts Prostate cancer risk of bone metastasis with a sensitivity of 0.60, a specificity of 0.97. This results expressed in percentages are summarized as follows in table 8 including 95% confidence intervals (C.I.)

TABLE 6

Ratio chr16q23/chr14q32 > or =1.5 and
prediction of risk of bone metastasis.
A tumor will be positive for a chr16q22-24 CNA gain
based on a cut off >= to 1.5 copies of the chr16q23
normalized by number of copies of the chr14q32.

|  | Bone metastasis | |
| --- | --- | --- |
| Ratio 16q23/14q32 | NO | Yes |
| <=1.5 | 31 | 2 |
| >1.5 | 1 | 3 |

The chr16q22-24, and in particularly chr16q23, CNA gain in Prostate tumors strongly predicts and is associated with risk of metastasis and bone metastasis at any time.

Example 3

Functional Validation of c-MAF in a Bone Metastasis Colonization Assay

The causal contribution of c-MAF has been functionally validated in a bone metastasis colonization assay using preclinical experimental xenograft mouse models. Androgen resistant prostate cancer cell lines, namely DU-145 labeled with the GFP/luciferase vector were used and inoculated into immunodeficient male mice by means of intra-ventricular injection.

The standard approach used was gain of function experiments. c-MAF was expressed in DU-145 parental cell derivatives that express low levels of c-MAF in order to validate the function of c-MAF in metastasis (FIG. 1(A)). c-MAF gene bone metastasis functions were determined in vivo using bioluminescence detection of metastatic cells inoculated in the mouse intracardiacally. Cells were generated expressing each c-MAF isoform collectively. Parental DU-145 cells with or without c-MAF (short and long isoforms collectively) were injected into the left ventricle of a mouse and bone colonization was analyzed by in vivo bioluminiscent imaging. In all cases, the corresponding controls were inoculated (FIG. 1(B),(C)).

MAF overexpression enhanced the capacity and the metastatic burden of prostate cancer cells (DU-145) to metastasize the bone after intracardiac injection (FIG. 1B,C). Interestingly, MAF expressing cells render larger bone metastasis compared to parental cells (FIG. 1(C)).

The gain of function experiments altogether with the clinical validation in prostate cancer primary tumors have led to the functional validation of c-MAF as a prognostic and predictive marker and causal target gene in bone metastasis processes in prostate cancer.

All publications, patents, patent applications, internet sites, and accession numbers/database sequences including both polynucleotide and polypeptide sequences cited herein are hereby incorporated by reference herein in their entirety for all purposes to the same extent as if each individual publication, patent, patent application, internet site, or accession number/database sequence were specifically and individually indicated to be so incorporated by reference.

What is claimed is:

1. An in vitro method for designing a customized therapy for a subject with prostate cancer, comprising:
   (i) contacting a prostate tumor sample from the subject with an antibody to quantify c-MAF expression level, and
   (ii) comparing the expression level obtained in (i) with the expression level of the c-MAF in a control sample,
   wherein the antibody comprises a heavy chain CDR1 of SEQ ID NO: 21, a heavy chain CDR2 of SEQ ID NO: 22, a heavy chain CDR3 of SEQ ID NO: 23, a light chain CDR1 of SEQ ID NO: 18, a light chain CDR2 of SEQ ID NO: 19, and a light chain CDR3 of SEQ ID NO: 20,
   wherein if the expression level of the c-MAF in the tumor sample is increased with respect to the expression level of the c-MAF in the control sample, then said subject is susceptible to receive clodronate.

2. The method of claim 1, wherein the increase of c-MAF expression is at least about 1.1 times, 1.2 times, 1.3 times, 1.4 times, 1.5 times, 2 times, 3 times, 4 times, 5 times, 10 times, 20 times, 30 times, 40 times, 50 times, 60 times, 70 times, 80 times, 90 times, 100 times or greater than the control sample.

3. The method of claim 1, wherein the expression level is measured using Western blot, ELISA, immunohistochemistry or a protein array.

4. A method for treating, inhibiting, reducing the risk of and/or preventing bone metastasis, relapse or recurrence from prostate cancer in a subject suffering prostate cancer, comprising:
  (i) contacting a prostate tumor sample from the subject with an antibody to quantify c-MAF expression level,
  (ii) comparing the expression level obtained in (i) with the expression level of the c-MAF in a control sample, wherein if the expression level or the c-MAF in the tumor sample is increased with respect to the expression level of the c-MAF in the control sample, then the subject is susceptible to receive clodronate, and
  (iii) administering clodronate to said subject,
  wherein the antibody comprises a heavy chain CDR1 of SEQ ID NO: 21, a heavy chain CDR2 of SEQ ID NO: 22, a heavy chain CDR3 of SEQ ID NO: 23, a light chain CDR1 of SEQ ID NO: 18, a light chain CDR2 of SEQ ID NO: 19, and a light chain CDR3 of SEQ ID NO: 20.

5. The method of claim 4, wherein the bone metastasis is osteolytic metastasis.

6. The method of claim 4, wherein the increase of c-MAF expression is at least about 1.1 times, 1.2 times, 1.3 times, 1.4 times, 1.5 times, 2 times, 3 times, 4 times, 5 times, 10 times, 20 times, 30 times, 40 times, 50 times, 60 times, 70 times, 80 times, 90 times, 100 times or greater than the control sample.

7. The method of claim 4, wherein the expression level is measured using Western blot, ELISA, immunohistochemistry or a protein array.

8. An in vitro method for diagnosing metastasis and/or recurrence in a subject with prostate cancer and/or an in vitro method for the prognosis of the tendency to develop metastasis and/or recurrence in a subject with prostate cancer and treating said subject, comprising:
  (i) contacting a prostate tumor sample from the subject with an antibody to quantify c-MAF expression level, and
  (ii) comparing the expression level obtained in (i) with the expression level of the c-MAF in a control sample,
  wherein the antibody comprises a heavy chain CDR1 of SEQ ID NO: 21, a heavy chain CDR2 of SEQ ID NO: 22, a heavy chain CDR3 of SEQ ID NO: 23, a light chain CDR1 of SEQ ID NO: 18, a light chain CDR2 of SEQ ID NO: 19, and a light chain CDR3 of SEQ ID NO: 20,
  wherein if the expression level of the c-MAF in said tumor sample is increased with respect to the expression level of the c-MAF in the control sample, then said subject has a positive diagnosis for metastasis, relapse or recurrence or a greater tendency to develop metastasis, relapse or recurrence,
  (iii) determining that the subject has an increase in the expression level of the c-MAF in the tumor sample with respect to the control sample, and
  (iv) administering a therapeutically effective amount of clodronate to said subject.

9. The method of claim 8, wherein the bone metastasis is osteolytic metastasis.

10. The method of claim 8, wherein the increase of c-MAF expression is at least about 1.1 times, 1.2 times, 1.3 times, 1.4 times, 1.5 times, 2 times, 3 times, 4 times, 5 times, 10 times, 20 times, 30 times, 40 times, 50 times, 60 times, 70 times, 80 times, 90 times, 100 times or greater than the control sample.

11. The method of claim 8, wherein the expression level is measured using Western blot, ELISA, immunohistochemistry or a protein array.

* * * * *

UNITED STATES PATENT AND TRADEMARK OFFICE
CERTIFICATE OF CORRECTION

PATENT NO. : 11,041,213 B2  
APPLICATION NO. : 16/142168  
DATED : June 22, 2021  
INVENTOR(S) : Roger Gomis et al.

Page 1 of 1

It is certified that error appears in the above-identified patent and that said Letters Patent is hereby corrected as shown below:

In the Claims

In Column 117, Line 15, Claim 4 please delete "or" and insert --of--.

Signed and Sealed this
Twenty-first Day of September, 2021

Drew Hirshfeld
*Performing the Functions and Duties of the*
*Under Secretary of Commerce for Intellectual Property and*
*Director of the United States Patent and Trademark Office*